(12) United States Patent
Mandella et al.

(10) Patent No.: US 9,864,190 B2
(45) Date of Patent: Jan. 9, 2018

(54) CONFOCAL MICROSCOPE, SYSTEM AND METHOD THEREFOR

(75) Inventors: Michael Mandella, Palo Alto, CA (US); Gordon S. Kino, Stanford, CA (US); Christopher H. Contag, San Jose, CA (US); Olav Solgaard, Stanford, CA (US); Butrus Khuri-Yakub, Palo Alto, CA (US); Omer Oralkan, Morrisville, NC (US); Jae-Woong Jeong, Stanford, CA (US); Paul Cristman, Stanford, CA (US); Jonathan T. C. Liu, Stanford, CA (US); Hyejun Ra, Sunnyvale, CA (US); Jae Eun Hwang, Seongnam-si (KR)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 192 days.

(21) Appl. No.: 13/403,614

(22) Filed: Feb. 23, 2012

(65) Prior Publication Data

US 2012/0330157 A1 Dec. 27, 2012

Related U.S. Application Data

(60) Provisional application No. 61/446,423, filed on Feb. 24, 2011.

(51) Int. Cl.
*A61B 10/04* (2006.01)
*G02B 26/10* (2006.01)
(Continued)

(52) U.S. Cl.
CPC ........ *G02B 26/101* (2013.01); *A61B 1/00105* (2013.01); *A61B 1/043* (2013.01);
(Continued)

(58) Field of Classification Search
CPC ...................................................... A61B 10/04
(Continued)

(56) References Cited

U.S. PATENT DOCUMENTS

| 4,940,890 A * | 7/1990 | Opheij et al. ................. 250/216 |
| 6,351,325 B1 | 2/2002 | Mandella et al. |

(Continued)

FOREIGN PATENT DOCUMENTS

WO WO 2010011953 A1 * 1/2010

OTHER PUBLICATIONS

Grintech, http://www.grintech.de/gradient-index-optics.html.*
(Continued)

*Primary Examiner* — Jennifer Dieterle
*Assistant Examiner* — Lisa Kinnard
(74) *Attorney, Agent, or Firm* — Crawford Maunu PLLC

(57) ABSTRACT

Aspects of the present invention are directed to apparatuses, arrangements, systems and methods for collecting information using one or more modalities. As consistent with one or more embodiments, an apparatus includes first and second scanning mirror arrangements having different scanning axes and respectively facing different directions. The first scanning mirror arrangement directs source light and image light in two paths, and the second scanning mirror arrangement directs image light from a target to the first scanning mirror arrangement. The first and second scanning mirror arrangements cooperatively scan source light from the first scanning mirror and via the second scanning mirror to target locations with at least two degrees of freedom, and direct image light from the target locations.

23 Claims, 55 Drawing Sheets

(51) Int. Cl.

| | | |
|---|---|---|
| G02B 21/00 | (2006.01) | |
| G02B 23/24 | (2006.01) | |
| G02B 23/26 | (2006.01) | |
| A61B 1/00 | (2006.01) | |
| A61B 1/04 | (2006.01) | |
| A61B 5/00 | (2006.01) | |
| A61B 8/12 | (2006.01) | |
| A61B 8/00 | (2006.01) | |
| A61B 8/08 | (2006.01) | |
| G02B 17/08 | (2006.01) | |

(52) U.S. Cl.
CPC ........ *A61B 5/0068* (2013.01); *G02B 21/0028* (2013.01); *G02B 23/2423* (2013.01); *G02B 23/26* (2013.01); *A61B 8/12* (2013.01); *A61B 8/4483* (2013.01); *A61B 8/483* (2013.01); *G02B 17/0808* (2013.01)

(58) Field of Classification Search
USPC .......................................................... 600/443
See application file for complete search history.

(56) References Cited

U.S. PATENT DOCUMENTS

| | | | |
|---|---|---|---|
| 6,369,928 | B1 | 4/2002 | Mandella et al. |
| 6,414,779 | B1* | 7/2002 | Mandella ............ A61B 1/00183 359/201.1 |
| 6,423,956 | B1 | 7/2002 | Mandella et al. |
| 6,429,968 | B1* | 8/2002 | Carver ........................ 359/385 |
| 6,430,109 | B1 | 8/2002 | Khuri-Yakub et al. |
| 6,441,356 | B1 | 8/2002 | Mandella et al. |
| 6,522,444 | B2 | 2/2003 | Mandella et al. |
| 6,560,039 | B1 | 5/2003 | Webb et al. |
| 6,710,316 | B2 | 3/2004 | Mandella et al. |
| 6,713,742 | B2 | 3/2004 | Mandella et al. |
| 7,130,042 | B2 | 10/2006 | Kino et al. |
| 7,154,084 | B2* | 12/2006 | Hara ........................... 250/234 |
| 7,214,940 | B2* | 5/2007 | Cluff et al. ................. 250/341.1 |
| 7,242,521 | B2* | 7/2007 | Mandella et al. ........... 359/368 |
| 7,545,075 | B2 | 6/2009 | Huang et al. |
| 7,615,834 | B2 | 11/2009 | Khuri-Yakub et al. |
| 7,741,686 | B2 | 6/2010 | Khuri-Yakub et al. |
| 7,745,248 | B2 | 6/2010 | Park et al. |
| 7,745,973 | B2 | 6/2010 | Bayram et al. |
| 2001/0055462 | A1* | 12/2001 | Seibel ......................... 385/147 |
| 2004/0051050 | A1* | 3/2004 | Schmid ................ G01N 21/278 250/458.1 |
| 2005/0146784 | A1* | 7/2005 | Vogt ............................ 359/368 |
| 2007/0092447 | A1* | 4/2007 | Padilla De Jesus et al. .. 424/9.1 |
| 2007/0229801 | A1* | 10/2007 | Tearney ............... A61B 5/0062 356/73 |
| 2007/0247630 | A1* | 10/2007 | Herring .................... G01B 9/04 356/458 |
| 2008/0130103 | A1* | 6/2008 | Hara et al. .................. 359/369 |
| 2008/0277567 | A1* | 11/2008 | Doran ................. G01N 21/4795 250/227.2 |
| 2009/0122651 | A1 | 5/2009 | Kupnik et al. |
| 2009/0264707 | A1* | 10/2009 | Hendriks et al. ............ 600/181 |
| 2010/0046889 | A1* | 2/2010 | Peng ...................... G02B 6/124 385/36 |
| 2010/0173437 | A1 | 7/2010 | Wygant et al. |
| 2010/0252634 | A1* | 10/2010 | Good ................... G06K 7/10603 235/462.38 |
| 2011/0125029 | A1* | 5/2011 | Wang et al. .................. 600/476 |

OTHER PUBLICATIONS

Gradient Index Optics, paragraph 2; http://www.grintech.de/gradient-index-optics.html.*

Huang, D.; Swanson, E. A.; Lin, C. P.; Schuman, J. S.; Stinson, W. G.; Chang, W.; Hee, M. R.; Flotte, T.; Gregory, K.; Puliafito, C. A. and Fujimoto, J. G., "Optical Coherence Tomography," Science 254, pp. 1178-1181, (1991).

Tearney, G. J.; Brezinski, M. E.; Bouma, B. E.; Boppart, S. A; Pitris, C.; Southern, J. F. and Fujimoto, J. G., "In Vivo Endoscopic Optical Biopsy with Optical Coherence Tomography," Science 276, 2037-2039, (1997).

Papworth, G. D.; Delaney, P. M.; Bussau, L. J.; Vo, L. T. and King, R. G., "In Vivo Fibre Optic Confocal Imaging of Microvasculature and Nerves in the Rat Vas Deferens and Colon", J. Anatomy 192, 489-495, (1998).

Sabharwal Y. S.; Rouse A. R.; Donaldson L.; Hopkins M. F. and Gmitro A. F., "Slit-Scanning Confocal Microendoscope for High-Resolution In Vivo Imaging", Appl Opt 38, pp. 7133-7144, (1999).

Parker, M.; Pisani, P. and Ferlay, J., "Estimates of the Worldwide Incidence of 25 Major Cancers in 1990", Int. J. Cancer 80, pp. 827-841, (1999).

Rouse, A. R. and Gmitro, A. F., "Multispectral Imaging with a Confocal Microendoscope", Opt Lett 25, pp. 1708-1710, (2000).

Pan, Y.; Xie, H. and Fedder, G. K., "Endoscopic Optical Coherence Tomography Based on a Microelectromechanical Mirror", Opt Lett 26, pp. 1966-1968, (2001).

Liang, C.; Sung, K-B.; Richards-Kortum, R. R. and Descour, M. R., "Design of a High-Numerical Aperture Miniature Microscope Objective for an Endoscopic Fiber Confocal Reflectance Microscope", Applied Optics 41, pp. 4603-4610, (2002).

Zipfel, W. R.; Williams, R. M. and Webb, W. W., "Nonlinear Magic: Multiphoton Microscopy in the Biosciences", Nat Biotechnol 21, pp. 1369-1377, (2003).

Wang, T. D.; Mandella, M. J.; Contag, C. H.; Chan, N. Y. and Kino, G. S., "Dual Axes Confocal Microscope with Post-Objective Scanning and Low Coherence Heterodyne Detection," Optics Letters 28, pp. 1915-1917, (2003).

Wang, T. D.; Mandella, M. J.; Contag, C. H. and Kino, G. S., "Dual Axes Confocal Microscope for High-Resolution In Vivo Imaging", Optics Letters 28, pp. 414-416, (2003).

Amos, W. B. and White J. G., "How the Confocal Laser Scanning Microscope Entered Biological Research", Biol Cell 95, pp. 335-342, (2003).

Rouse, A. R.; Kano, A; Udovich, J. A.; Kroto, S. M. and Gmitro, A. F., "Design and Demonstration of a Miniature Catheter for a Confocal Microendoscope", Appl Opt 43, pp. 5763-5771, (2004).

Laemmel, E; Genet, M.; Le Goualher, G.; Perchant, A.; Le Gargasson, J-F. and Vicaut, E., Fibered Confocal Fluorescence Microscopy (Cell-viZio) Facilitates Extended Imaging in the Field of Microcirculation. A Comparison with Intravital Microscopy:, J Vasc Res 41, pp. 400-411, (2004).

Wang, T. D.; Contag, C. H.; Mandella, M. J.; Chan, N. Y. and Kino, G. S., "Confocal Fluorescence Microscope with Dual-Axis Architecture and Biaxial Postobjective Scanning", Journal of Biomedical Optics 9(4), pp. 735-742, (2004).

Carlson, K.; Chidley, M.; Sung, K.-B.; Descour, M.; Gillenwater, A.; Follen, M. and Richards-Kortum, R., "In Vivo Fiber-Optic Confocal Reflectance Microscope with an Injection-Molded Plastic Miniature Objective Lens", Appl. Opt. 44, pp. 1792-1797, (2005).

Conchello, J-A. and Lichtman J. W., "Optical Sectioning Microscopy", Nat Methods 2, pp. 920-931, (2005).

Helmchen, F. and Denk, W., "Deep Tissue Two-Photon Microscopy", Nat Methods 2, pp. 932-940, (2005).

Li, M-L.; Zhang, H. F.; Maslov, K.; Stoica, G. and Wang, L. V., "Improved In Vivo Photoacoustic Microscopy Based on a Virtualdetector Concept," Opt. Lett. 31, pp. 474-476, (2006).

Piyawattanametha, W.; Barretto, R. P. J.; Ko, T. H.; Flusberg, B. A.; Cocker, E. D.; Ra, H.; Lee, D.; Solgaard, O. and Schnitzer, M. J., "Fast-Scanning Two-Photon Fluorescence Imaging Based on a Microelectromechanical Systems Two-Dimensional Scanning Mirror", Opt Lett 31, pp. 2018-2020, (2006).

Wong, L. K.; Mandella, M. J.; Kino, G. S. and Wang, T. D., "Improved Rejection of Multiply-Scattered Photons in Confocal Microscopy using Dual-Axes Architecture", Optics Letters, vol. 32, No. 12, 1674-1676, (2007).

Liu, J. T. C.; Mandella, M. J.; Ra, H.; Wong, L. K.; Solgaard, O.; Kino, G. S.; Piyawattanametha, W.; Contag, C. H. and Wang, T. D., "Miniature Near-Infrared Dual-Axes Confocal Microscope Utilizing a Two-Dimensional Microelectromechanical Systems Scanner", Optics Letters, vol. 32, No. 3, pp. 256-258, (2007).

(56) References Cited

OTHER PUBLICATIONS

Ra, H.; Piyawattanametha, W.; Taguchi, Y.; Lee, D.; Mandella, M. J. and Solgaard, O., "Two-Dimensional MEMS Scanner for Dual-Axes Confocal Microscopy", Journal of Microelectromechanical Systems, vol. 16, No. 4, pp. 969-976, (2007).

Yang, X. M.; Li, M. L. and Wang, L. V., "Ring-Based Ultrasonic Virtual Point Detector With Applications to Photoacoustic Tomography," Appl. Phys. Lett. 90, 251103 (2007).

Jean, F.; Bourg-Heckly, G. and Viellerobe, B., "Fibered Confocal Spectroscopy and Multicolor Imaging System for In Vivo Fluorescence Analysis", Opt Express 15, pp. 4008-4017, (2007).

Shin, H-J.; Pierce, M. C.; Lee, D.; Ra, H.; Solgaard, O. and Richards-Kortum, R., Fiber-Optic Confocal Microscope Using a MEMS Scanner and Miniature Objective Lens. Opt Express 15, pp. 9113-9122, (2007).

Fu, L.; Jain, A.; Cranfield, C.; Xie, H. and Gu, M., "Three-Dimensional Nonlinear Optical Endoscopy", J Biomed Opt 12: 040501, (2007).

Muldoon, T. J.; Pierce, M.C.; Nida, D. L.; Williams, M.D.; Gillenwater, A. and Richards-Kortum, R., "Subcellular-Resolution Molecular Imaging Within Living Tissue by Fiber Microendoscopy", Opt Express 15, pp. 16413-16423, (2007).

Makhlouf, H.; Gmitro, A. F.; Tanbakuchi, A. A.; Udovich, J. A. and Rouse, A. R., "Multispectral Confocal Microendoscope for In Vivo and In Situ Imaging", J Biomed Opt 13, 044016, (2008).

Park, S.; Karpiouk, A. B.; Aglyamov, S. R. and Emelianov, S. Y., "Adaptive Beamforming for Photoacoustic Imaging", Opt. Lett. 33, pp. 1291-1293, (2008).

Maslov, K.; Zhang, F. H.; Hu, S. and Wang, L. V., "Optical-Resolution Photoacoustic Microscopy for In Vivo Imaging of Single Capillaries," Opt. Lett. 33, pp. 929-931, (2008).

Wang, L. V., "Tutorial on Photoacoustic Microscopy and Computed Tomography", IEEE J. Sel. Top. Quantum Electron. 14, pp. 171-179, (2008).

Ra, H.; Piyawattanametha, W.; Mandella, M. J.; Hsiung, P. L.; Hardy, J.; Wang, T. D.; Contag, C. H.; Kino, G. S. and Solgaard, O., "Three-Dimensional In Vivo Imaging by a Handheld Dual-Axes Microscope", OptiCS Express, vol. 16, No. 10, pp. 7224-7232, (2008).

Piyawattanametha, W.; Ra, H.; Mandella, M. J.; Loewke, K.; Wang, T. D.; Kino, G. S.; Solgaard, O. and Contag, C. H., "3-D Near-Infrared Fluorescence Imaging Using a MEMS-Based Miniature Dual-Axis Confocal microscope", IEEE Journal of Selected Topics in Quantum Electronics, vol. 15 (5) pp. 1344-1350, (2009).

Gonzalez-Gonzalez, E.; Ra, H.; Nickerson, R. P.; Wang, Q.; Piyawattanametha, W.; Mandella, M. J.; Kino, G. S.; Leake, D.; Avilion, A. A.; Solgaard, O.; Doyle, T. C.; Contag, C. H. and Kaspar, R. L., "siRNA Silencing of Keratinocyte-Specific GFP Expression in a Transgenic Mouse Skin Model", Gene Therapy, 16, pp. 963-972, May 2009.

Ren, H; Waltzer, W. C.; Bhalla, R.; Liu, J.; Yuan, Z.; Lee, C. S. D.; Darras, F.; Schulsinger, D.; Adler, H. L.; Kim, J.; Mishail, A. and Pan, Y., "Diagnosis of Bladder Cancer with Microelectromechanical Systems-Based Cystoscopic Optical Coherence Tomography", Urology 74(6), pp. 1351-1357, (2009).

Hu, S.; Maslov, K.; Tsytsarev, V. and Wang, L. V., "Functional Transcranial Brain Imaging by Optical-Resolution Photoacoustic Microscopy", J. Biomed. Opt. 14, 040503, (2009).

Hu, S.; Maslov, K. and Wang, L. V., "In Vivo Functional Chronic Imaging of a Small Animal Model Using Optical-Resolution Photoacoustic Microscopy", Med. Phys. 36, pp. 2320-2323, (2009).

Hu, S.; Maslov, K. and Wang, L. V., "Noninvasive Label-Free Imaging of Microhemodynamics by Optical-Resolution Photoacoustic Microscopy," Opt. Express 17, pp. 7688-7693, (2009).

Liu, J. T. C.; Helms, M. W.; Mandella, M. J.; Crawford, J. M.; Kino, G. S. and Contag, C. H., "Quantifying Cell-Surface Biomarker Expression in Thick Tissues With Ratiometric Three-Dimensional Microscopy", Biophysical Journal 96, pp. 2405-2414, (2009).

Sun, Y.; Phipps, J.; Elson, D. S.; Stoy, H.; Tinling, S.; Meier, J.; Poirier, B.; Chuang, F. S.; Farwell, D. G. and Marcu, L., "Fluorescence Lifetime Imaging Microscopy: In Vivo Application to Diagnosis of Oral Carcinoma", Opt Lett 34, pp. 2081-2083, (2009).

Wang, B.-G.; König, K. and Halbhuber, K.-J., "Two-Photon Microscopy of Deep Intravital Tissues and its Merits in Clinical Research", J Microsc 238, pp. 1-20, (2010).

Shin, D.; Pierce, M. C.; Gillenwater, A. M.; Williams, M. D. and Richards-Kortum, R. R., "A Fiber-Optic Fluorescence Microscope Using a Consumer-Grade Digital Camera for In Vivo Cellular Imaging", PLoS ONE, vol. 5, Issue 6: e11218, (2010).

Kumar, K.; Avritscher, R.; Wang, Y.; Lane, N.; Madoff, D. C.; Yu, T.-K.; Uhr, J. W. and Zhang, X., "Handheld Histology-Equivalent Sectioning Laser-Scanning Confocal Optical Microscope for Interventional Imaging", Biomed Microdevices 12, pp. 223-233, (2010).

Ra, H.; Gonzalez-Gonzalez, E.; Smith, B. R.; Gambhir, S. S.; Kino, G. S.; Solgaard, O.; Kaspar, R. L. and Contag, C. H., "Assessing Delivery and Quantifying Efficacy of Small Interfering Ribonucleic Acid Therapeutics in the Skin Using a Dual-Axis Confocal Microscope", Journal of Biomedical Optics vol. 15 (3) pp. 036027, (2010).

Hu, S.; Rao, B.; Maslov, K. and Wang, L. V., "Label-Free Photoacoustic Ophthalmic Angiography," Opt. Lett., vol. 35 (1), (2010).

Hu, S.; Yan, P.; Maslov, K.; Lee, J.-M. and Wang, L. V., "Intravital Imaging of Amyloid Plaques in a Transgenic Mouse Model Using Optical-Resolution Photoacoustic Microscopy", Opt. Lett., 34(24), pp. 3899-3901, (2009).

* cited by examiner

Prostaglandin-Endoperoxide Synthase-2 (cyclooxygenase-2; Cox-2)

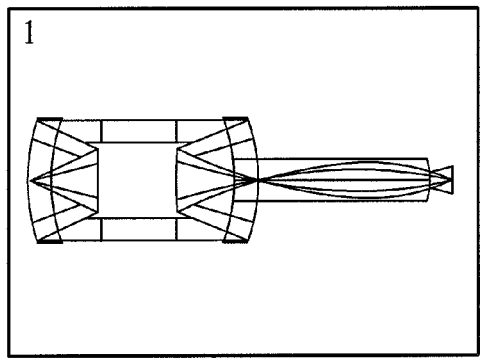
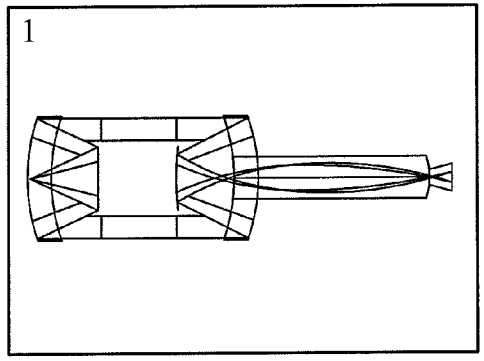
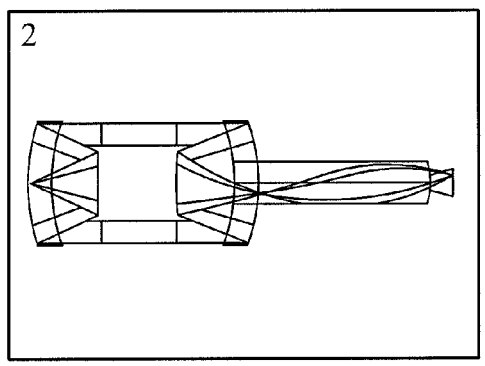
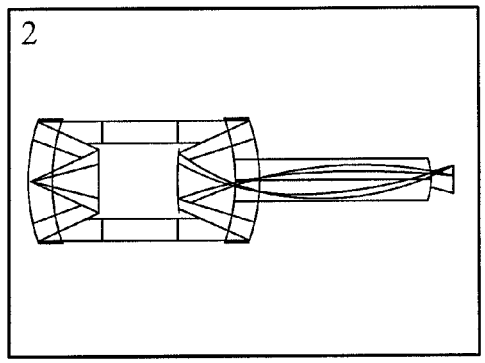
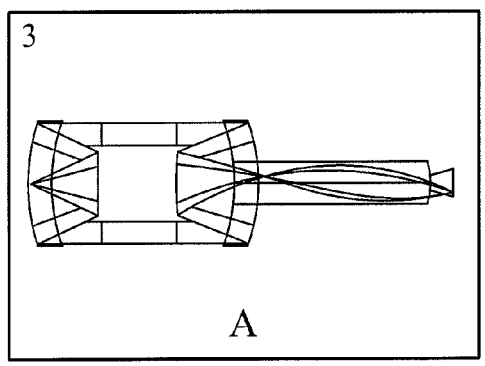
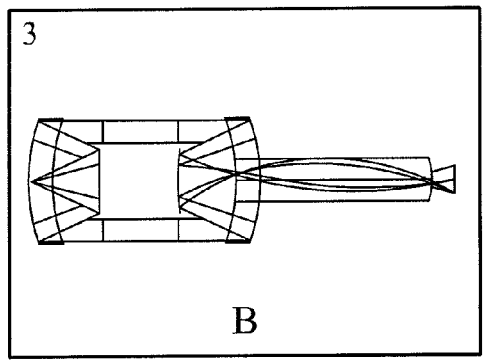
A          B
FIG. 23

CONFOCAL MICROSCOPE, SYSTEM AND METHOD THEREFOR

RELATED DOCUMENTS

This patent document claims benefit under 35 U.S.C. §119 to U.S. Provisional Patent Application Ser. No. 61/446,423, entitled "Endoscopes, Endoscope Systems and Method Therefor" and filed on Feb. 24, 2011; this patent document and the Appendices filed in the underlying provisional application, including the references cited therein, are fully incorporated herein by reference.

FEDERALLY-SPONSORED RESEARCH AND DEVELOPMENT

This invention was made with Government support under contract CA136465 awarded by the NIH National Cancer Institute. The Government has certain rights in this invention.

BACKGROUND

Confocal microscopes are applicable for implementation in a variety of fields. For example, confocal microscopes can be used to obtain images, for guidance and other applications with medical imaging technologies for which imaging systems such as CT, MRI, and PET have been used. However, while confocal microscopes have exquisite resolution, many have large bulk optics and relatively slow scan speeds, which can present challenges to the implementation of confocal microscopes in a variety of applications.

A variety of confocal microscopes and related applications have involved the use of micro-electro-mechanical systems (MEMS) scanners, and other miniaturized components for optical, mechanical and/or electrical aspects of such microscopes. For example, dual-axis confocal (DAC) microscopes provide two separate beams for the illumination and collection of light, which are respectively aligned to overlap each other at a common confocal image-point. These illumination and collection beams are synchronously scanned and de-scanned respectively by a single scanning mirror.

While useful in a variety of applications, these approaches have been difficult to implement under various imaging conditions and to achieve certain results. For example, various optical components such as lenses can be difficult and/or expensive to miniaturize, or suffer from issues such as those relating to beam aberrations. In addition, many such approaches have not been capable of producing a device having a desirable field of view (FOV) and working distance (WD).

SUMMARY

Various example embodiments are directed to confocal microscope devices, systems and methods, including applications such as those discussed above.

According to an example embodiment, an apparatus or method of manufacture consistent with this disclosure involves scanning mirrors and collimating mirrors, that directs light between a light source and a target, and from the target for imaging thereof. A dual-axis scanning mirror has two axes of movement and re-directs light in two paths to and from a first collimating mirror, for both illuminating and obtaining an image from the target. The first collimating mirror reflects source light from the dual-axis scanning mirror to a second collimating mirror in two collimated beams, and directs collimated light from the second collimating mirror to the dual-axis scanning mirror. The second collimating mirror redirects the collimated source light received from the first collimating mirror to a single-axis scanning mirror, and directs light from the single-axis scanning mirror to the first collimating mirror in two collimated beams. The single-axis scanning mirror directs light from the second collimating mirror to a target, and moves along an axis to vary the working distance to the target.

Other example embodiments are directed to an apparatus having first and second scanning mirror arrangements that respectively face in different directions. The first scanning mirror arrangement directs source light and image light in two paths, and the second scanning mirror arrangement directs image light from a target to the first scanning mirror arrangement. The first and second scanning mirror arrangements have different scanning axes and being cooperatively arranged to scan source light directed from the first scanning mirror and via the second scanning mirror to target locations with at least two degrees of freedom, and to direct image light from the target locations via the second scanning mirror arrangement to the first scanning mirror arrangement.

A more specific embodiment is directed to a multimodal endoscopic apparatus having a scan-engine module, a multimodal end-piece interface that interfaces with a plurality of different end pieces for acquiring information for multiple modalities, and optics that direct light between the first and second scanning mirror arrangements. The scan-engine module includes a first scanning mirror arrangement facing a first direction and configured and arranged to direct source light and image light in two paths, and a second scanning mirror arrangement facing a second direction that is different than the first direction. The scanning mirror arrangements are cooperatively arranged to direct light received from the first scanning mirror arrangement to a target, and to direct image light from the target to the first scanning mirror arrangement. The scanning mirror arrangements also cooperatively scan light about different scanning axes to collectively provide three degrees of freedom for scanning the target, such as for scanning light with variability in x and y (lateral) directions as well as in a z (vertical) direction to target locations within a specimen (e.g., tissue).

Another example embodiment is directed to an endoscopic apparatus having both single-axis and dual-axis scanning mirror arrangements, as well as first and second beam-shaping mirrors. The dual-axis scanning mirror arrangement has two axes of movement and operates to re-direct light in two paths respectively for source light and image light. The first beam-shaping mirror redirects source light from the dual-axis scanning mirror in two collimated beams, and redirects collimated light to the dual-axis scanning mirror arrangement. The second beam-shaping mirror redirects the collimated source light from the first mirror, and redirects image light to the first mirror. The single-axis scanning mirror directs the collimated light received from the second beam-shaping mirror to a target, directs image light from the target to the second beam-shaping mirror, and moves along an axis to vary the working distance to the target.

The above discussion is not intended to describe each embodiment or every implementation of the present disclosure. The figures and following description also exemplify various embodiments.

BRIEF DESCRIPTION OF THE DRAWINGS

Various example embodiments may be more completely understood in consideration of the following detailed description in connection with the accompanying drawings, and those in the attached Appendices that form part of this patent document.

FIGS. 23A and 23B show ray traces of the beams within the DAC scan-engine and the 1X GRIN relay lens during optical scanning, in accordance with the instant disclosure;

Figure 1:
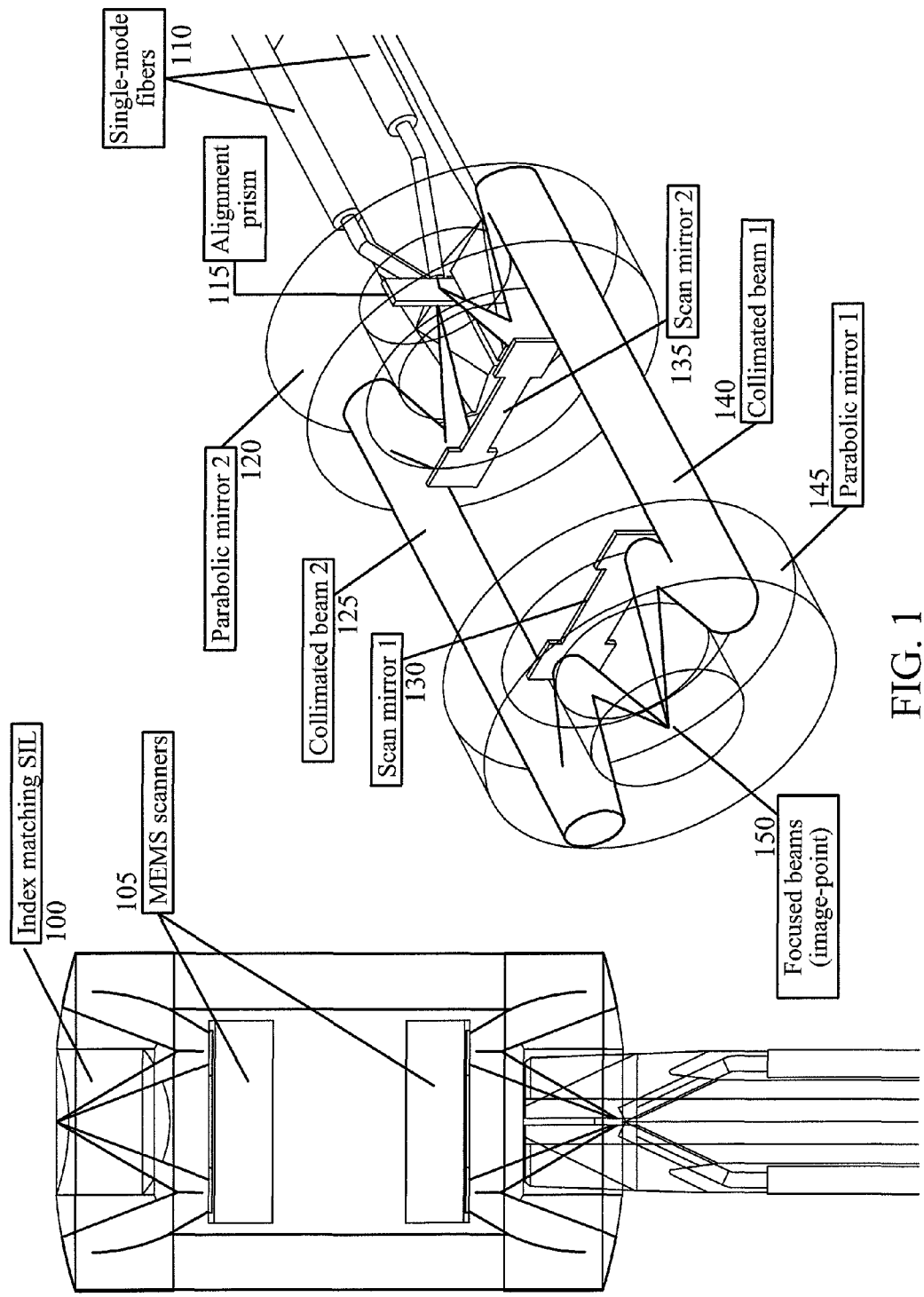
FIG. 1 shows an example embodiment of a multispectral DAC microscope consistent with the instant disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

The present invention is believed to be applicable to a variety of different types of devices, systems and methods involving confocal microscopes. While the present invention is not necessarily so limited, various aspects of the invention may be appreciated through a discussion of examples using this context.

In connection with various example embodiments, a microscope arrangement includes and/or is formed with respective scanning mirrors and light or beam-shaping mirrors (e.g., collimating mirrors) that pass collimated light between one another and respectively direct light to and from the scanning mirrors. This arrangement passes source/illumination light to a target, such as tissue in a patient, and passes image light (e.g., emitted and/or reflected from) to the target for generating an image of the target.

In certain embodiments, a multimodal interface provides an interface between the microscope arrangement and multiple tools that respectively provide different modes of target analysis. For instance, different interface devices can provide imaging characteristics for different optical imaging types (e.g., visible light and fluorescence), or for other modalities such as acoustic imaging. In some implementations, the multimodal interface interacts with an interface device to provide two or more modalities, such as for both imaging and collecting other information (e.g., acoustic) from the target region.

In more particular embodiments, the scanning mirrors include dual-axis and single-axis scanning mirrors. The dual-axis scanning mirror has two axes of movement/rotation, and re-directs light in paths to and from a first one of the beam-shaping mirrors for both illuminating and obtaining an image from the target. The first beam-shaping mirror reflects source light from the dual-axis scanning mirror to a second beam-shaping mirror in two collimated beams, and directs collimated light from the second beam-shaping mirror to the dual-axis scanning mirror. The second beam-shaping mirror redirects the collimated source light received from the first beam-shaping mirror to the single-axis scanning mirror, and directs light from the single-axis scanning mirror to the first beam-shaping mirror in two collimated beams. The single-axis scanning mirror directs light from the second beam-shaping mirror to a target, and moves along an axis to vary the working distance to the target.

In various embodiments, the respective scanning mirrors include or otherwise operate with a controller and/or actuator that moves the respective mirrors along the axes. In some implementations, each mirror is part of a silicon-based MEMS device, with the dual-axis mirror MEMS device being configured to actuate the mirror along two axes of rotation, and with the single-axis mirror MEMS device being configured for moving the mirror along an axis generally perpendicular with the target for setting the distance to the target.

The various embodiments as discussed herein can be implemented a variety of applications, such as health care, cancer research, and others, such as by replacing tissue removal, biopsies, with in vivo microscopy for detailed examination of cancerous and pre-cancerous tissues at the cellular scale in living subjects. Other aspects are directed to microscopy-assisted procedures, such as biopsies and others, which can serve to reduce the size of target areas and/or more accurately effect such procedures.

In accordance with a more particular embodiment, a light-directing apparatus includes first and second scanning mirror arrangements facing in different directions and having different scanning axes. The first scanning mirror arrangement directs source light and image light in two paths, and the second scanning directs image light from a target to the first scanning mirror. The scanning mirror arrangements operate together to scan the source light directed from the first scanning mirror arrangement and via the second scanning mirror to target locations with at least two degrees of freedom, and to direct image light from the target locations via the second scanning mirror arrangement to the first scanning mirror arrangement. In some implementations, the first and second scanning mirror arrangements collectively provide three degrees of freedom for adjusting the target location to which the source light is directed along three axes. In certain embodiments, at least one of the scanning mirror arrangements includes a mirror having two reflective sections that are respectively configured and arranged to simultaneously deflect two beams of the light to focus the two beams to the target.

In a more particular embodiment, the light-directing apparatus includes beam-shaping optics that direct light between the first and second scanning mirror arrangements and, in some implementations, collimate light for passing between the first and second scanning mirror arrangements.

Another more particular embodiment is directed to a light-directing apparatus as above, which also includes a multimodal end-piece interface that directs and receives source and image light between target locations and the second scanning mirror arrangement to provide image information, providing a first modality. The interface also acquires information from the target location, therein providing a second modality. The respective modalities may, for example, pertain to similar information (e.g., light-based), or different information such as light-based and acoustic information, as relative to a target location.

In some embodiments, the multimodal end-piece interface directs and receives the source and image light while acquiring the information in a second modality, to concurrently provide information for two modalities. In other embodiments, the first and second scanning mirror arrangements actuate in different manners based upon a type of end-piece connected to the multimodal end-piece interface.

Another example embodiment is directed to a multimodal endoscopic apparatus including a scan-engine module and a multimodal end-piece interface. The scan-engine module includes first and second scanning mirror arrangements that face different directions, as well as optics that direct light therebetween. The first scanning mirror arrangement directs source light and image light in two paths. The second scanning mirror arrangement is cooperatively arranged with the first scanning mirror arrangement to direct light received from the first scanning mirror arrangement to a target, and to direct image light from the target to the first scanning mirror arrangement. The first and second scanning mirror arrangements scan light about different scanning axes to collectively provide three degrees of freedom for scanning the target. In a more specific embodiment, the first and second scanning mirror arrangements collectively provide three degrees of freedom for scanning the target by scanning light to target locations within tissue along three different axes.

The multimodal end-piece interface operates to interface with a plurality of different end pieces to facilitate the acquisition of information for multiple modalities. In more particular embodiments, a GRIN relay lens is located in the optical path of the light and couples with different types of end-pieces connected to the multimodal end-piece interface.

In various embodiments, multimodal operation is carried out to concurrently obtain information in different modalities, such as to concurrently acquire light-based information and at least one additional type of information (e.g., acoustic or heat). In other embodiments, multimodal operation is carried out to collect two or more sets of information including light-based information, to provide information for a single modality. In a more particular embodiment, the endoscopic apparatus includes a micromachined ultrasonic transducer that applies and detects ultrasonic waves to characterize the target. This ultrasonic application can be carried out, for example, together with optical imaging and/or other modalities.

The scanning mirror arrangements are implemented in different manners, depending upon the application. In some embodiments, at least one of the scanning mirror arrangements includes a mirror having two reflective sections that simultaneously deflect two beams of the light to focus the two beams to the target. In other consistent or different embodiments, the scan-engine module actuates the scanning mirror arrangements in different manners respectively based upon a type of end-piece connected to the multimodal end-piece interface (e.g., as implemented with a controller, such as a computer-based controller that generates and output to actuate the scanning mirror arrangements).

Another example embodiment is directed to an endoscopic apparatus having single-axis and dual-axis scanning mirror arrangements as well as first and second beam-shaping mirrors. The dual-axis scanning mirror arrangement has two axes of movement and re-directs light in two paths respectively for source light and image light. The first beam-shaping mirror redirects source light from the dual-axis scanning mirror in two collimated beams, and redirects collimated light to the dual-axis scanning mirror arrangement. The second beam-shaping mirror redirects the collimated source light from the first mirror, and redirects image light to the first mirror. The single-axis scanning mirror directs the collimated light received from the second mirror to a target, directs image light from the target to the second mirror, and moves along an axis to vary the working distance to the target.

The respective scanning mirrors may be implemented in a variety of manners. In one example, the dual-axis scanning mirror includes a mirror having two reflective sections that simultaneously deflect two beams of the light to focus the two beams to the target. As another example, three degrees of freedom are facilitated with the respective scanning mirrors, for certain embodiments, by moving the single-axis scanning mirror arrangement along an axis that is perpendicular to the target to vary the working distance to the target, and/or by actuating the dual-axis scanning mirror to vary the position of the focused light such as in an x-y type direction in a plane that is perpendicular to the axis along which the single-axis scanning mirror arrangement is moved. For example, the single-axis scanning mirror arrangement can be moved along an axis that is perpendicular to the target to vary the working distance to the target according to a wavelength of the collimated light.

In some embodiments, one or both of the single-axis and dual-axis scanning mirror arrangements include a silicon-based circuit including an actuator and dual mirrors, with the actuator operating to actuate the dual mirrors along the axis to set the working distance between the single-axis scanning mirror arrangement and the target.

Various example embodiments are directed to a catadioptric endoscopic apparatus or method of manufacture that is consistent with this disclosure. Such catadioptric apparatuses or methods can be implemented with one or more embodiments herein, such as with the scanning arrangements discussed above. The catadioptric apparatus includes a first scanning mirror arrangement that directs source light and image light in two paths, and a second scanning mirror arrangement facing in a different direction than the first scanning mirror arrangement, and that directs light received from the first scanning mirror arrangement to a target and directs image light from the target to the first scanning mirror arrangement. The scanning mirror arrangements have different scanning axes, via which three degrees of freedom are provided (e.g., for focusing to a target in three-dimensional space as may be defined by an x, y and z coordinate system). The catadioptric apparatus also includes optics having catadioptric mirrors that direct light between the first and second scanning mirror arrangements, the catadioptric mirrors including at least one refractive surface and at least one of a parabolic reflecting surface and a spherical reflecting surface.

In some implementations, the catadioptric mirrors include at least one refractive surface and a spherical reflecting surface. In other implementations, the catadioptric mirrors include of at least one refractive surface and a parabolic reflecting surface. In yet another implementation, each of the catadioptric mirrors includes a reflective surface that directs most of the light incident upon the catadioptric mirror, relative to light incident upon other surfaces of the catadioptric mirror. In a further implementation, the catadioptric mirrors pass light for obtaining simultaneous fluorescence images at multiple wavelengths.

Another example embodiment is directed to an endoscopic apparatus having a narrow-field endoscope and a wide-field microscope in a housing, for concurrent narrow-field and wide-field viewing of tissue (e.g., wide-field for navigation, and narrow-field for magnification). The apparatus includes optics that direct light between the first and second scanning mirror arrangements, and that illuminate and image a region including a target area and a surrounding area that is on an order of magnitude greater in area, relative to the target area. The narrow-field endoscope includes a first scanning mirror arrangement that directs source light and image light in two paths, and a second scanning mirror arrangement that faces away from the first scanning mirror arrangement (i.e., the scanning mirror arrangements face in different directions). The second scanning mirror arrangement directs light received from the first scanning mirror arrangement to the target area, and directs image light from the target to the first scanning mirror arrangement. The first and second scanning mirror arrangements have different scanning axes, via which the scanning mirror arrangements collectively provide three degrees of freedom with respect to focusing to target locations.

In some embodiments, the wide-field microscope and the single-axis scanning mirror concurrently focus an image including the target to respectively provide a wide-field image for navigation and a focused image of the target, and the housing includes a biopsy device that removes tissue in the target area.

In accordance with various embodiments, a multimodal DAC microendoscope device includes a universal scan-engine-module that is configured to couple to (and/or includes) a multitude of multimodal end-piece-modules. The scan-engine-module includes an assembly of micro-optics and MEMS components, such as multispectral DAC microscope components as discussed herein. In some implementations, the end-piece-modules include a GRIN relay lens and a ring-shaped capacitive micromachined ultrasonic transducer (CMUT), which together provide overlapping acoustic and optical fields in the tissue being imaged or treated. These multimodal devices can be used to extend point-of-care microscopic in-vivo examination of tissue to determine the presence or extent of disease, and may additionally provide new tools for point-of-care therapeutic interventions in the clinic. These approaches may be implemented with tissue-contact applications, or non-contact imaging (e.g., for achieving wider views).

Various embodiments are directed to the integration/combination of optical and ultrasonic imaging/therapeutic modalities, and related components (e.g., optics, ultrasonic transducers, and surgical tools). Certain embodiments are directed to combinations of components to produce different types of photoacoustic imaging modalities, with optics that operate according to DAC microscopy in which illumination and collection beams provided by respective illumination and collection fibers are both confocally aligned and synchronously scanned. The multimodal DAC microendoscope platforms that can be constructed from these components provide a variety of combinations of optical and ultrasonic imaging/therapeutic modalities, such as high-resolution multispectral fluorescence microscopy, high-resolution multispectral fluorescence microscopy with deep ultrasound 3-D imaging and ultrasonic therapy/drug delivery, high-resolution multispectral fluorescence microscopy with acoustic-resolution multispectral photoacoustic imaging and ultrasonic therapy/drug delivery, high-resolution multispectral fluorescence microscopy with optical-resolution multispectral photoacoustic microscopy and ultrasonic therapy/drug delivery, non-contact wide-view multispectral fluorescence imaging, non-contact wide-view multispectral fluorescence imaging with non-contact acoustic-resolution multispectral photoacoustic imaging, and non-contact wide-view multispectral fluorescence microscopy with non-contact optical resolution multispectral photoacoustic imaging.

Various applications of the multimodal microendoscopes include use in medical procedures such as image-guided surgery applications involving the integration of microscopes as discussed herein with tools such as robotic tools and tumor suction catheters for rapid co-localized image detection and treatment. In other applications, point-of-care in-vivo microscopes are integrated with delivery platforms, such as the instrument channels in conventional endoscopes and laparoscopes, with compatibility with other endoscope designs, and with disposable attachments.

Turing now to the Figures, various aspects therein show devices and apparatuses with similar components. In this regard, reference is made to certain components in greater detail for some figures, while similar components are not necessarily addressed in view of the degree of detail in other figures and corresponding description. Beginning with FIG. 1, a multispectral DAC microscope has two parabolic reflective surfaces facing each other, and two MEMS scanners facing away from each other. A first one of the parabolic mirrors is used to focus two parallel, collimated beams to a common image-point inside tissue. The other (second) parabolic mirror directs light from a source to the first parabolic mirror in two collimated beams. A parabolic mirror #2 120 is used for first collimating the beams from two single-mode fibers 110 that are angled towards each other, and which each reflect their respective diverging beams off of a flat alignment prism 115. Also, parabolic mirror #1 145 is used to focus the beams into the tissue at a nominal depth (shown) of about 100 microns. The use of two symmetrically placed parabolic mirrors thus provides optical surfaces for collimation, alignment, and focusing of light along all the beam paths inside the microscope, and also inside the tissue. Also shown in FIG. 1 are additional components and elements of multispectral DAC microscopes, which will be discussed in further detail below. The components and elements shown in FIG. 1 are: an Index-matching SIL 100; MEMS scanners 105; single-mode fibers 110; an alignment prism 115; parabolic mirrors 120 and 145; two collimated beams 125 and 140; a scan mirror 130; and focused beams (image-point) 150.

In some embodiments, this optical design is implemented using all-reflective (or mostly-reflective) optics, to obtain simultaneous fluorescence images at multiple wavelengths, and self-aligning properties, resulting in lower-tolerance requirements for assembly of micro-components making up the microscope (e.g., MEMS, alignment prism, single-mode fibers, etc.) within the microscope package. Lower assembly tolerances facilitate construction, making the process of scaling to a smaller size more feasible.

Figure 2:
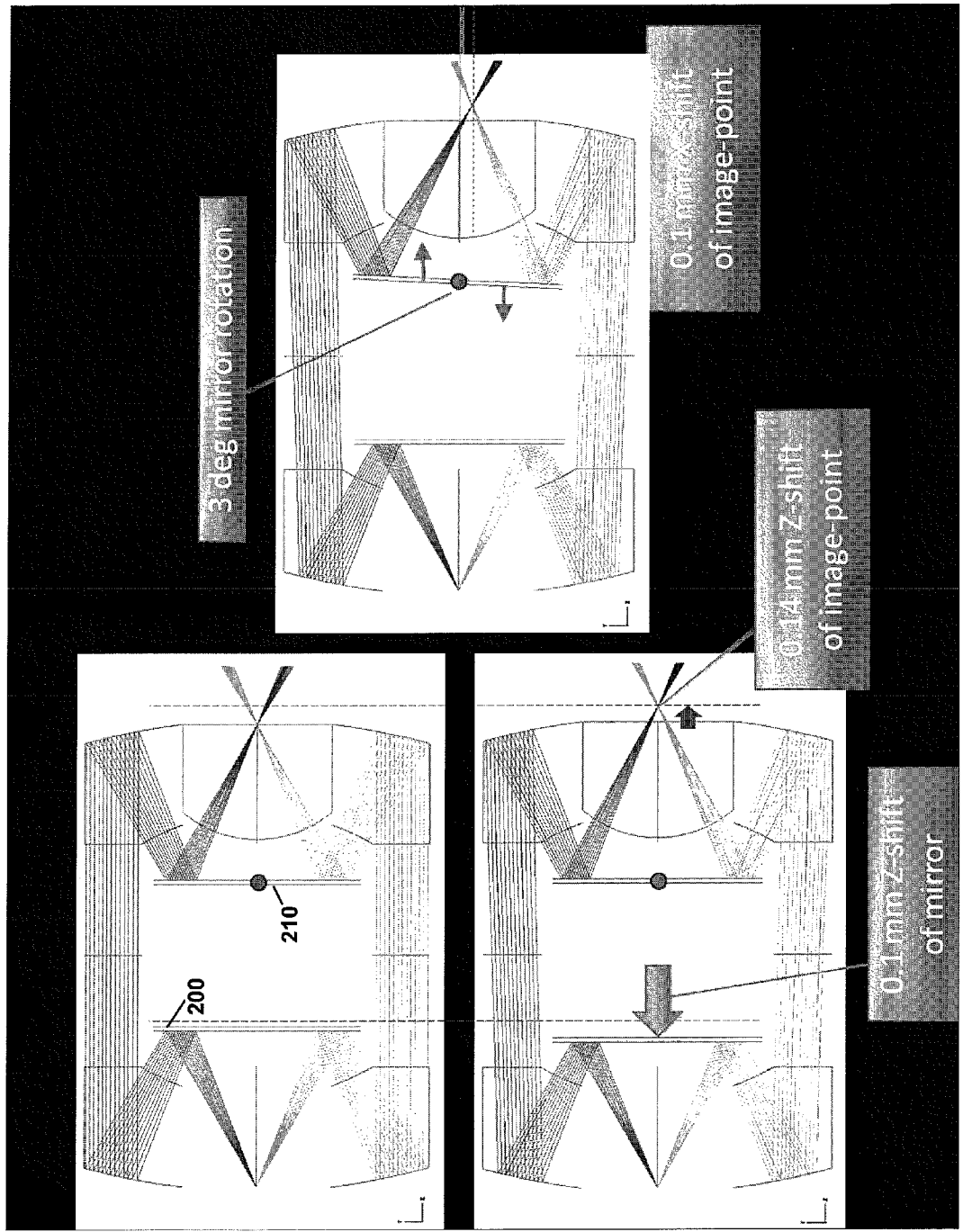
FIG. 2 shows raytrace diagrams of exemplifying aspects of a multispectral DAC microscope according to aspects of the instant disclosure.

FIG. 2 shows raytrace diagrams exemplifying aspects of a microscope such as shown in FIG. 1, and the MEMS scanners therein. The results on the left side of the figure show two different imaging depths of the beams that result from the "Z-shifting" of scan mirror #2 (200), which is specifically designed to produce fast vertical scanning of the variable working distance (WO) of the microscope. The result on the right side of the figure shows the transverse scanning of the image-point produced by a three-degree rotation of scan mirror #1 (210). By using scan mirror #2 (200) to rapidly vary the WD, the X-Y image plane produced by scan mirror #1 (210) is also scanned along the Z-direction (deeper into the tissue), thereby providing an "all-MEMS" 3-D scanning capability.

Figure 3:
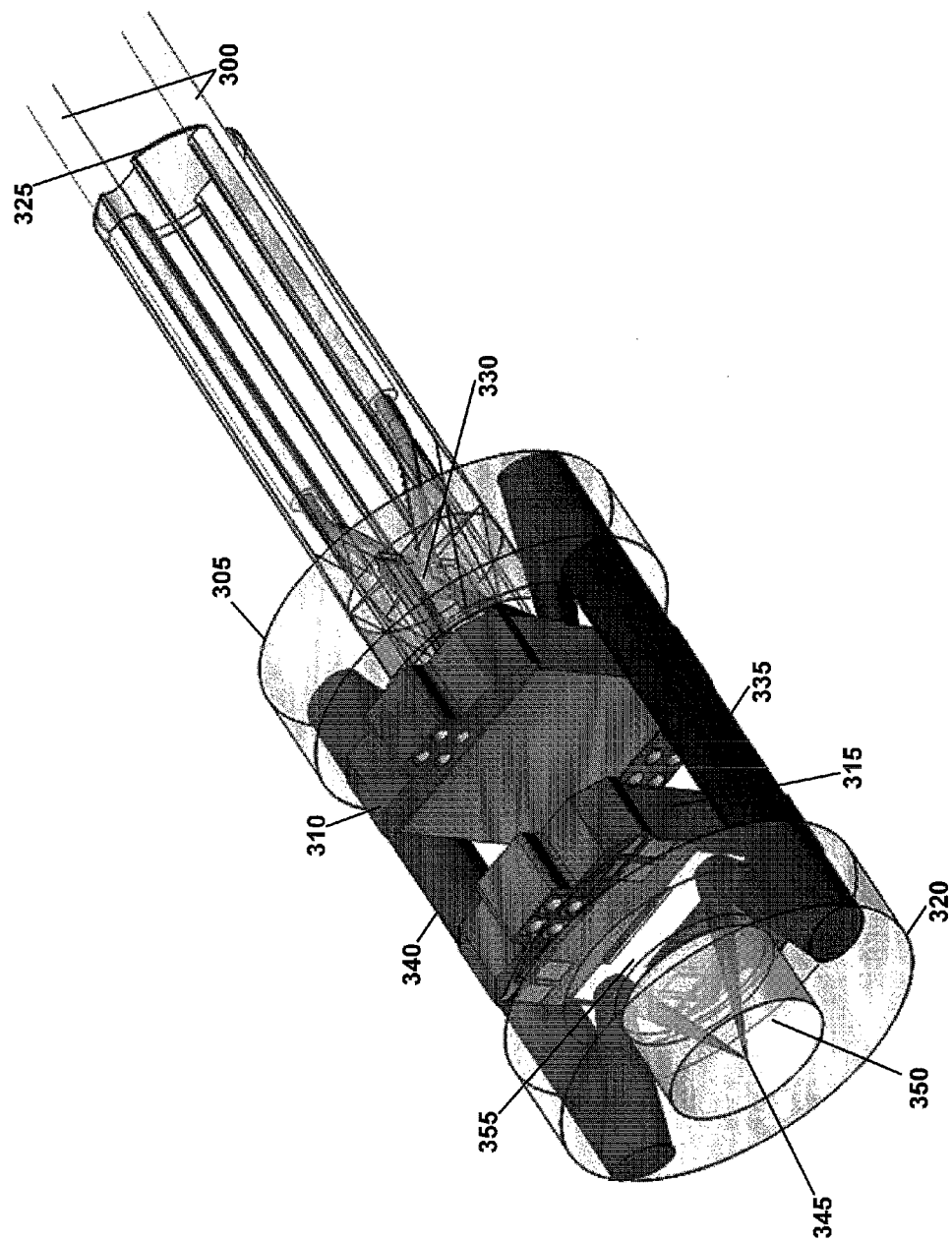
FIG. 3 shows a cut-away view of an example embodiment of a multispectral DAC microscope assembly, consistent with aspects of the disclosure.

Components of a multispectral DAC microscope assembly are shown in the two "cut-away" views in FIG. 3. These components include: two identical catadioptric optical elements 305/320 (incorporating the parabolic mirrors), two MEMS scanners 310/315 (X-Y scanner+vertical scanner), two single-mode fibers 300, a dual-fiber ferrule 325, and one flat alignment prism 330. The MEMS scanners 310/315 facilitate acquisition of a 3-D image. The 2-D lateral MEMS scanner rasters the laser beam to construct a 2-D image and the 1-D MEMS scanner adds the depth dimension. The 2-D lateral MEMS scanner and 1-D depth scanners can be co-located in the same housing to achieve volumetric imaging. The probe itself can be scaled to about 3.2 mm in diameter.

Figure 4A:
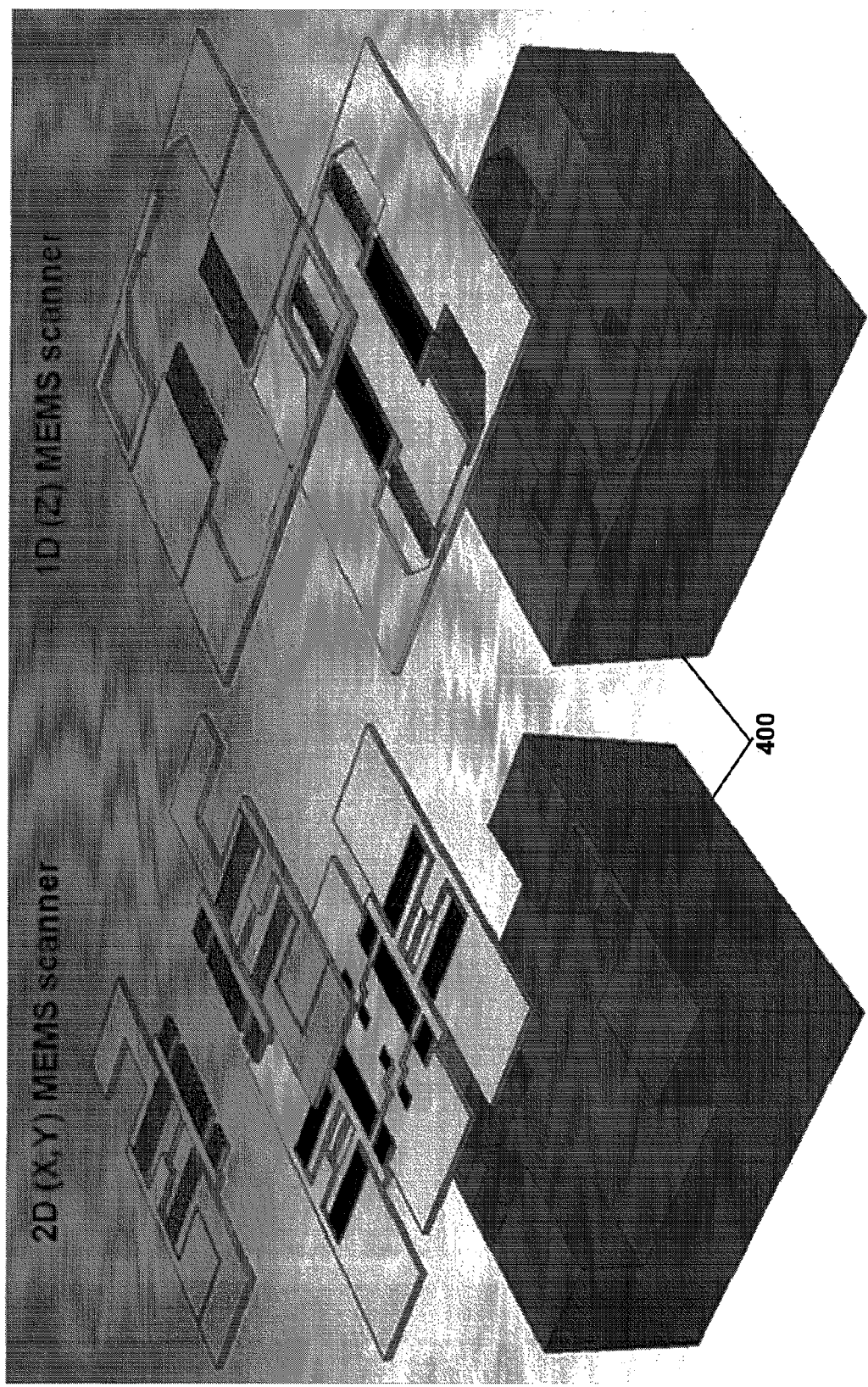
FIGS. 4A and 4B show schematic designs of 1-D and 2-D MEMS scanners implemented in accordance with various example embodiments of multispectral DAC microscopes.
Figure 4B:
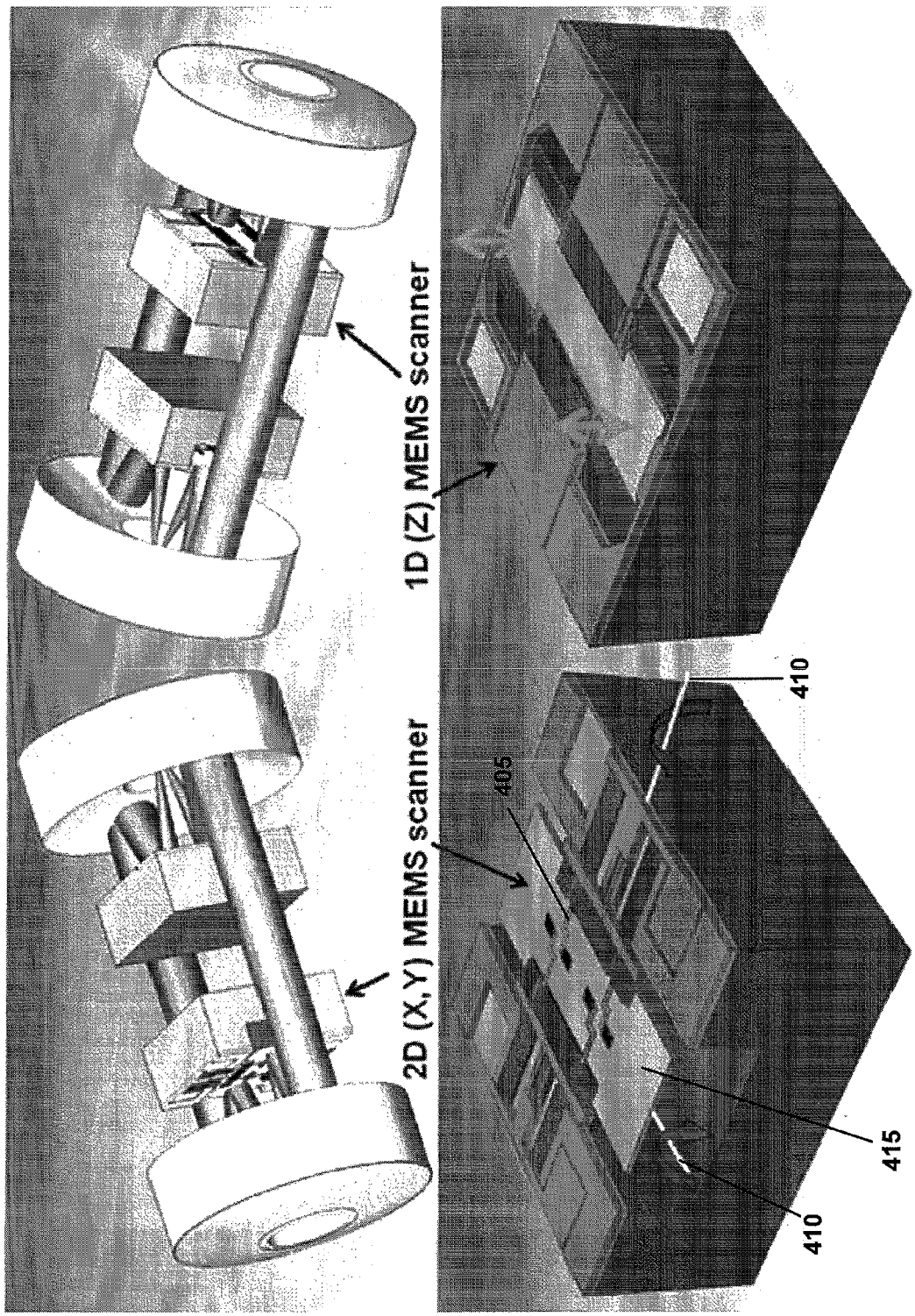

FIGS. 4A and 4B show schematic designs of MEMS scanners, which may be implemented in accordance with various example embodiments. The frame 400 can be disconnected on the two mirror sides to reduce truncation of the collimated beam within the probe, and thereby allow further reduction of the dimensions of the MEMS chip. These features facilitate diffraction-limited imaging. Anchors 405 connect the mirror 415 to the frame 400 and provide structural stability. Inner and outer springs 410 are implemented to connect the mirrors 415, using a serpentine design to minimize the torsional stiffness within the small space. In some implementations, the first two modes of the 2-D scanner can be implemented using such springs at the outer torsional and inner torsional modes with 916 Hz and 2.8 kHz, respectively, for decoupling the two orthogonal scanning modes. The optical static deflection can be limited at +/−8.00 and +/−7.20 for the outer- and inner-axis, respectively.

A 1-D vertical scanner (FIG. 4B) is held by four springs to enable stable up-and-down motion. The serpentine spring is used to achieve compliant deflection in z-direction. In some implementations, the dominant mode of the 1-D scanner is an up-and-down piston mode at 1.61 kHz with a Q-factor of 10, and well-separated from the second mode. A (e.g., maximum) stable deflection range of 20 um in static mode can be extended to 200 um when operated at resonance. Stable vertical scanning at video rates is possible at resonance. Operating 2-D lateral and 1-D vertical scanners simultaneously, 3-D images can be constructed by rendering multiple depth-plane images at the target spot. In some implementations, this approach is combined with image mosaicing to volumetrically image large tissue volumes.

FIGS. 5a-5f show a fabrication process for MEMS scanners, in accordance with other example embodiments. Both 2-D lateral and 1-D depth scanners can be fabricated using the same process. At FIG. 5a, a deep reactive ion etching (DRIE) approach is used to form a deep trench in single-crystal silicon 500. In FIG. 5b, respective layers of thermal oxide 510 and single crystal silicon 500 are formed as shown, in respective thermal oxidation, fusion, bonding, grinding and polishing steps. At FIG. 5c, a low-temperature oxide 520 has been formed on single-crystalline silicon 500, using self-alignment mask patterning with low-temperature oxide. At FIG. 5d, the low-temperature oxide 520 has been partially etched. At FIG. 5e, another DRIE approach is used to remove a portion of the single-crystal silicon 500, with a plasma oxide etch that uses the low-temperature oxide as a mask. At FIG. 5f, another DRIE approach is used to remove a further portion of the single-crystal silicon 500, which is followed by plasma oxide etching.

Figure 5:
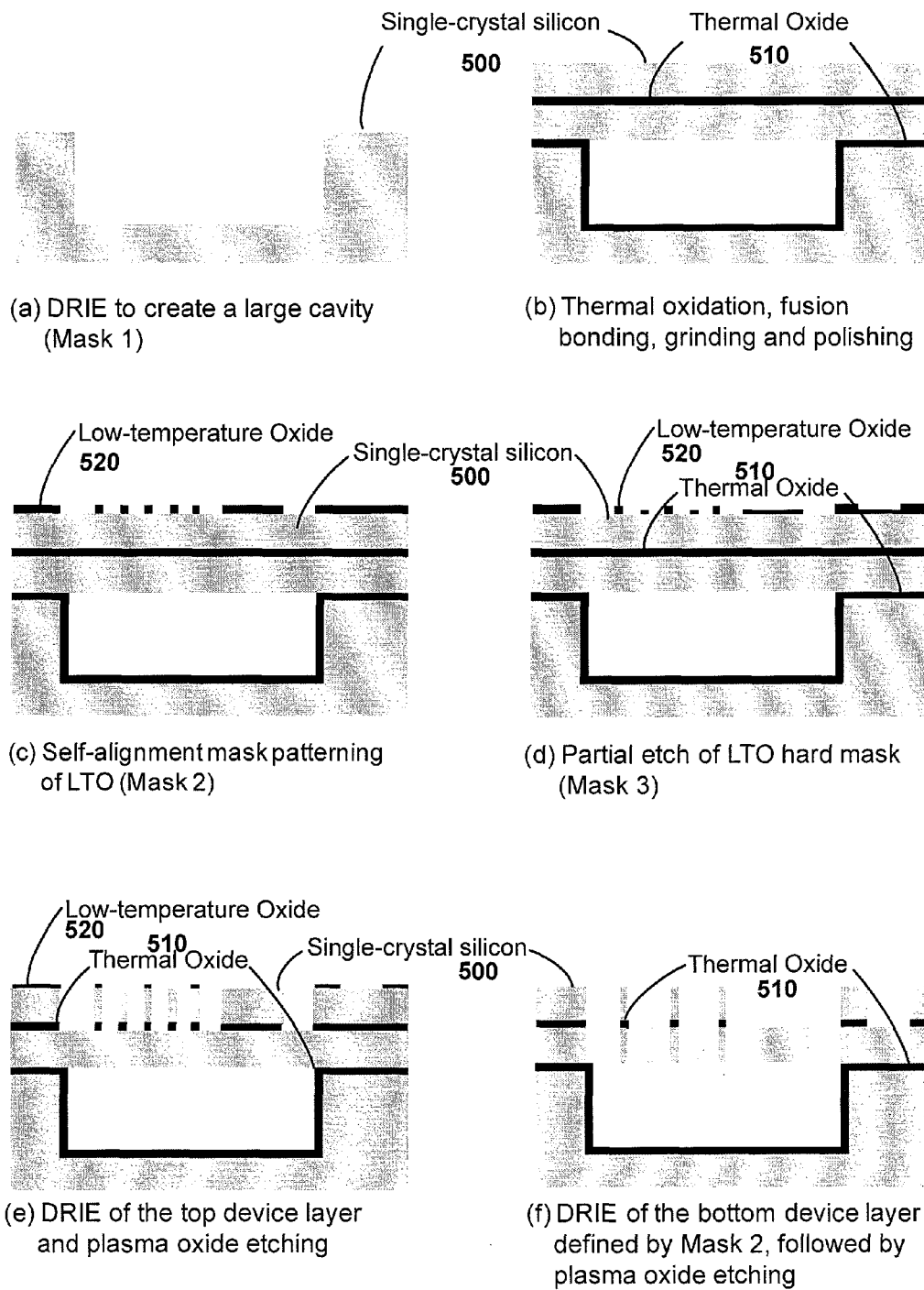
FIGS. 5a-5f show various steps in a fabrication process for MEMS scanners, in accordance with the instant disclosure.

In some implementations, the wafer as shown in FIG. 5 is protected by thick photoresist layers while the backside is bonded to another wafer (e.g., by clear wax). Since there is a supporting carrier wafer on the backside, a dicing saw can be used to cut through the entire device substrate, and chips can be removed from the carrier wafer (e.g., by melting the wax) without introducing mechanical shock. In some implementations, higher than 90% reflectivity for 488 nm and 785 nm wavelengths is achieved by metallizing the entire wafer using shadow masks that precisely coat only the reflecting mirror surfaces.

Figure 6:
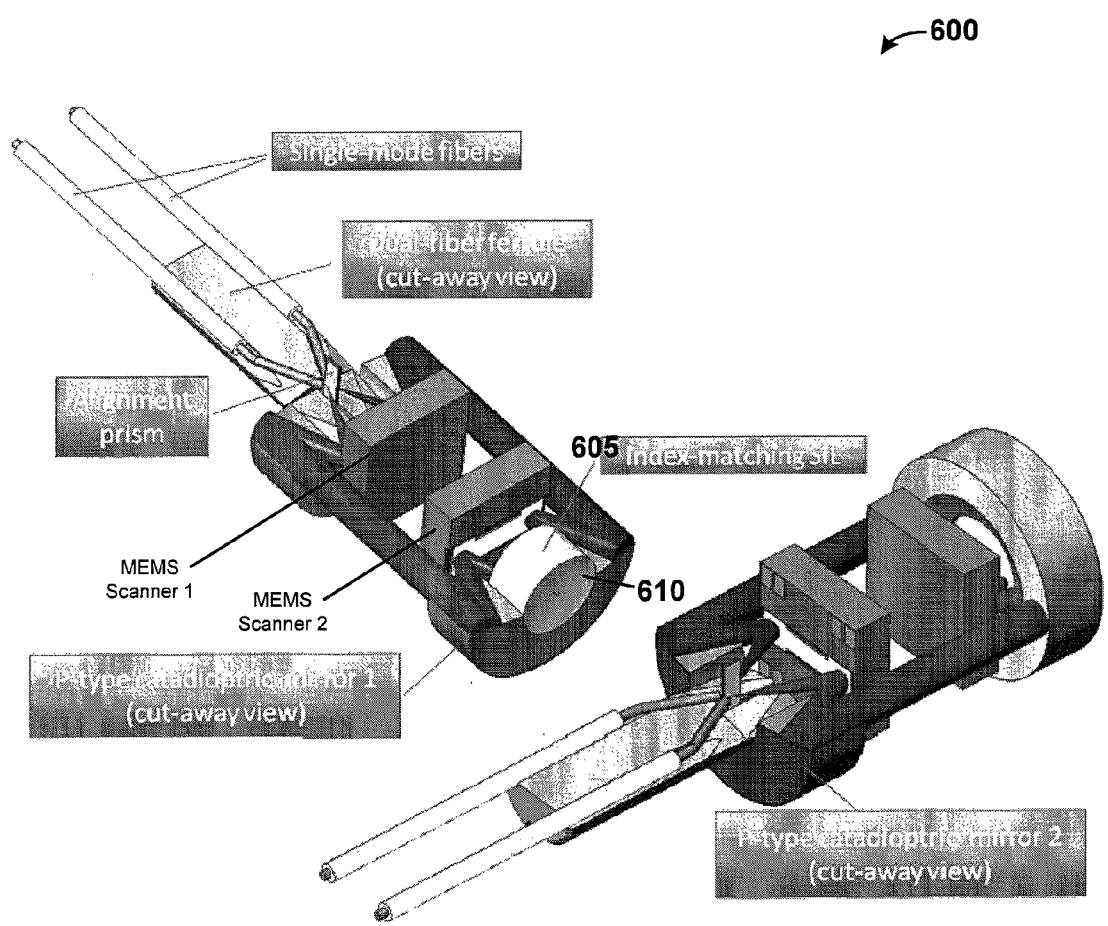
FIG. 6 shows an example multispectral DAC microscope assembly including a hemispherical solid immersion lens, in accordance with embodiments of the instant disclosure.

In accordance with another embodiment, FIG. 6 shows a microscope/endoscope arrangement 600 including a hemispherical solid immersion lens (Index-matching SIL) 605 having a refractive index that approximately matches the index of tissue, for use with a microscope arrangement as discussed herein. During imaging, the flat side 610 of this hemispherical output window is placed against the tissue to be examined and thus provides an index-matched optical interface for transmission of the focused beams into the tissue. This element improves the imaging resolution by minimizing optical aberrations that can occur at the tissue interface.

In various implementations, a DAC microscope as discussed herein includes a housing having a diameter of less than about 3.2 mm, which makes the instrument compatible for use in a 3.7 mm instrument channel such as found in many standard medical endoscopes, such as the Olympus endoscopes listed in Table 1. A microscope with this form factor would thus be configured for use with these endoscopes for performing high-resolution confocal microscopy without any modification to the endoscope.

TABLE 1

Olympus endoscopes having 3.7-mm (or larger) diameter instrument channel.

| Gastroscopes: | Duodenoscopes: | Sigmoidoscopes: | Colonoscopes: | Ultrasonic Videoscopes: |
|---|---|---|---|---|
| GIF-1TQ160 | TJF-160VR | CF-Q160S | CF-H180AI/L | GF-UCT140-AL5 |
| GIF-2TQ160 | TJF-145 | | CF-Q180AI/L | GF-UCT160-OL5 |
| GIF-XTQ160 | TJF-30 | | CF-2T160AI/L | |
| GIF-1T30 | | | CF-Q160ZI/L | |
| GIF-XT30 | | | CF-H180DI/L | |
| GIF-2T20 | | | CF-Q160DI/L | |
| | | | CFQ165I/L | |
| | | | CF-1T140I/L | |

Figure 7:
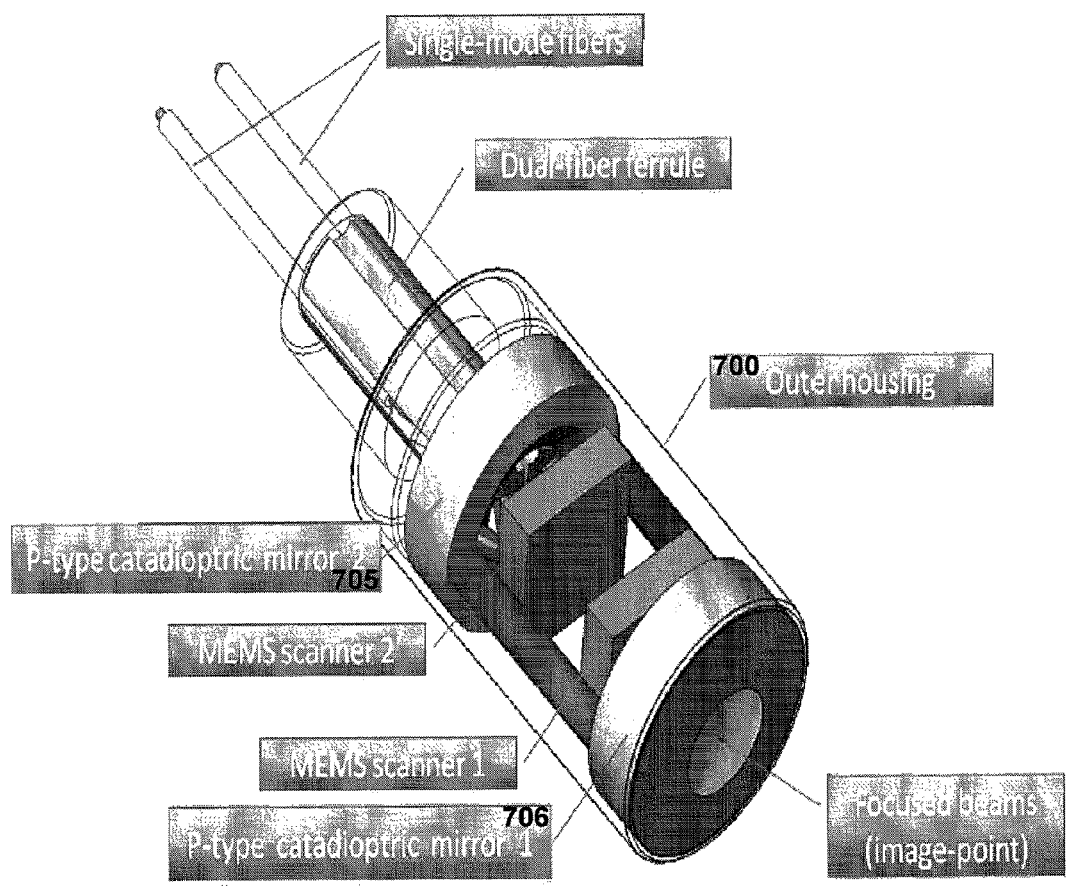
FIG. 7 shows an example multispectral DAC component assembly inside a sealed mechanical package, based on aspects of the instant disclosure.
Figure 8:
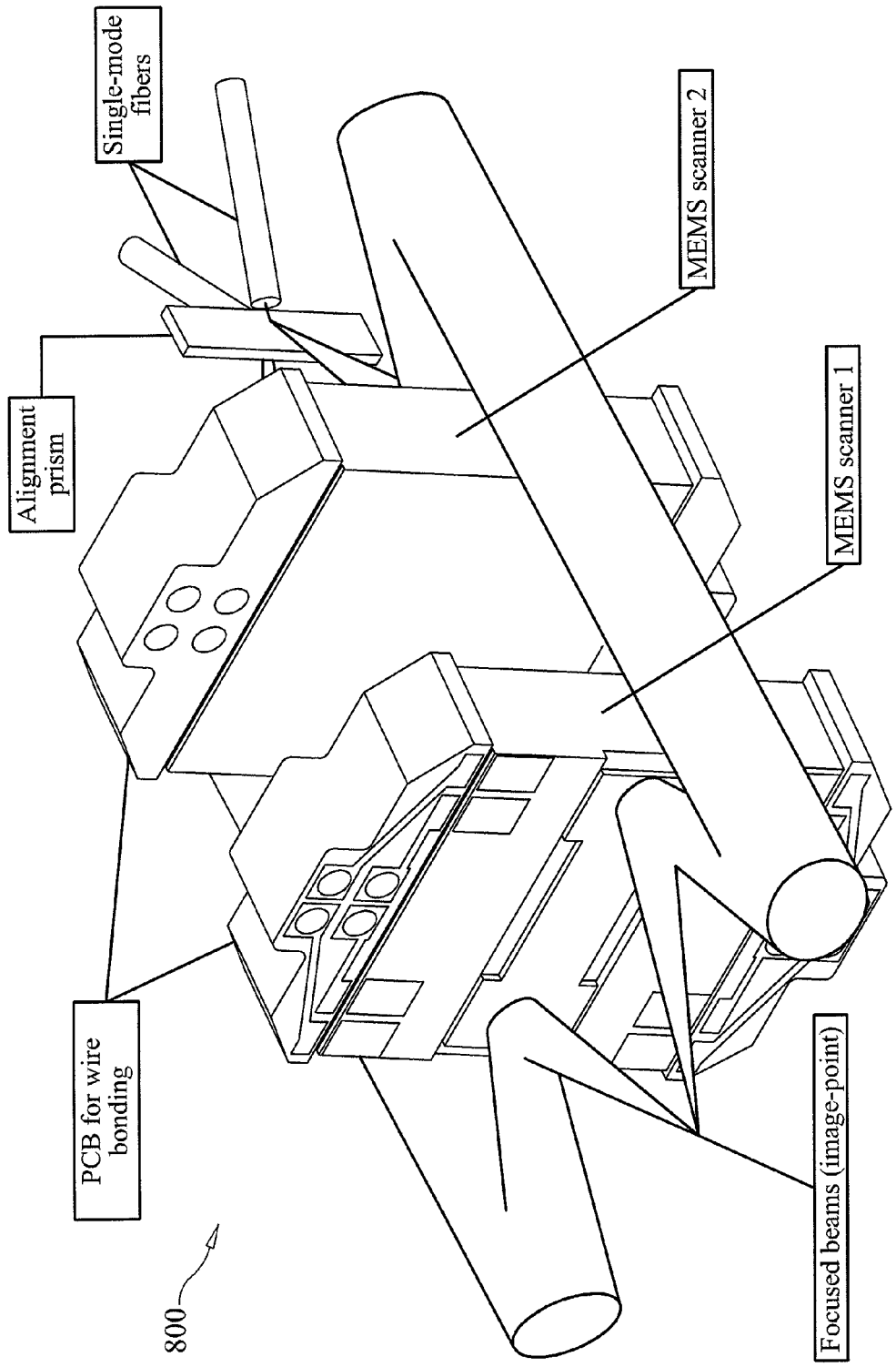
FIG. 8 shows an "all-MEMS" 3-D scanning system, in accordance with aspects of the instant disclosure.

FIG. 7 shows the assembly of microscope components positioned inside a sealed mechanical package comprising a stainless steel outer cylindrical housing 700. The package is designed to locate two parabolic mirrors 705 and 706, which are facing each other, to within required mechanical tolerances to suite particular applications, which can be determined by raytrace simulations of the final optical design. This design provides a construction that is self-aligning during its assembly, and resistive/insensitive to misalignments that may occur during use, which can facilitate high reliability during operation. In some implementations, the parabolic mirrors 705 and 706, which can be incorporated into glass (or molded plastic) and/or as catadioptric mirrors, are mounted and sealed at each end of a stainless steel housing 700, providing a rugged construction. Where catadioptric mirrors are used, their achromatic optical properties can be used to provide a multispectral DAC microscope that is more versatile for in vivo imaging applications in the clinic and medical research. In some embodiments, an all-MEMS 3-D scanning system 800 as shown in FIG. 8 can be used (e.g., to achieve higher-speed and smaller size offered by MEMS devices).

Various embodiments are directed to devices as discussed above and/or shown in the above-referenced patent document (Ser. No. 61/446,423), and including Appendix A therein, which forms part of the application, to provide multispectral optical design and analysis for MEMS-based fiber optic DAC microscope that facilitates miniaturization for endoscopic in vivo imaging of tissues, and scaling to smaller dimensions for use as a micro-endoscope and/or implantable device. This design can be implemented with low NA optics, making it easier to miniaturize, and provides a significant improvement in dynamic range.

Figure 9:
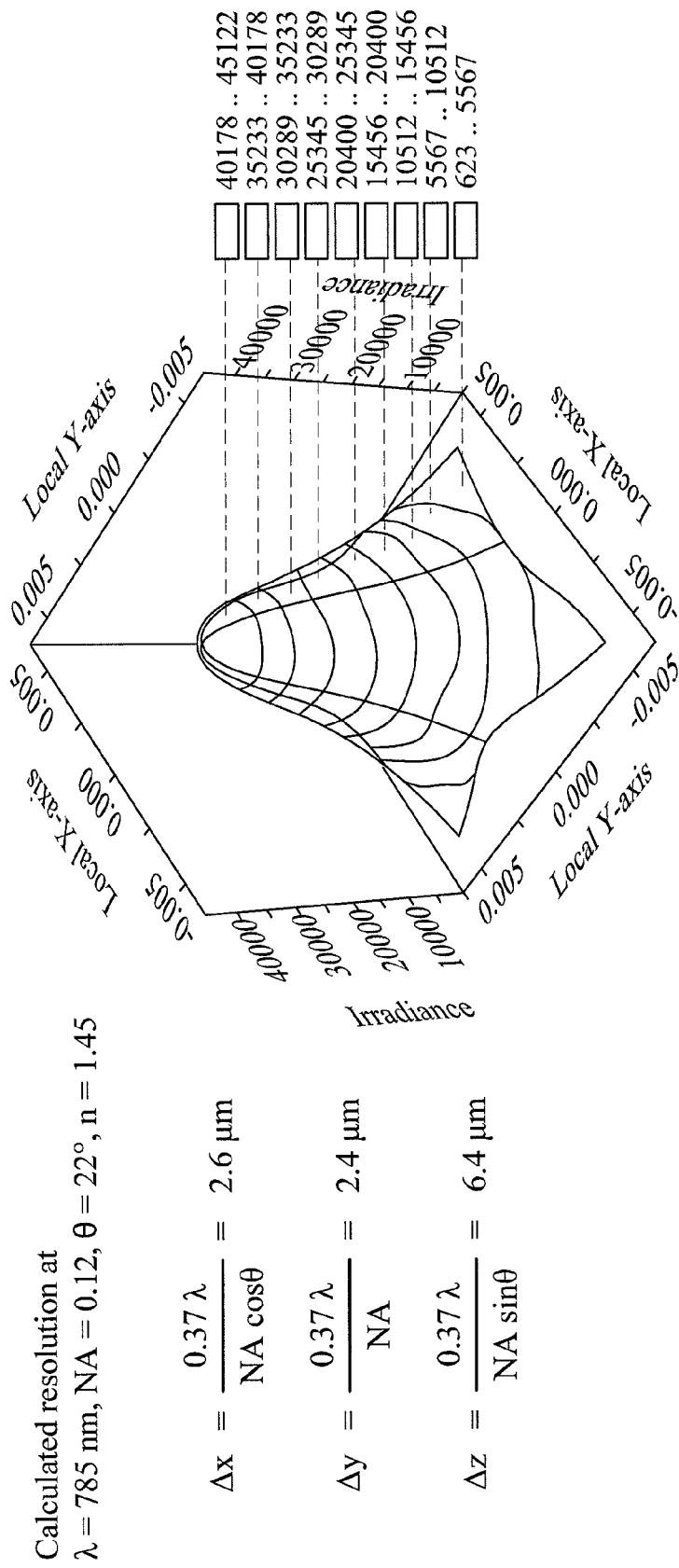
FIG. 9 shows 3-D resolution of an example embodiment of a multispectral DAC microscope based on aspects of the instant disclosure.
Figure 10:
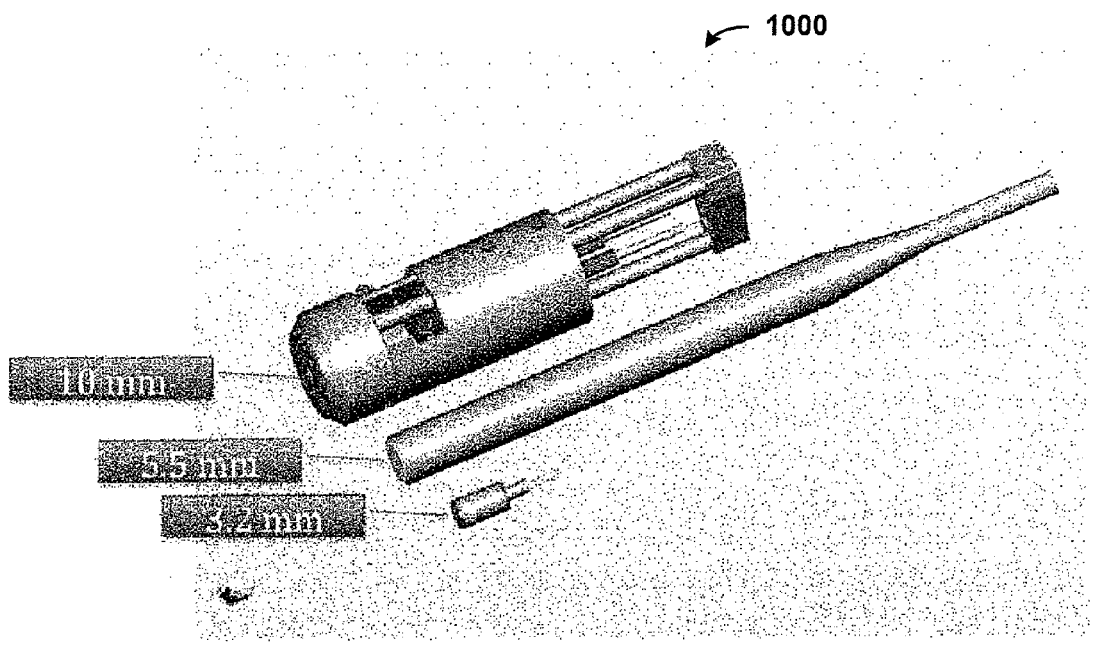
FIG. 10 shows three MEMS-based DAC microscope packages, in accordance with aspects of the instant disclosure.

FIG. 9 shows example full-width-half-maximum (FWHM) values of the 3-D resolution of a 3.2 mm multispectral DAC microscope produced from the intersection of the two relatively low-NA beams, in accordance with various example embodiments. The extent of a single volumetric resel (voxel) that is in the tissue is a cylindrical volume element having 2.5 microns radius and 6.4 microns length, thus resulting in a voxel volume of 125 microns. Depending upon the dye concentration, this volume of tissue contains a certain number N of fluorescent dye molecules that contribute to the fluorescence signal emanating from a single voxel as the excitation beam is scanned through the tissue volume. Bright fluorescence images are obtained with high contrast using miniature form factor DAC microscopes (e.g., 5.5 mm and 10 mm) and similar low-NA illumination and collection beams. In some embodiments, a 3.2 mm OD microscope as discussed herein is assembled using active alignment techniques for constructing our 10 mm and 5.5 mm form factor DAC microscopes, in accordance with the device 1000 in FIG. 10.

In some implementations, an all-reflective type of achromatic device as discussed herein can be used to obtain multispectral fluorescence images from an illumination beam comprising different excitation wavelengths. Different images produced by different respective wavelengths are spatially co-registered to each other within the tissue. Table 2 shows example characteristics exhibited with 3.2 mm multispectral DAC microscopes as discussed herein.

TABLE 2

Comparison of specifications between a DAC microscrope and other confocal microscopes

| | Diameter | Resolution | Speed | Field of view | Imaging depth | Wavelength |
|---|---|---|---|---|---|---|
| Pentax/ Optiscan ISC-1000 | 6 mm, integrated into custom endoscope | 0.7 µm lateral; 7 µm axial | ~1 fps | 500 x 500 µm | 0-200 µm adjustable | 488 nm |
| Mauna Kea Technologies, Cellvizio® GI | 2.5 mm, flexible fiber | 3.5 µm lateral; 15 µm axial | 12 fps | 600 µm | 0-120 µm fixed depth | 488 or 600 nm |
| Dual-axis confocal microscope design goal | 3.2 mm, flexible fiber | 3 µm lateral; 6 µm axial | 12 fps | 500 x 500 µm | 0-500 µm adjustable | 488-785 nm multispectral |

The microscopes as discussed herein can be used for a variety of purposes, including reaching inside the body to interrogate disease states at the cellular level, to change the diagnostic paradigm from biopsy and conventional histopathology to one of point-of-care in vivo microscopy coupled with computed image analysis.

Figure 11:
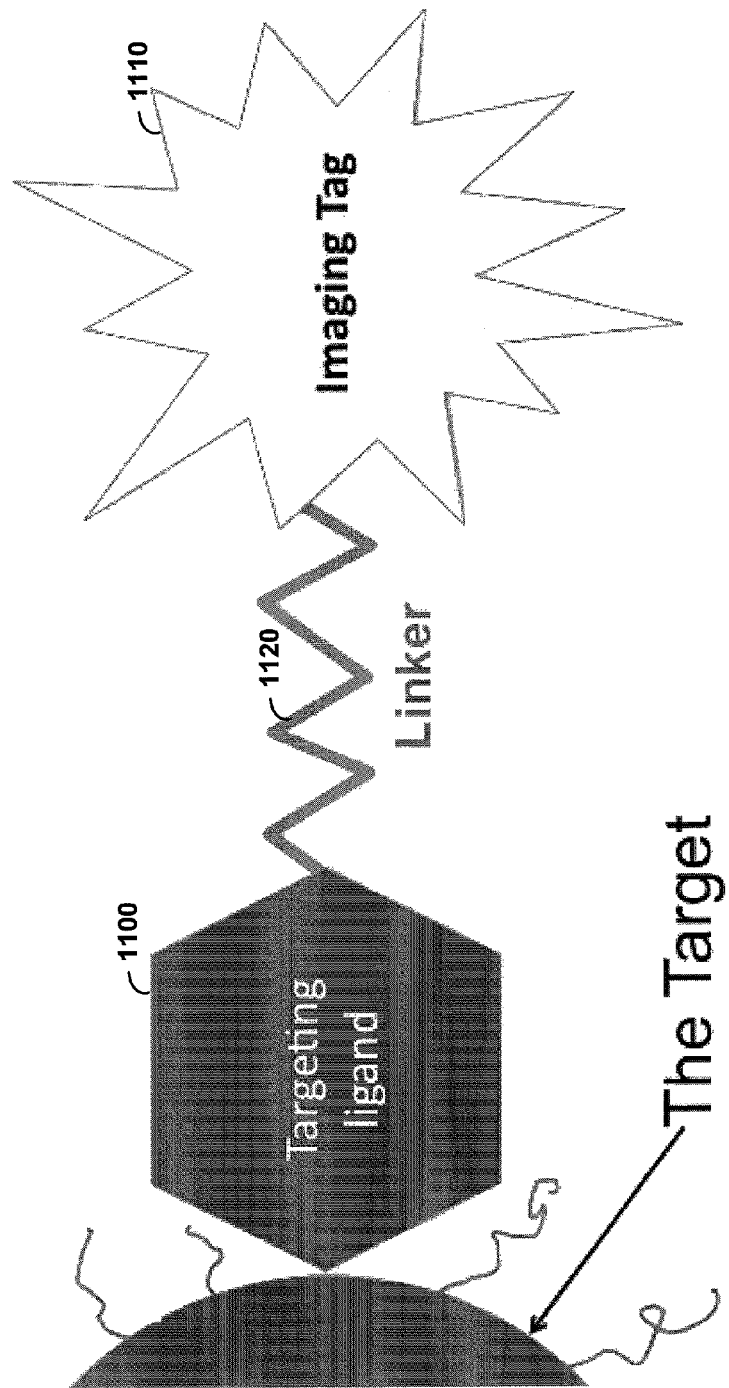
FIG. 11 shows an example illustration of a targeted multimodal contrast agent that can be constructed for use in both fluorescence and photoacoustic imaging of tissues with multimodal DAC microendoscopes, consistent with example embodiments of the instant disclosure.

FIG. 11 shows an example targeted multimodal contrast agent constructed for use in both fluorescence and photoacoustic imaging of tissues with a multimodal DAC microendoscope, in accordance with an example embodiment. A targeting ligand 1100 is connected to an imaging tag 1110 via a linking component 1120.

Figure 12:
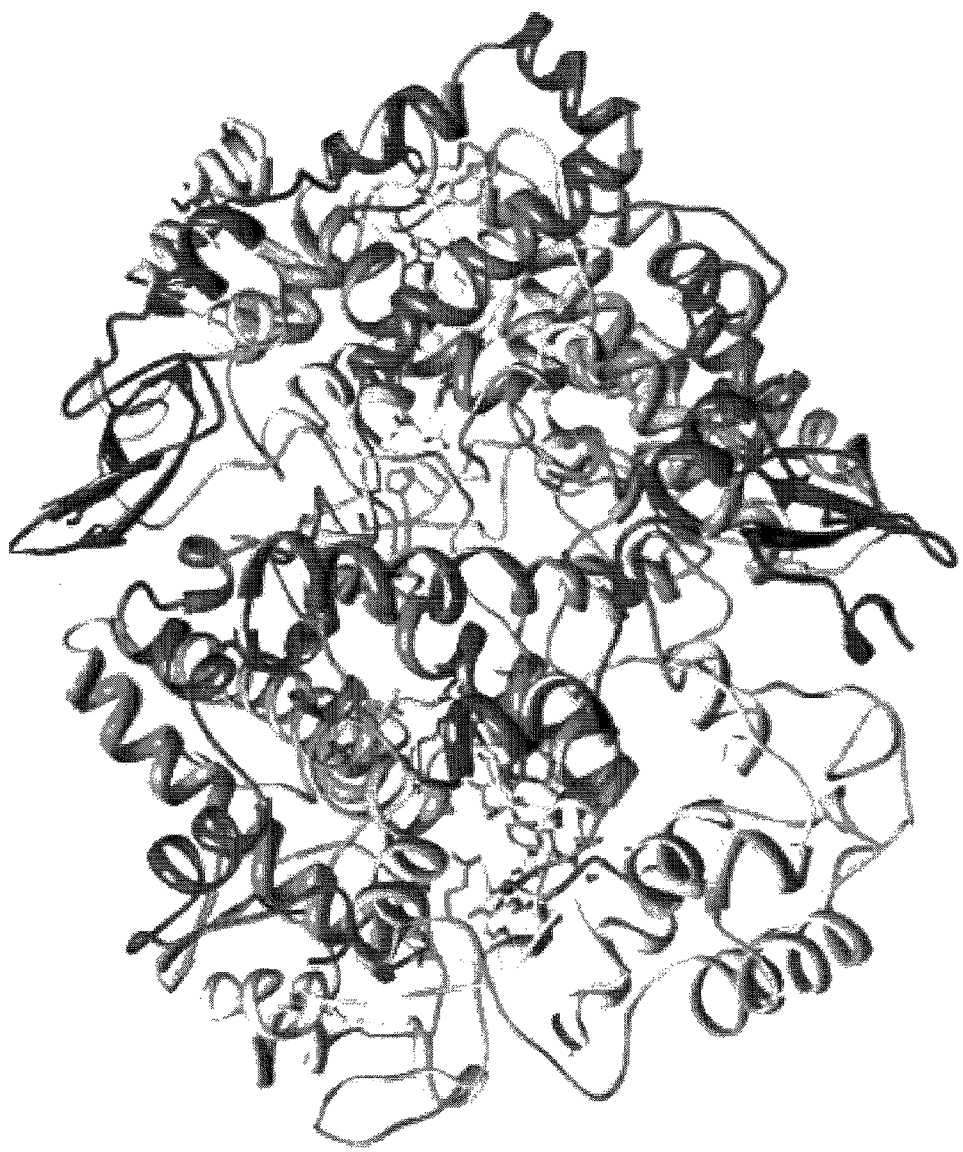
FIG. 12 shows a target for developing a multimodal contrast agent, consistent with the instant disclosure.

FIG. 12 shows a topological folded molecular configuration of the Cox-2 enzyme, which is used with certain embodiments as a specific target for developing a multimodal (fluorescent/photoacoustic) contrast agent for use in imaging tissues with a multimodal DAC microendoscope, in accordance with another example embodiment.

Figure 13:
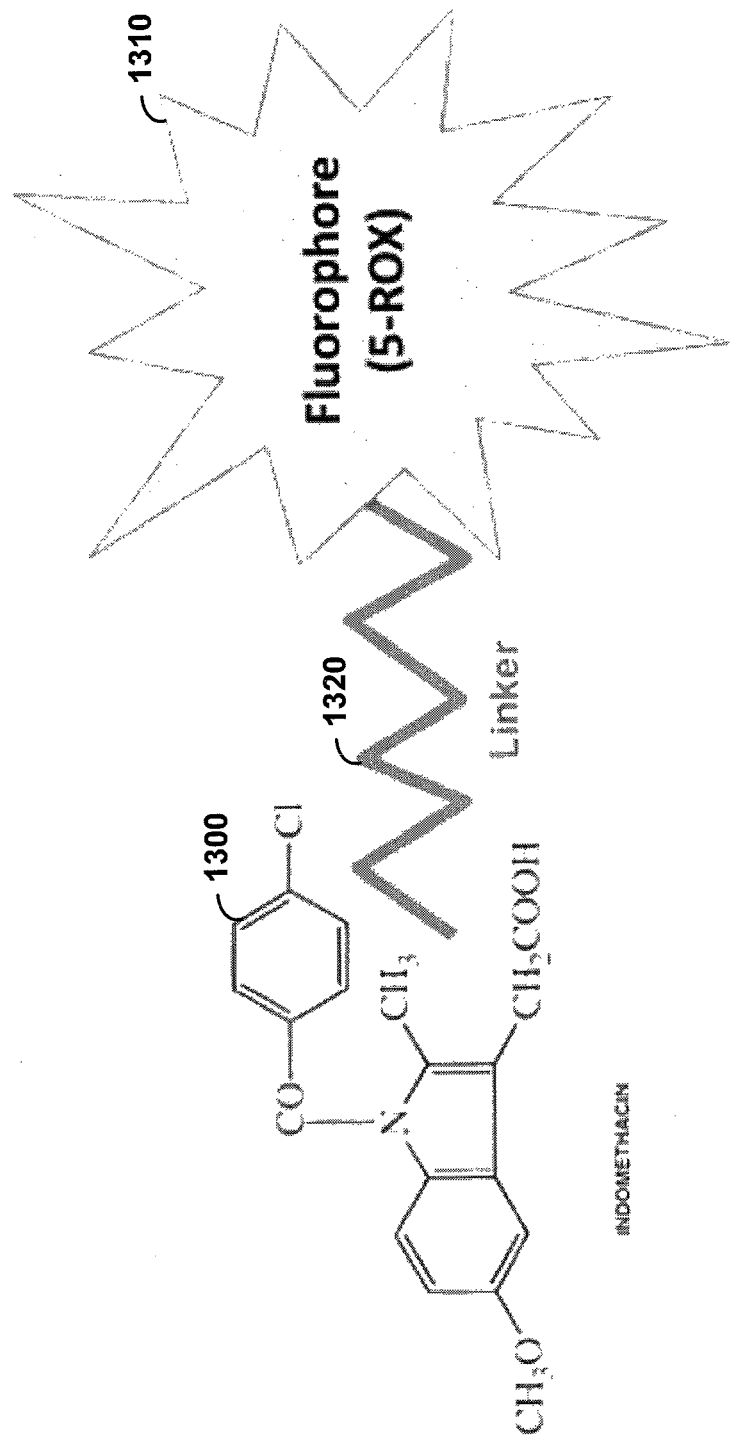
FIG. 13 shows a targeting ligand and imaging tag for a multimodal contrast agent, consistent with example embodiments of the instant disclosure.

FIG. 13 shows a targeting ligand (indomethacin) 1300 and an imaging tag (5-ROX) 1310 connected via a linker 1320, which are used to construct a multimodal (fluorescent/ photoacoustic) contrast agent for use in imaging tissues with a multimodal DAC microendoscope, in accordance with another example embodiment.

Figure 14:
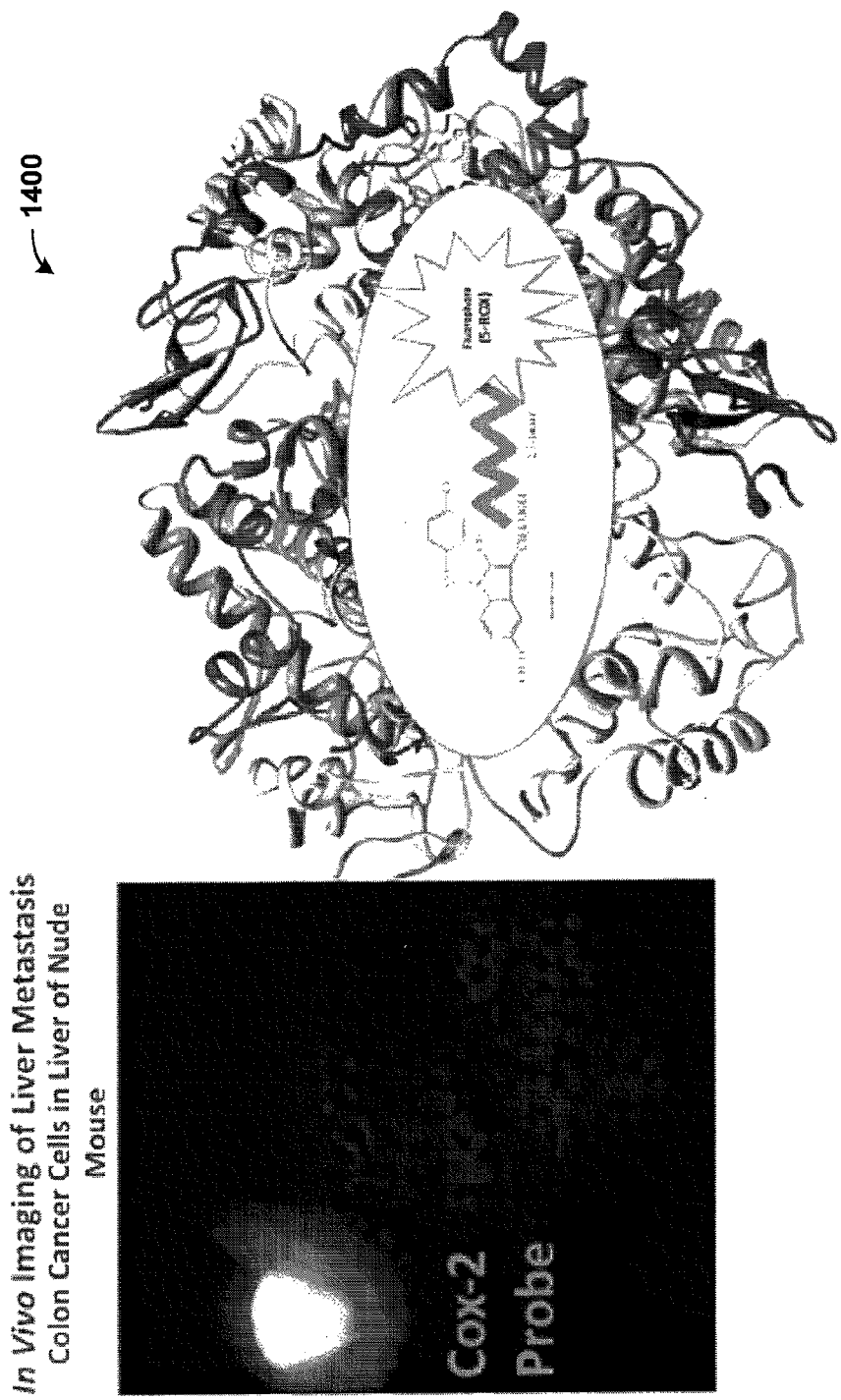
FIG. 14 shows an example targeted fluorescent contrast agent for photoacoustic imaging, consistent with example embodiments of the instant disclosure.

FIG. 14 illustrates another example targeted fluorescent contrast agent 1400 that is Cox-2-specific using the "5-ROX" fluorophore, and can be used as both a fluorophore for fluorescence imaging and a chromophore for photoacoustic imaging of tissues using various multimodal DAC microendoscope platforms, in accordance with another example embodiment. This molecular optical imaging probe can be used to detect the early stages of gastric cancer.

Figure 15:
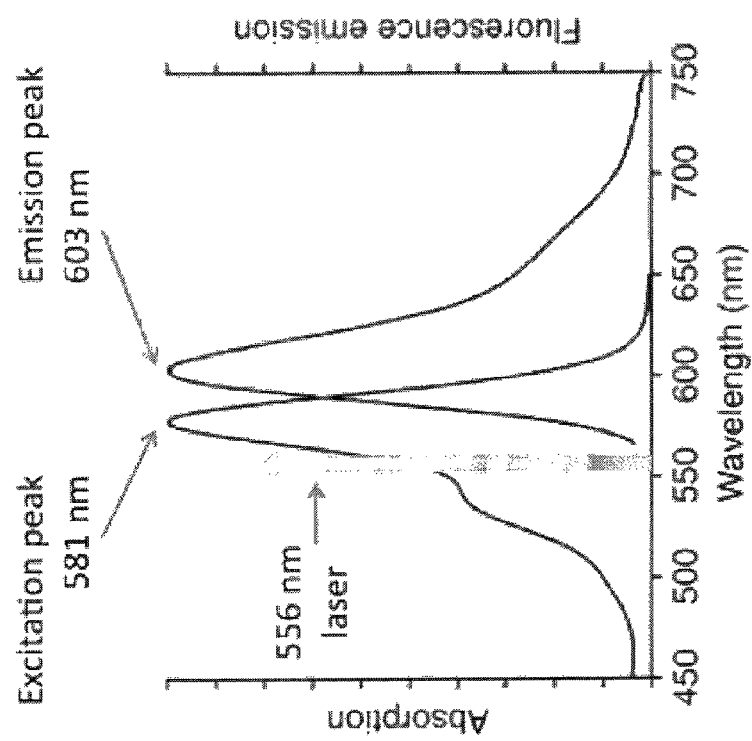
FIG. 15 shows the optical excitation and emission spectra for 5-ROX fluorophore.

FIG. 15 shows the optical excitation and emission spectra for 5-ROX fluorophore, with a peak optical absorption at 581 nm and a peak optical emission at 603 nm, in accordance with another example embodiment. Also shown in this spectra is the laser line at a wavelength of 556 nm, which is used for fluorescence imaging of the COX-2 probe and which allows separation between the illumination and collections wavelengths for sufficient filtering of the excitation light at the detection end of the system to achieve a high signal to noise ratio.

Figure 16:
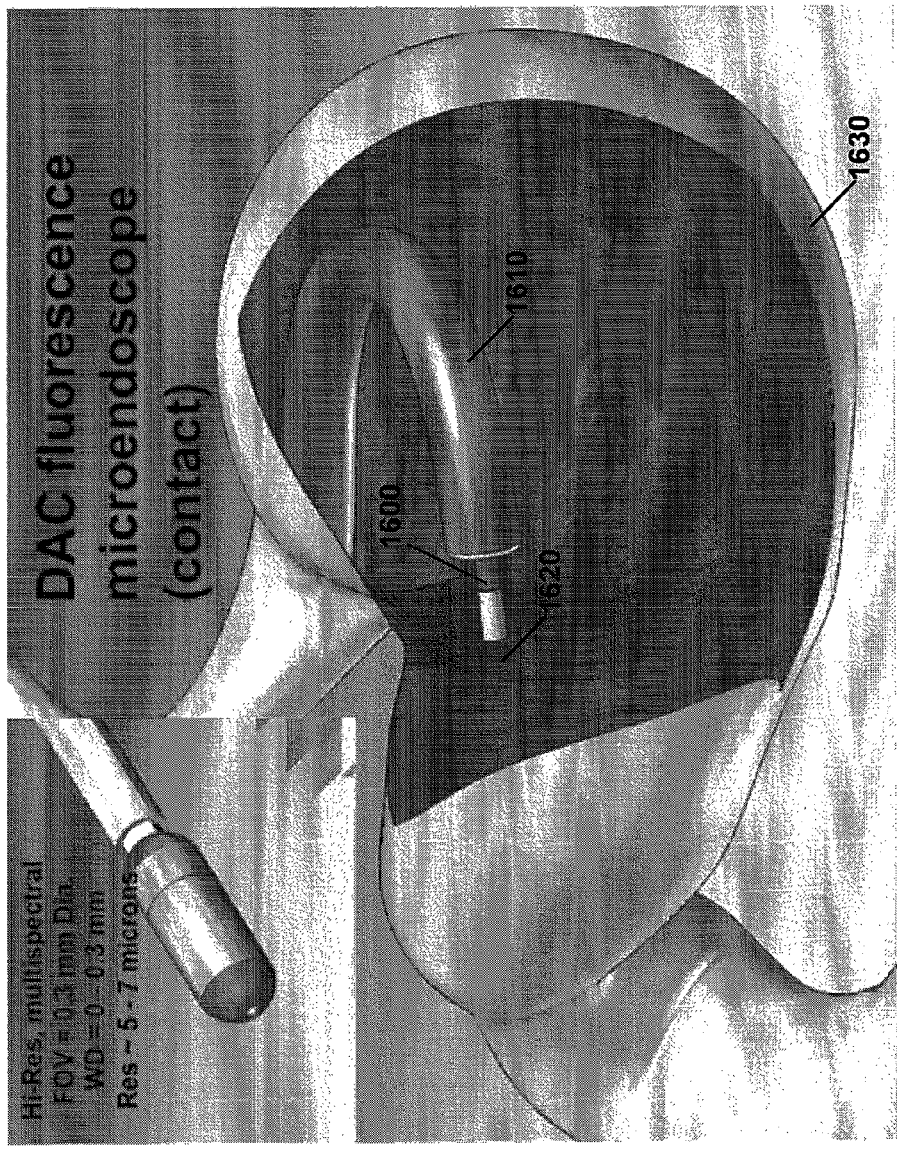
FIG. 16 shows an example embodiment in which a high-resolution DAC fluorescence microendoscope is packaged to fit into a 3.7 mm I.D. instrument channel of a GI endoscope.

FIG. 16 illustrates an example embodiment in which a high-resolution DAC fluorescence microendoscope 1600 is packaged to fit into a 3.7 mm I.D. instrument channel of a GI endoscope 1610 to be used for high-resolution fluorescence imaging when in-contact with the tissues 1620 of the stomach 1630.

Figure 17:
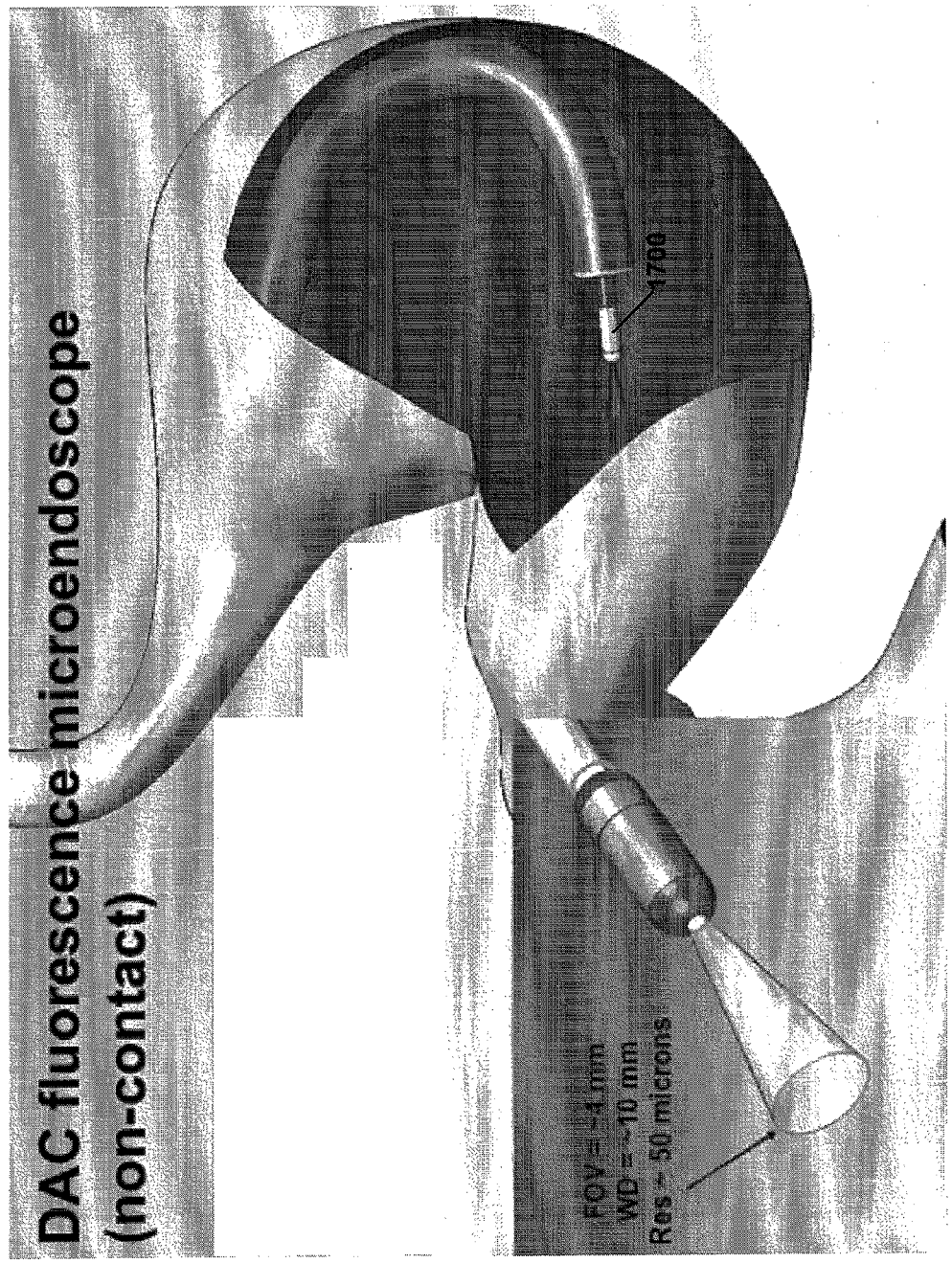
FIG. 17 shows an example utilization of a "wide-view" fluorescence DAC microendoscope of the "non-contact" type, in accordance with example embodiments of the instant disclosure.

FIG. 17 illustrates an example of how a "wide-view" fluorescence DAC microendoscope 1700 of the "non-contact" type is used for screening or guiding applications when configured for non-contact fluorescence imaging of the internal tissues of the stomach. The non-contact imaging mode has a long working distance, which enables the instrument to achieve a wider field-of-view at a corresponding lower resolution to help find the locations where the COX-2 fluorescent probe is mostly concentrated and thereby can be used for surveying large areas of tissue for suspicious locations where cells are exhibiting early stages of cancer. The microendoscope 1700 can be implemented with multiple spectra (e.g., 488-800 nm), with a field of view of about 4 mm.

Figure 18:
FIG. 18 shows an example embodiment with a dual-channel endoscope used with two different DAC fluorescence microendoscopes in a multimodal configuration.

FIG. 18 illustrates another example embodiment with a dual-channel endoscope 1800 used with two different DAC fluorescence microendoscopes in a multimodal configuration. In this example, a "wide-view" DAC fluorescence microendoscope of the "non-contact" type 1810 is used in conjunction with a high-resolution DAC fluorescence microendoscope of the "tissue-contact" type 1820. The combination of imaging modalities are used simultaneously for effective guiding of the placement of the high-resolution microendoscope to the locations where the COX-2 fluorescent probe in the tissue is observed within the wide-view fluorescence images while the tissue surface is surveyed.

Ultrasound and optical modalities are combined in a multimodal microendoscopic platform in a variety of manners. The following discussion characterizes one or more of these embodiments, with specific applicability to high-resolution multispectral fluorescence microscopy with deep ultrasound imaging and ultrasonic therapy/drug delivery. In this example, an annular ring-shaped forward-looking ultrasound transducer array is integrated on the tip of the microendoscope to provide real-time 3-D images in the same direction as the microendoscope's optical field-of-view. This approach enables a synergistic combination of ultrasonic and optical imaging modalities. Ultrasound provides greater depth of penetration (2-3 cm) with moderate resolution (~100 μm) while the confocal microendoscope provides high resolution (3-5 μm) in the near field (<0.5 mm). Combining an optical illumination path and an ultrasonic receiver on the same platform also facilitates photoacoustic imaging, and in some implementations, a four-modality imaging/therapeutic platform for more flexibility in diagnosis and treatment options, such as for catheter-based intracardiac imaging. CMUT arrays can be used with an arbitrary geometry and small dimensions using photolithographic techniques and standard microfabrication processes.

Figure 19:
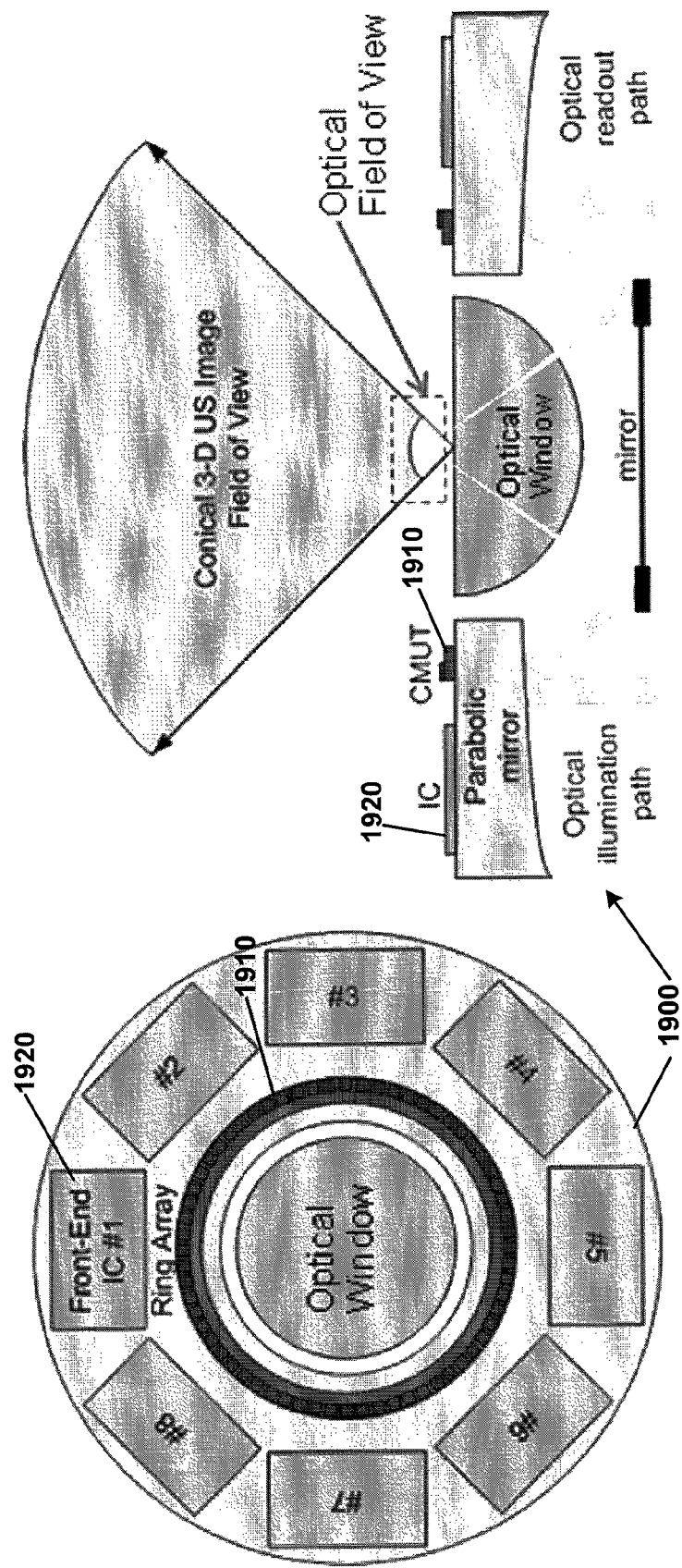
FIG. 19 shows top and side views of an integrated ultrasound/optical microendoscope, in accordance with various example embodiments of the instant disclosure.

FIG. 19 shows top and side views of an integrated ultrasound/optical microendoscope 1900, in accordance with various example embodiments. The microendoscope 1900 includes a CMUT array 1910 as discussed below, and as may be implemented in accordance with, for example, a 64-element, and 2-mm diameter ring array wire bonded to 64 transmit/receive channels in a bank of four custom designed integrated circuits. Operating at 20 MHz, several phantoms including a small metal spring and deployed and undeployed forms of a Palmaz-Schatz coronary stent can be imaged as shown. This approach can be implemented, for example, with an arrangement such as shown in FIGS. 1 and/or 3, or similar devices with the parabolic mirror and optical window as an end region of an endoscope.

In some implementations, the microendoscope 1900 in FIG. 19 includes a CMUT array 1910 having through-wafer via interconnects and bonded on a flexible printed circuit board that also carries front-end integrated circuits (ICs) 1920 used for transmitting and receiving the ultrasound signals. Each IC measures 1.25 mm by 0.75 mm and includes 8 channels of high-voltage T/R switches and low-noise preamplifiers. For backend signal processing and image formation, a general-purpose programmable ultrasound data acquisition and image formation platform can be used (e.g., from Verasonics Inc., Richmond, Wash.) with 64 parallel transmit-receive channels. Microcoaxial cables are used to connect the flexible PCB to the backend processing system. The described ultrasound system provides deep ultrasound 3-D imaging and has an axial resolution of 100 μm. The lateral resolution is 400 μm at 1 cm depth and 800 μm at 2 cm depth. In the synthetic imaging mode, for 2-cm imaging depth volume images can be acquired at a rate of up to 500 fps. The DAC microendoscope 1900 also has a lateral and axial resolution of 3 μm and 6 μm, respectively. The field of view is 400 μm×400 μm with a possible frame rate up to 1020 fps, and provides Hi-Res multispectral fluorescence imaging down to a depth of about 300 μm. As a result, the multimodal DAC microendoscope platform combines a multispectral fluorescence microendoscope with deep ultrasound 3-D imaging, and in addition also provides an ultrasound device that aids the delivery of dyes and molecular therapeutic agents through the methods of sonoporation. Therefore, this multimodal DAC microendoscope platform gives complementary imaging perspectives and resolutions to aid in disease detection and diagnosis, and also can provide local delivery of drugs or contrast agents into the tissue by the methods of sonoporation.

Figure 20:
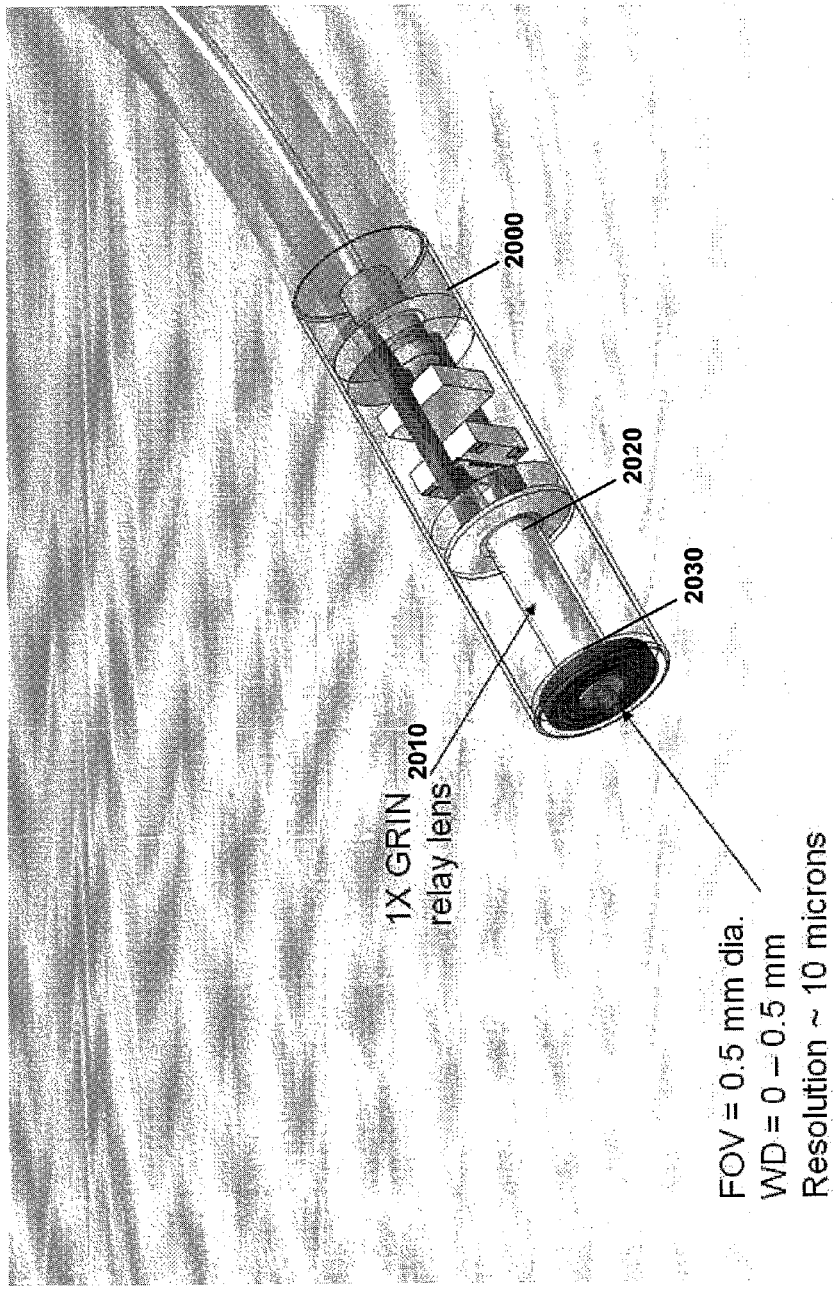
FIG. 20 shows a multimodal DAC microendoscope as discussed above and that includes a GRIN lens in the optical system, in accordance with another example embodiment.
Figure 21:
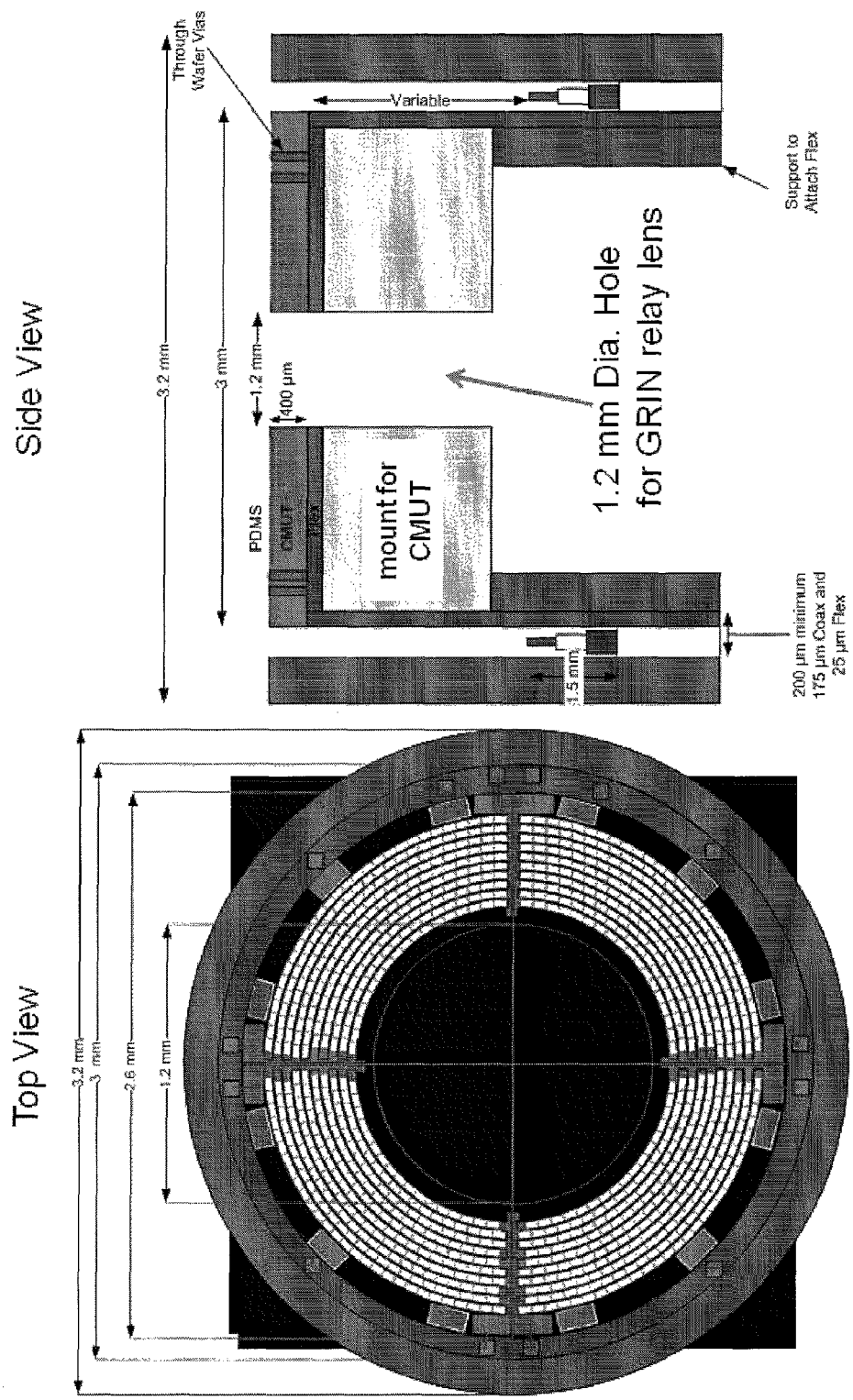
FIG. 21 shows top and side views of a capacitive micromachined ultrasonic transducer (CMUT) and other components that can be implemented with the multimodal DAC microendoscope show in FIG. 20.
Figure 22:
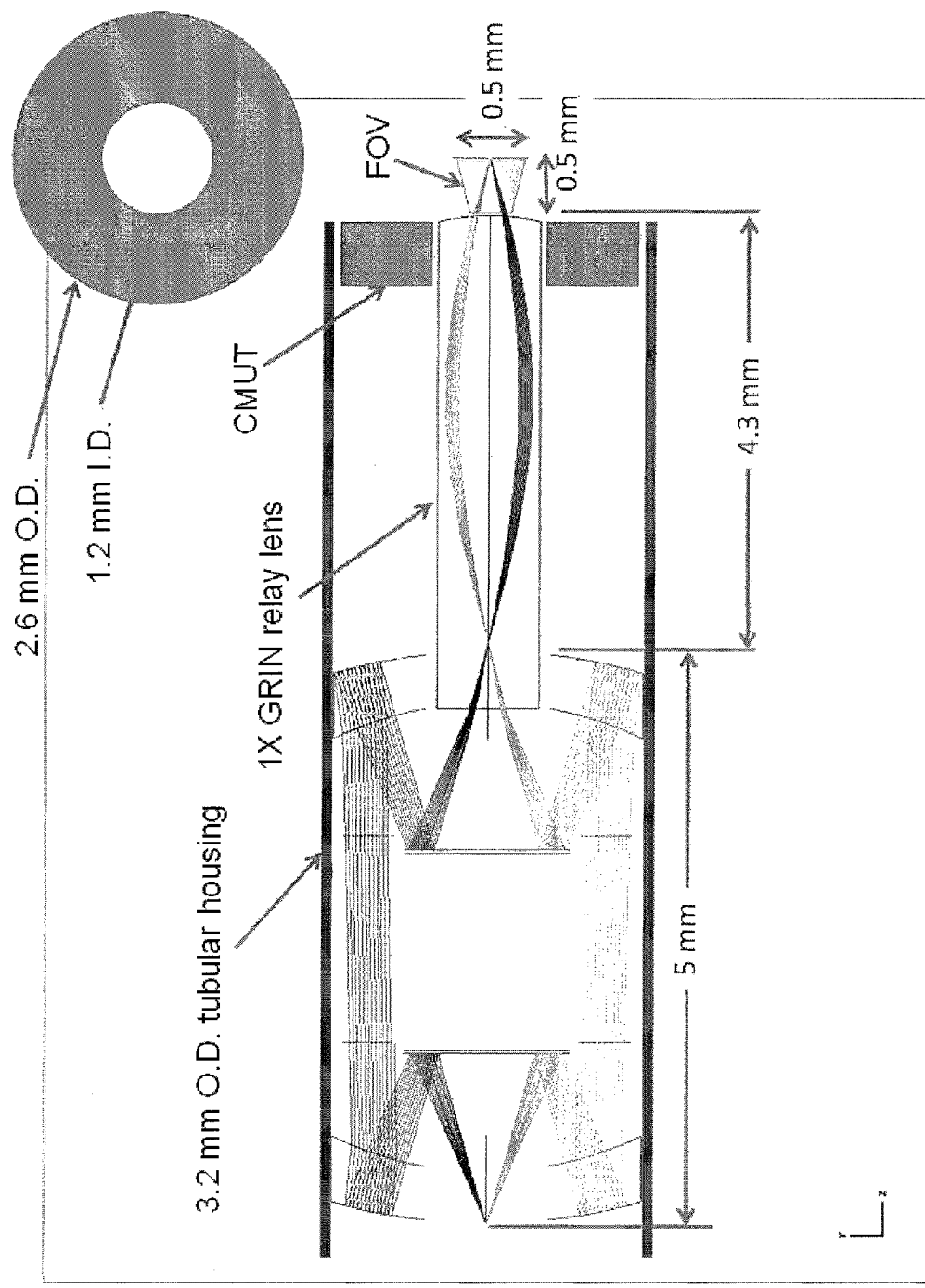
FIG. 22 shows example ray patterns of the microendoscope in FIG. 20 as implemented with a GRIN lens, in accordance with the instant disclosure.

Referring to FIG. 20, a multimodal DAC microendoscope 2000, which may implement components as discussed above and/or shown in the figures, and includes a GRIN lens 2010 in the optical system, in accordance with another example embodiment. The GRIN lens 2010 provides an image relay function for extending the "reach" of the DAC 2000 working distance along the length of the GRIN lens 2010 for more flexible packaging and integration with the CMUT imaging array. In this system, the illumination and collection beams of the DAC optical system are first accepted into the proximal end 2020 of the GRIN relay lens 2010 and then re-imaged into the tissue at the distal end 2030 of the GRIN relay lens 2010. This approach can be used to extend the reach of the illumination and collection beams in order to image tissue at the distal end 2030 of a GRIN relay lens 2010 having a small footprint. This added feature allows more flexibility for construction of different multimodal DAC microendoscope platforms, which can produce a variety of different combinations of optical and ultrasonic imaging/therapeutic modalities. FIG. 21 shows top and side views of a CMUT and other components that can be implemented with FIG. 20, and FIG. 22 shows example ray patterns of the microendoscope in FIG. 20 as implemented with a GRIN lens.

An example CMUT that can used in these embodiments has dimensions of 2.6 mm O.D. and 1.2 mm I.D., which provides a hole that allows the 1 mm diameter GRIN lens to extend through it. The particular CMUT shown in FIG. 21 is configured for receiving or transmitting acoustic energy within a highly concentrated region indicated by the shaded region in FIG. 22. When in the receiving mode, this region represents a high concentration of acoustic sensitivity, and in addition, also represents the 3-D optical field-of-view (FOV) of the DAC microscope. This combination of a 1X GRIN relay design and a highly-focused CMUT receiver allows the construction of a multimodal DAC microendoscope platform to provide high-resolution multispectral fluorescence microscopy with optical-resolution multispectral photoacoustic microscopy and ultrasonic therapy/drug delivery. The optical-resolution photoacoustic microscopy modality implements an end-piece-module designed with a GRIN relay lens and a ring-shaped capacitive micromachined ultrasonic transducer (CMUT), which together provides overlapping acoustic and optical fields in the tissue being imaged.

In some embodiments, the "optical-resolution" photoacoustic microscopy modality operates by first providing optical absorption of the scanning focused illumination beam, which is also pulsed at a high repetition rate. The tissue may be pre-treated with a chromophore contrast agent that selectively absorbs a specific wavelength of light. Many fluorescent dyes can be used in connection with these embodiments, to provide such a contrast agent. When each laser pulse is absorbed, a sudden rise in temperature at the focused spot causes ultrasonic waves with an intensity that is dependent on the local concentration of the chromophore. The ultrasonic waves are received by the CMUT and thus produce an electrical signal representing the acoustic intensity. As the focused beam is scanned in the tissue, a rapid series of short laser pulses produces a photoacoustic image having a resolution that is determined by the size of the focused flying spot. The CMUT can also be operated to transmit acoustic energy for sonoporation applications, and the optics can still function as a high-resolution fluorescence microscope.

The optical FOV is scanned in 3-D as shown in FIGS. 23A and 23B, in which FIG. 23A shows the side view of a 3.2 mm form factor DAC microendoscope during a sequence of three optical scanning conditions. The ray trace shows the beams within the DAC scan-engine and the 1×GRIN relay lens during optical scanning. FIG. 23A (1) shows the distal MEMS scanner used for transverse scanning in the neutral position, which is an image point on the optical axis (on-axis image point). FIG. 23A (2) shows the distal scan mirror tilted +3 degrees. FIG. 23A (3) shows the distal scan mirror tilted −3 degrees.

FIG. 23B shows ray trace simulations of optical scanning when the proximal MEMS scanner (used for axial scanning) is in the neutral position, allowing the distal scan mirror to cause scanning at the tissue surface. FIG. 23B (1) shows the distal MEMS scanner in the neutral position. FIG. 23B (2) shows the distal scan mirror tilted +3 degrees. FIG. 23B (3) shows the distal scan mirror tilted −3 degrees.

Figure 24:
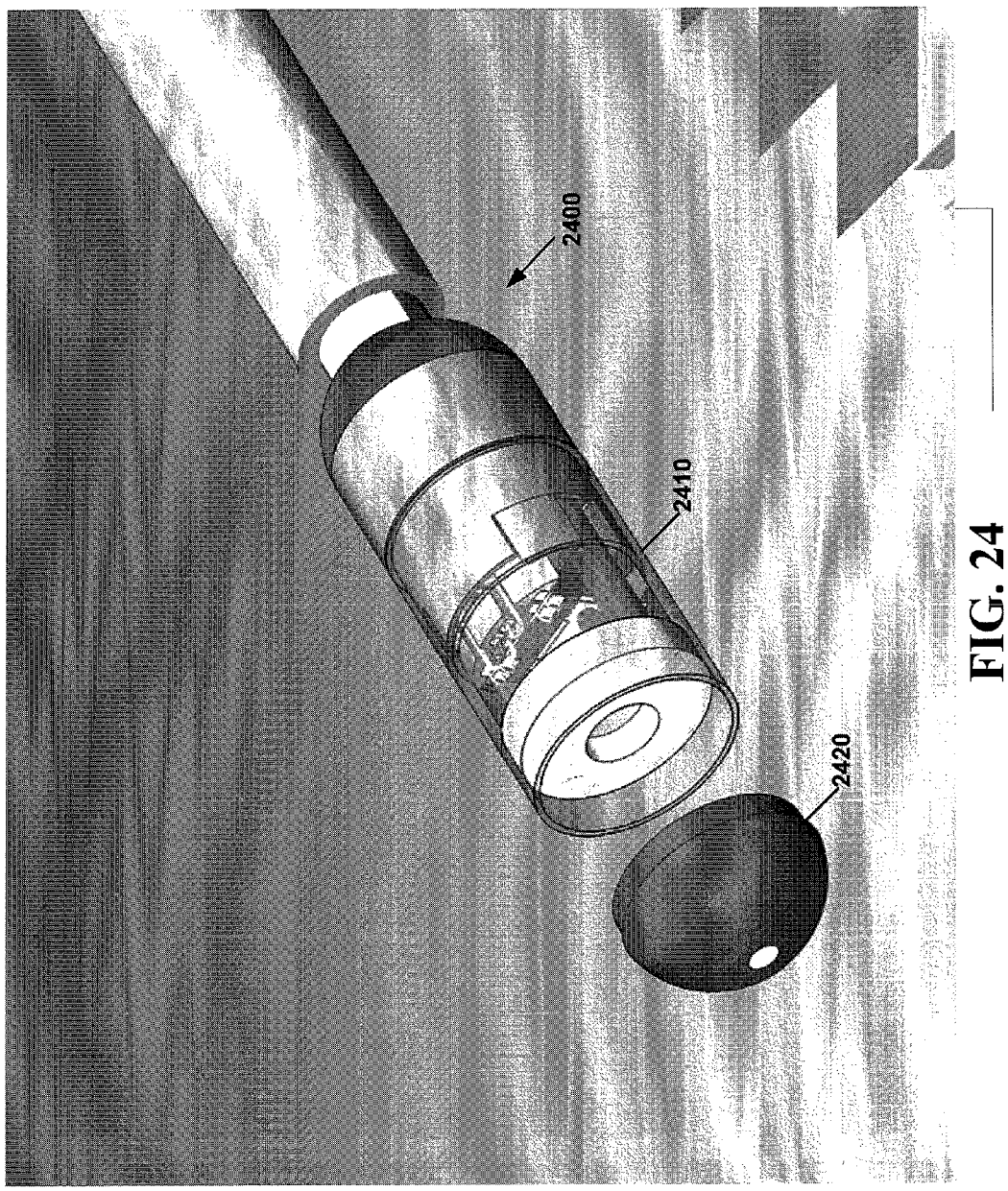
FIG. 24 shows an example embodiment of a modular endoscope including a universal scan-engine-module and a special purpose, multimodal end-piece-module.

FIG. 24 shows a modular endoscope 2400 including a universal scan-engine-module and a special purpose, multimodal end-piece-module 2420 (or several such modules, such as in a package for interchangeable applications). The universal scan-engine-module 2410 is a sub-assembly comprising micro-optics and MEMS components (e.g., as found in DAC microscopes), and the special purpose end-piece-modules 2420 are sub-assemblies, that are compatible with the universal scan-engine-module. The end-piece-modules 2410 are assemblies comprising a GRIN relay lens and a ring-shaped CMUT device, which together provide overlapping acoustic and optical fields within the tissue being imaged or treated. In addition, the some end-piece-modules may be configured for high-resolution imaging when in contact with tissue, and others may allow "non-contact" imaging for achieving wider views. Thus, different multimodal imaging/therapeutic functions are provided by attachment of specific end-piece-modules to the distal end of a universal scan-engine-module.

Figure 25:
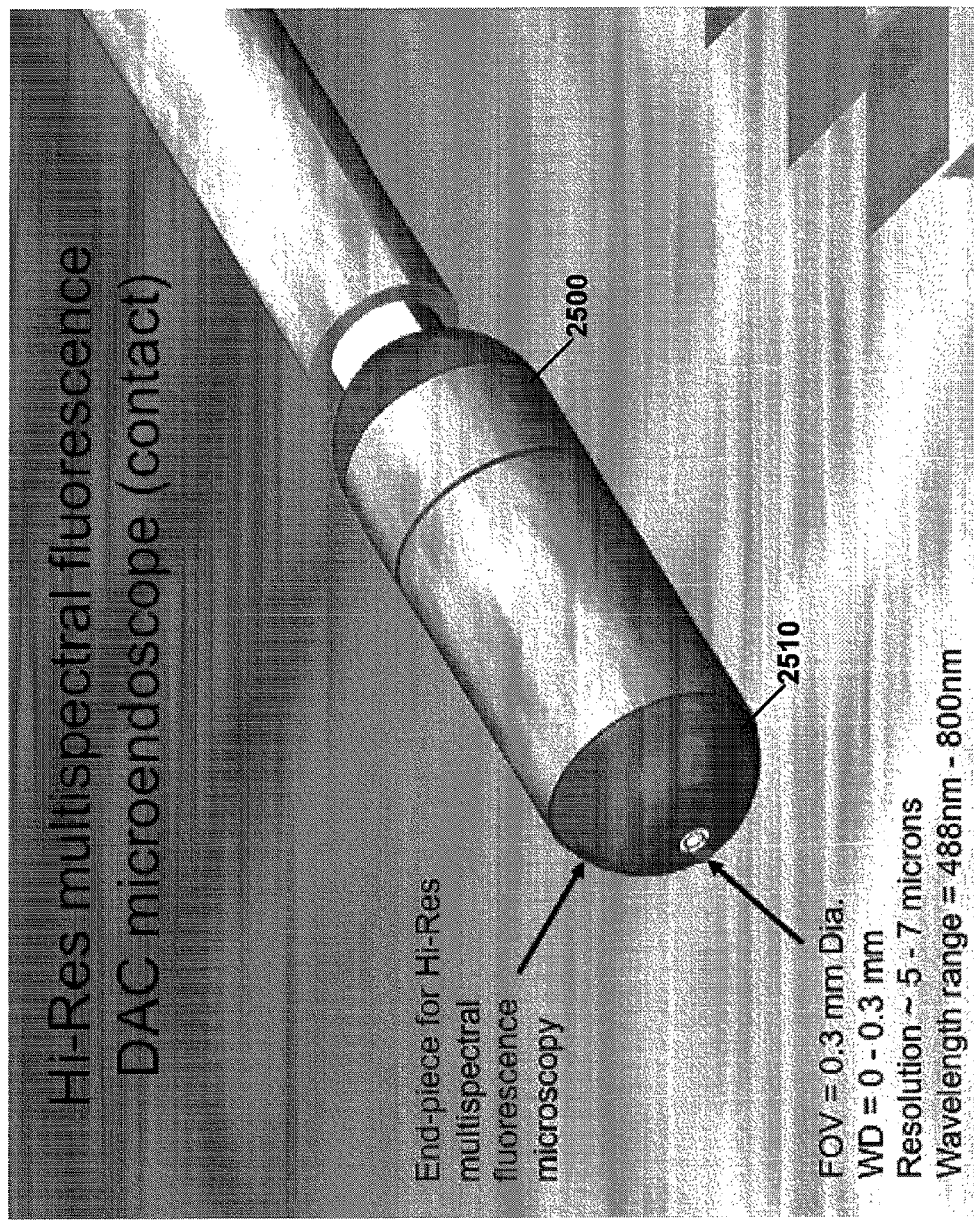
FIG. 25 shows an example embodiment of a high-resolution multispectral fluorescence DAC microendoscope and a universal "scan-engine-module" with a multimodal "end-piece-module"
Figure 26:
FIG. 26 shows a set of multimodal DAC microendoscope platforms, consistent with the instant disclosure, that are modularly constructed by combining the "scan-engine-module" with different compatible special purpose "end-piece-modules"
Figure 27:
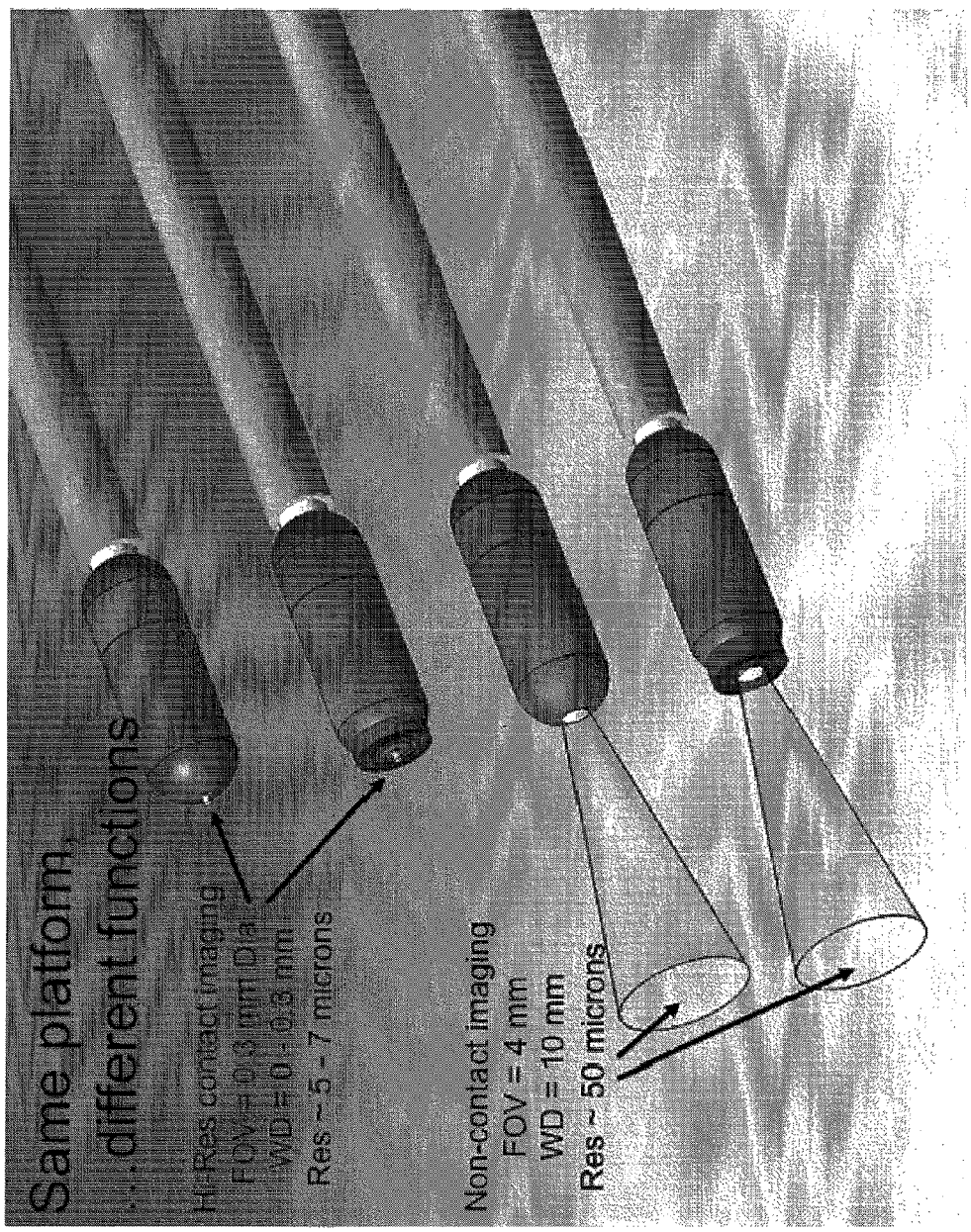
FIG. 27 shows a flexible modular system for construction of in vivo platforms that enable clinical tools for both, point-of-care diagnostic imaging, and therapeutic intervention, based on aspects of the instant disclosure.

FIGS. 25-27 show various other microendoscopes in accordance with other embodiments. Beginning with FIG. 25, a high-resolution multispectral fluorescence DAC microendoscope 2500 combines a universal "scan-engine-module" with a multimodal "end-piece-module" 2510. This particular example of an end-piece-module is designed for high-resolution multispectral fluorescence imaging while it is in contact with the tissue surface. The 3.2 mm form factor allows the microendoscope to fit into the 3.7 mm I.D. instrument channels of standard GI endoscopes. FIG. 26 illustrates a set of multimodal DAC microendoscope platforms in accordance with various embodiments, which enables modular construction via combining a "scan-engine-module" with different compatible special purpose "end-piece-modules", thus facilitating a variety of in vivo platforms that provide specific combinations of imaging and therapeutic modalities for use in the clinic. The end-piece modules shown in FIG. 26 are: hi-res multispectral (contact) fluorescence microendoscope 2610; hi-res multispectral (contact) photoacoustic microendoscope 2620; non-contact fluorescence microendoscope 2630; and non-contact photoacoustic microendoscope 2640. FIG. 27 shows a flexible modular system for construction of in vivo platforms that enable clinical tools for both, point-of-care diagnostic imaging, and therapeutic intervention.

Figure 28:
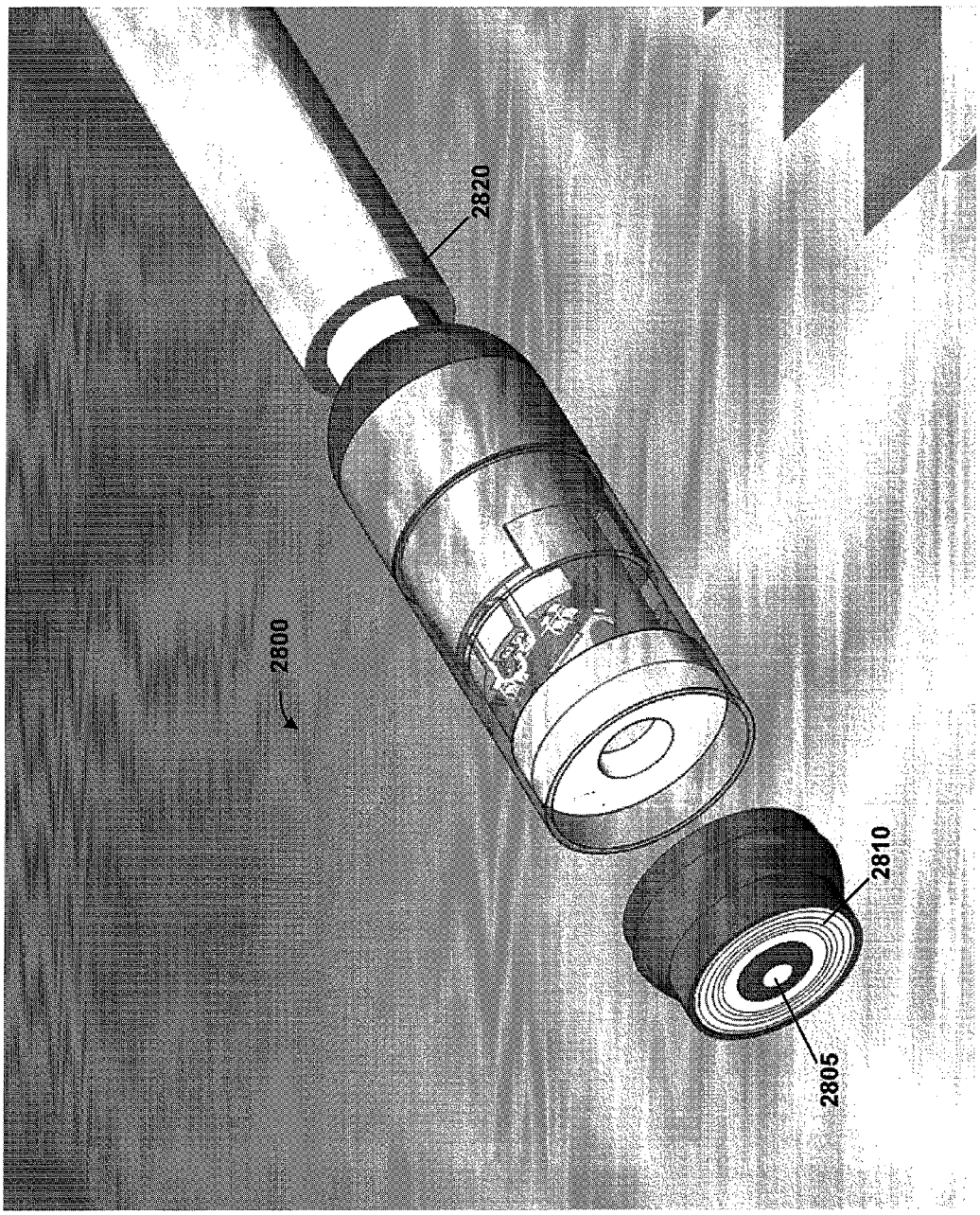
FIG. 28 shows an example embodiment, consistent with the instant disclosure, of a multimodal DAC microendoscope platform for high-resolution photoacoustic microscopy.

FIG. 28 shows a multimodal DAC microendoscope 2800 for high-resolution photoacoustic microscopy, which includes a GRIN relay lens 2805 and a CMUT device 2810 for transmitting and receiving acoustic signals within the optically scanned field-of-view of the high-resolution fluorescence DAC microendoscope 2820. The microendoscope can apply therapeutic levels of ultrasonic energy to tissue.

Figure 29:
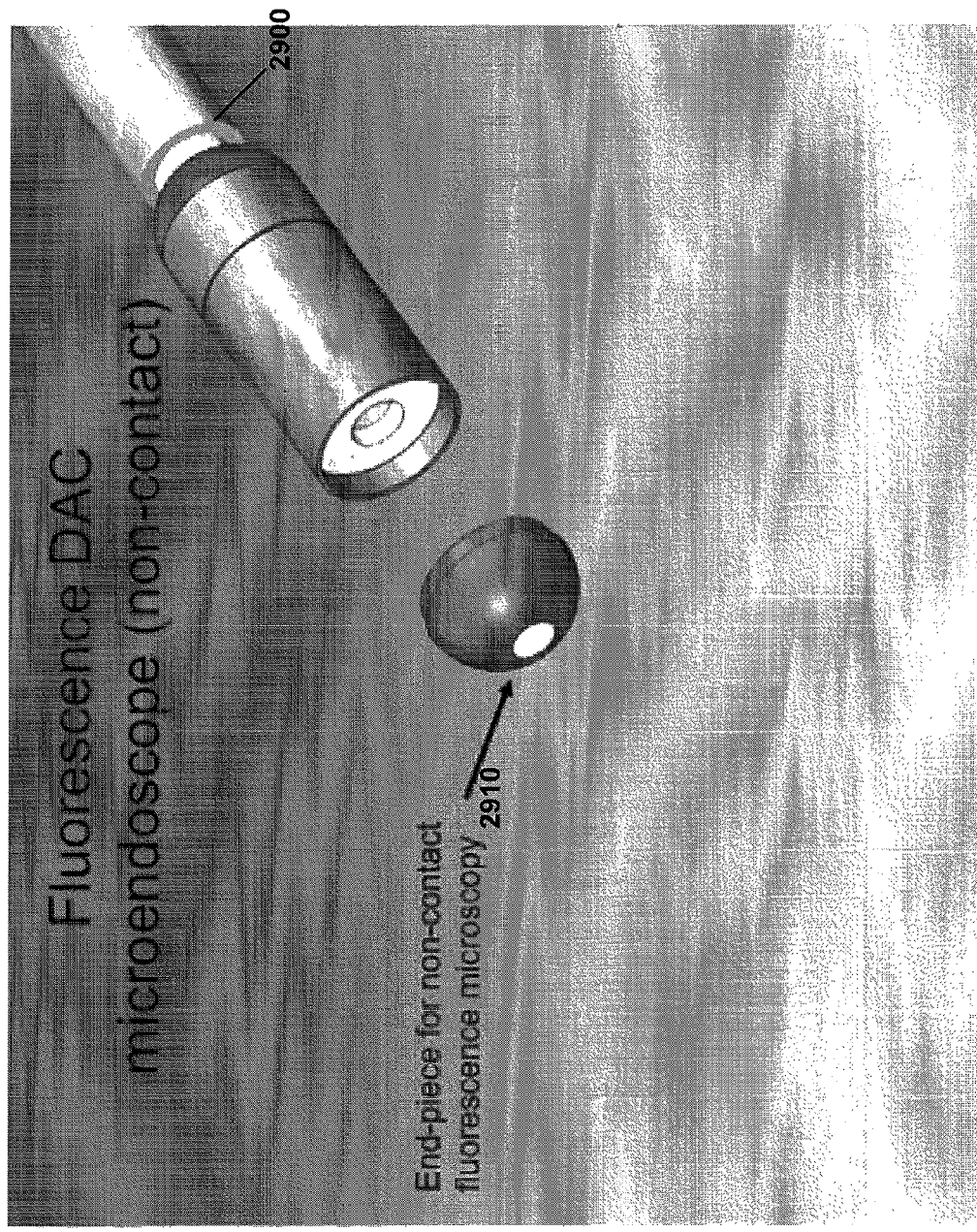
FIG. 29 shows a non-contact fluorescence microendoscope in accordance with an example embodiment of the instant disclosure.

FIG. 29 shows a non-contact fluorescence microendoscope 2900 in accordance with another example embodiment, which combines a "scan-engine-module" with a special purpose "end-piece-module" 2910 designed for non-contact "wide-view" multispectral fluorescence imaging of the tissue surface.

Figure 30:
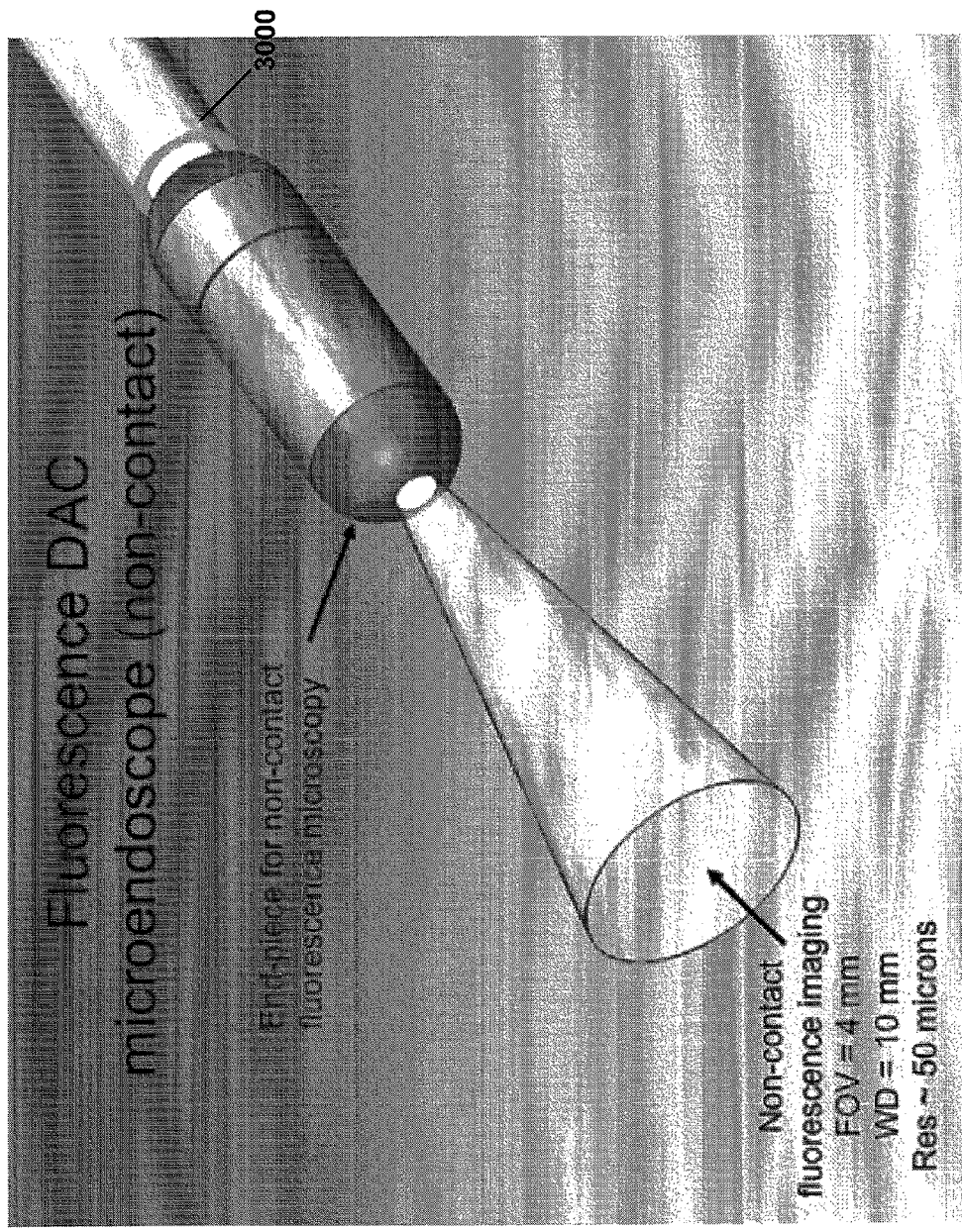
FIG. 30 shows a non-contact "wide-view" DAC fluorescence microendoscope in accordance with an example embodiment of the instant disclosure.

FIG. 30 shows a non-contact "wide-view" DAC fluorescence microendoscope 3000 in accordance with another embodiment, which has a long working distance for use in surveying larger areas of tissue, such as to locate concentrations of fluorescent contrast agents such as the COX-2 fluorescent probe.

Figure 31:
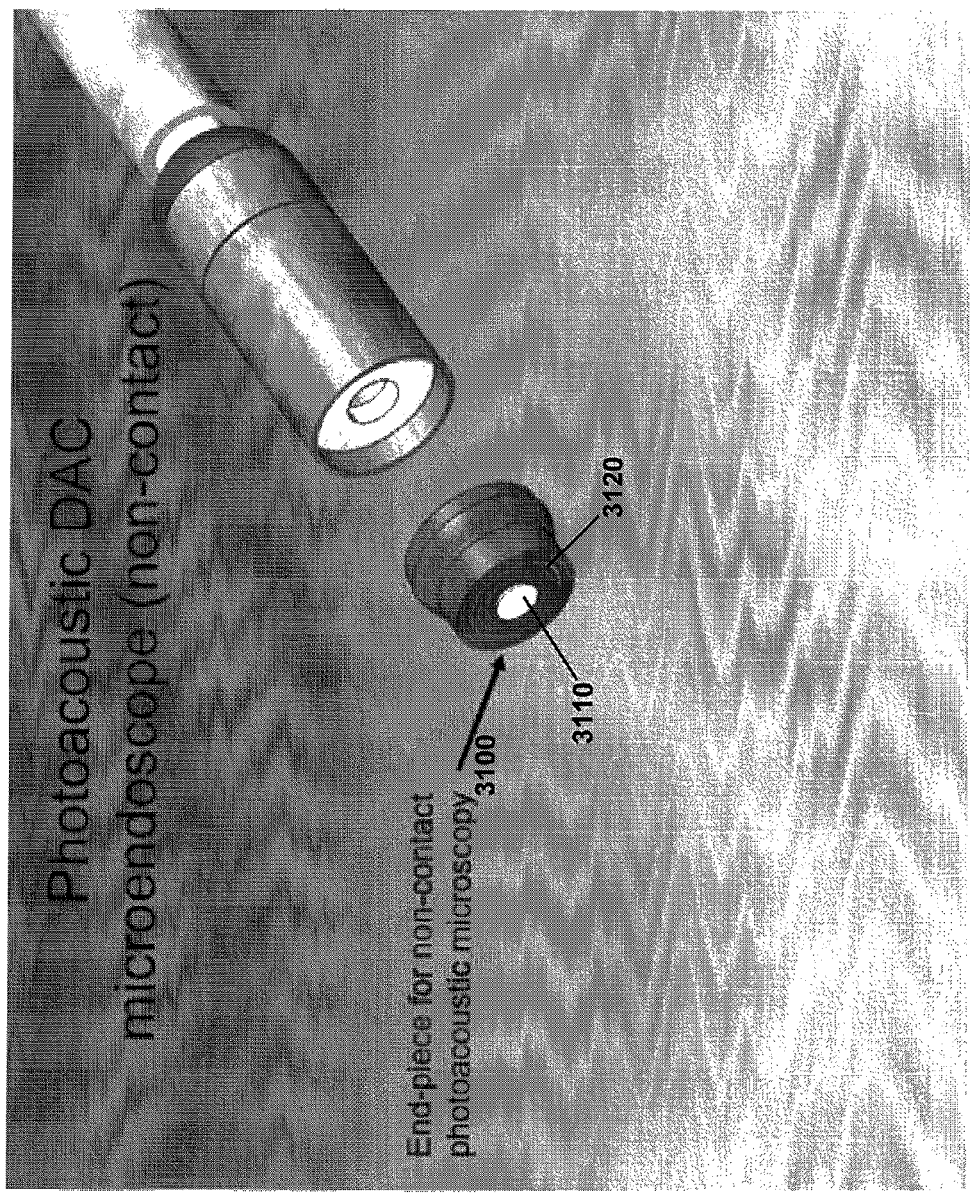
FIG. 31 shows an example embodiment of an end-piece-module for the non-contact photoacoustic microendoscope.
Figure 32:
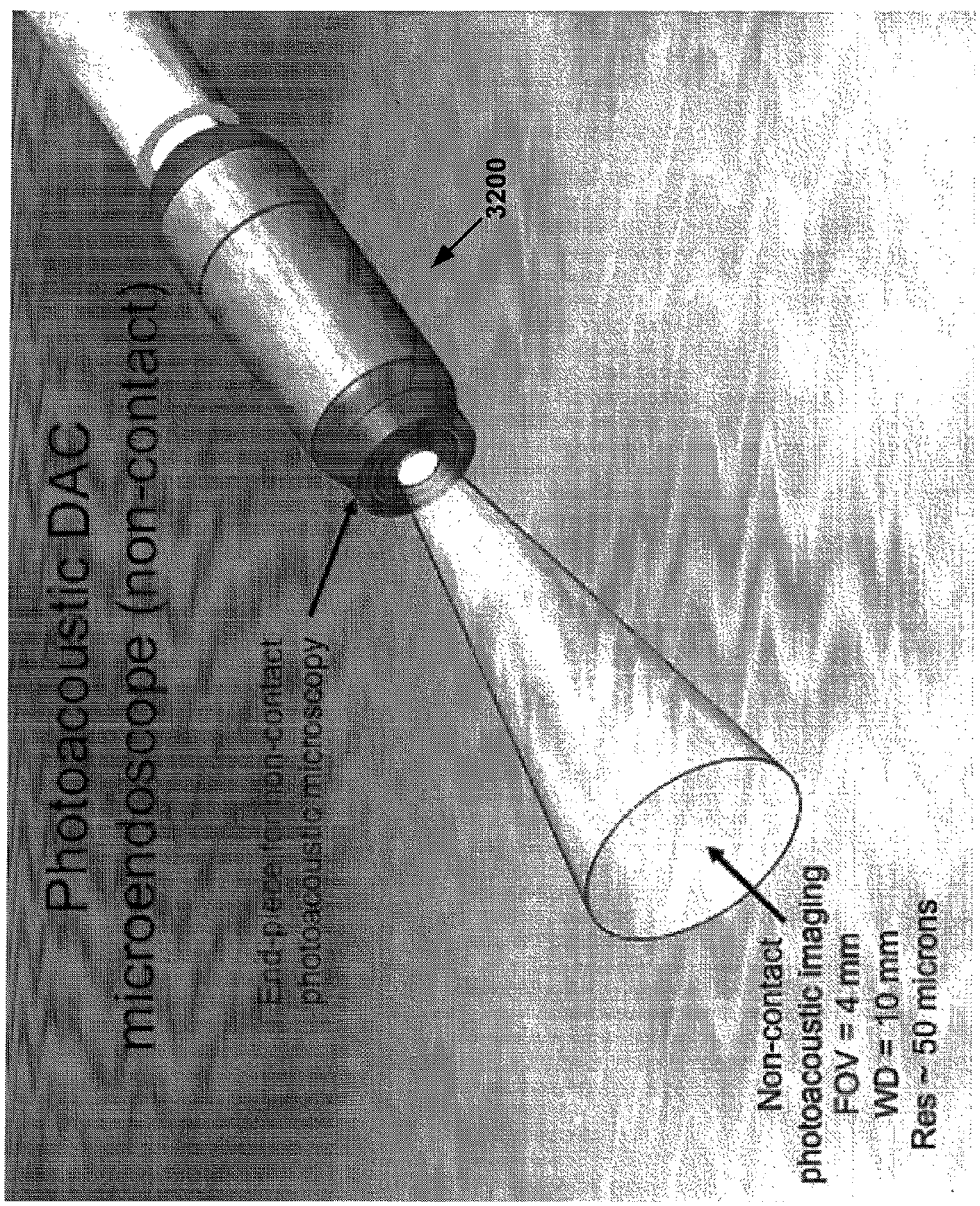
FIG. 32 shows an example embodiment, consistent with the instant disclosure, of a non-contact type of photoacoustic DAC microendoscope.

An example end-piece-module for this non-contact photoacoustic microendoscope 3100 is shown in FIG. 31, which includes a GRIN relay lens 3110 and a CMUT device 3120 designed for transmitting and receiving acoustic signals within the optically scanned field-of-view of the non-contact type of "wide-view" fluorescence DAC microendoscopes such as shown in FIGS. 27, 30, and 32.

FIG. 32 shows a non-contact type of photoacoustic DAC microendoscope 3200, which is a multimodal DAC microendoscope platform configured to operate a "wide-view" fluorescence DAC microendoscope and a "wide-view" photoacoustic microendoscope.

Figure 33:
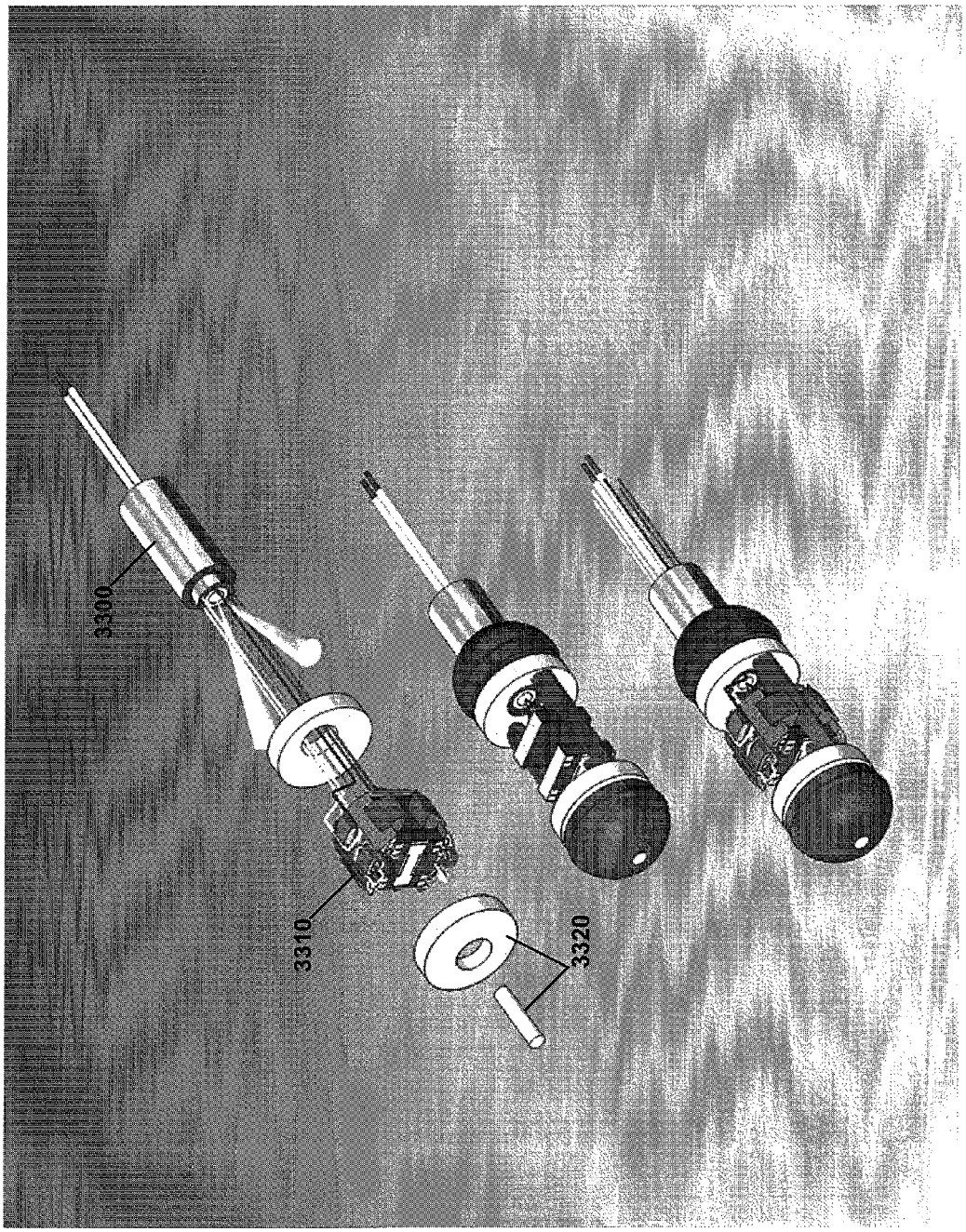
FIG. 33 shows a complete assembly of parts used to construct a multispectral DAC microendoscope in accordance embodiments of the instant disclosure.

FIG. 33 shows an assembly of parts (fiber optics 3300, micro-optics 3320, and MEMS components 3310) used to construct a multispectral DAC microendoscope in accordance with one or more embodiments herein. These parts are pre-assembled into the scan-engine-module and the end-piece-module sub-assemblies, which together comprise the complete system.

Figure 34:
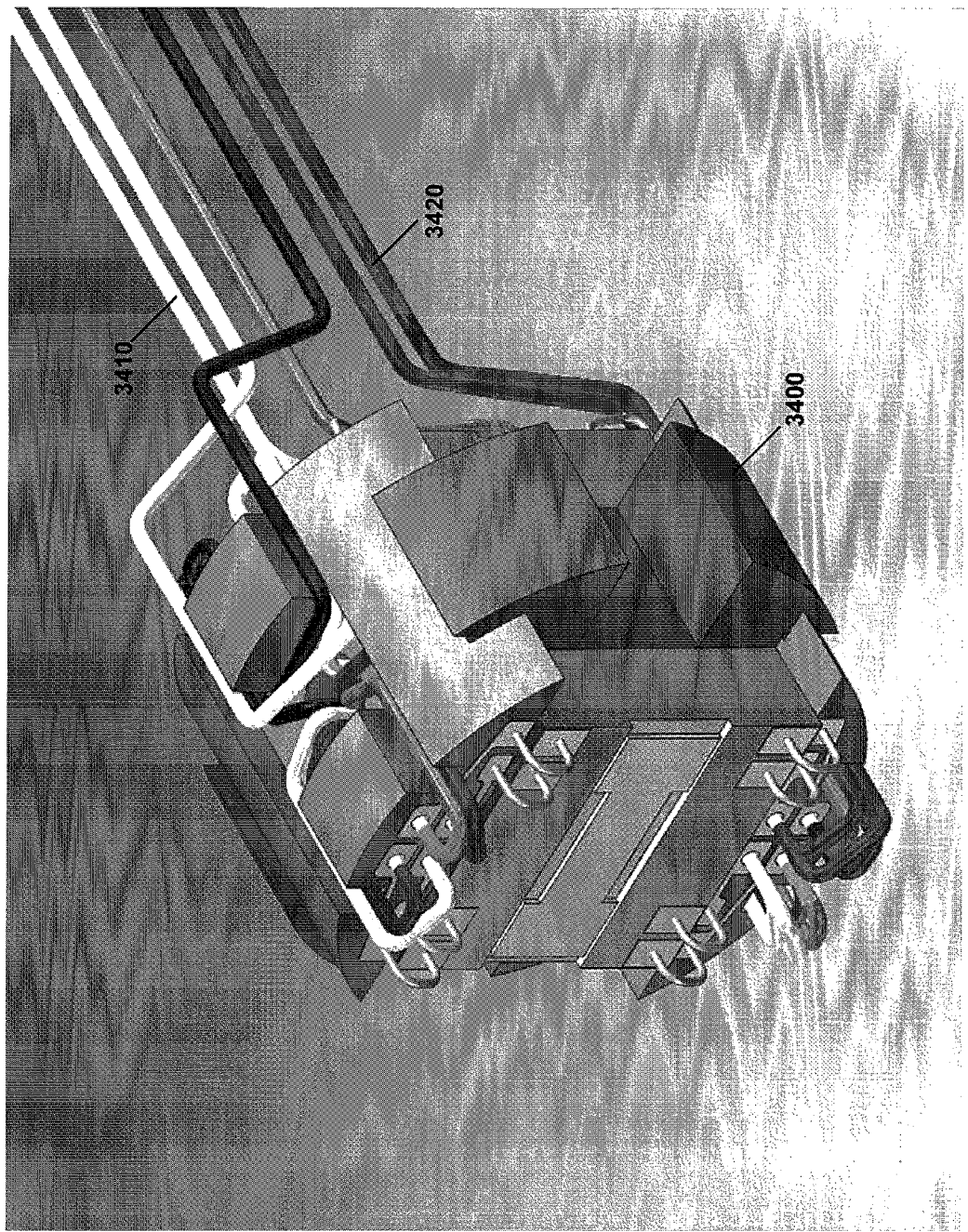
FIG. 34 shows a MEMS scanner for a scan-engine-module based on aspects of the instant disclosure.

FIG. 34 shows a MEMS scanner 3400 for a scan-engine-module as discussed herein, with signal wires 3410 routed out of the package and through the umbilical alongside the optical fibers 3420 that carrying the optical signals during imaging. Additional wires may be used for driving a CMUT device in certain platforms. The MEMS scanner 3400 can be implemented, for example, with one or more of the endoscopes shown in and described in the figures above.

Figure 35:
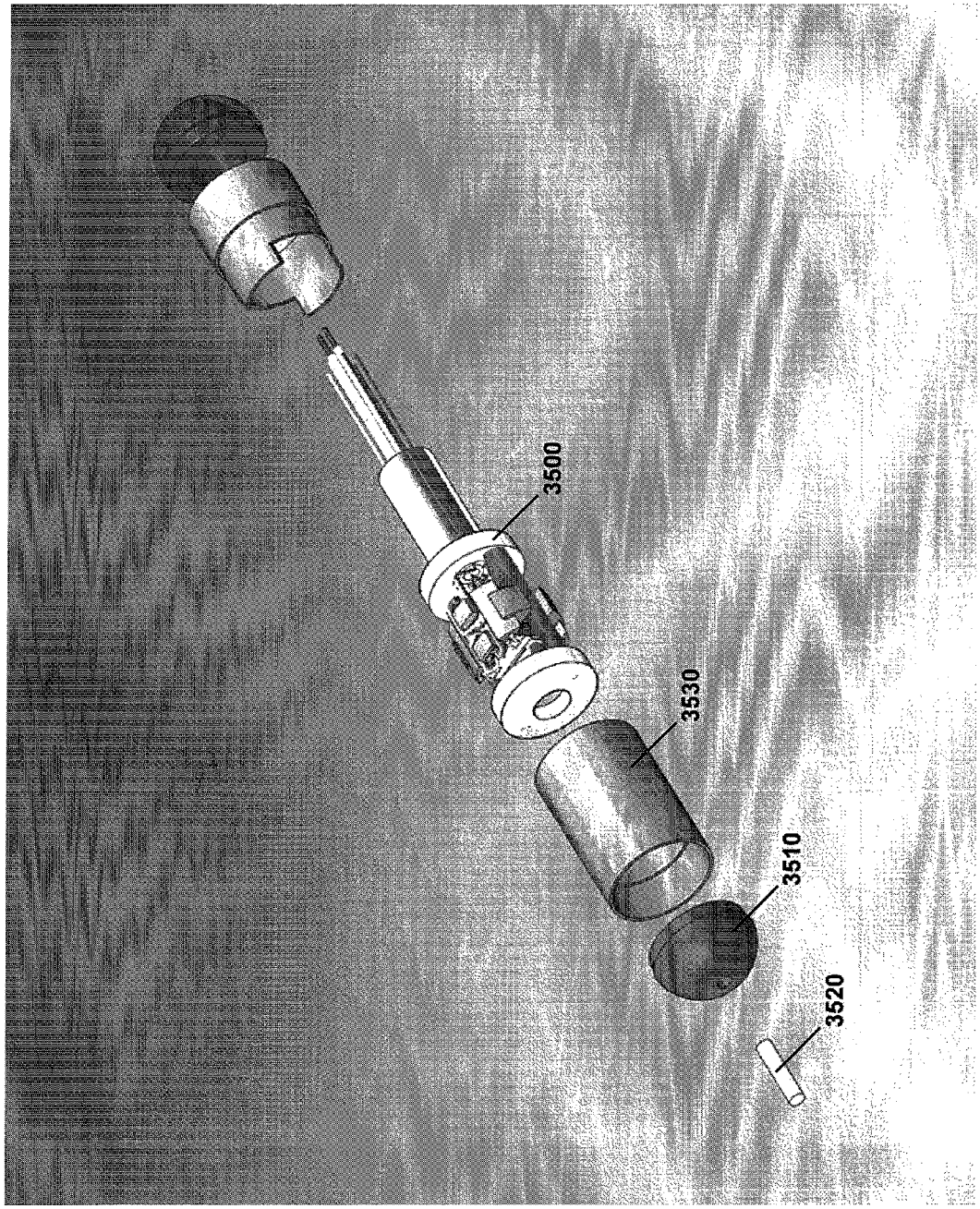
FIG. 35 shows a universal scan-engine-module with end-piece-modules including a GRIN relay lens and outer tubular housing sections.
Figure 36:
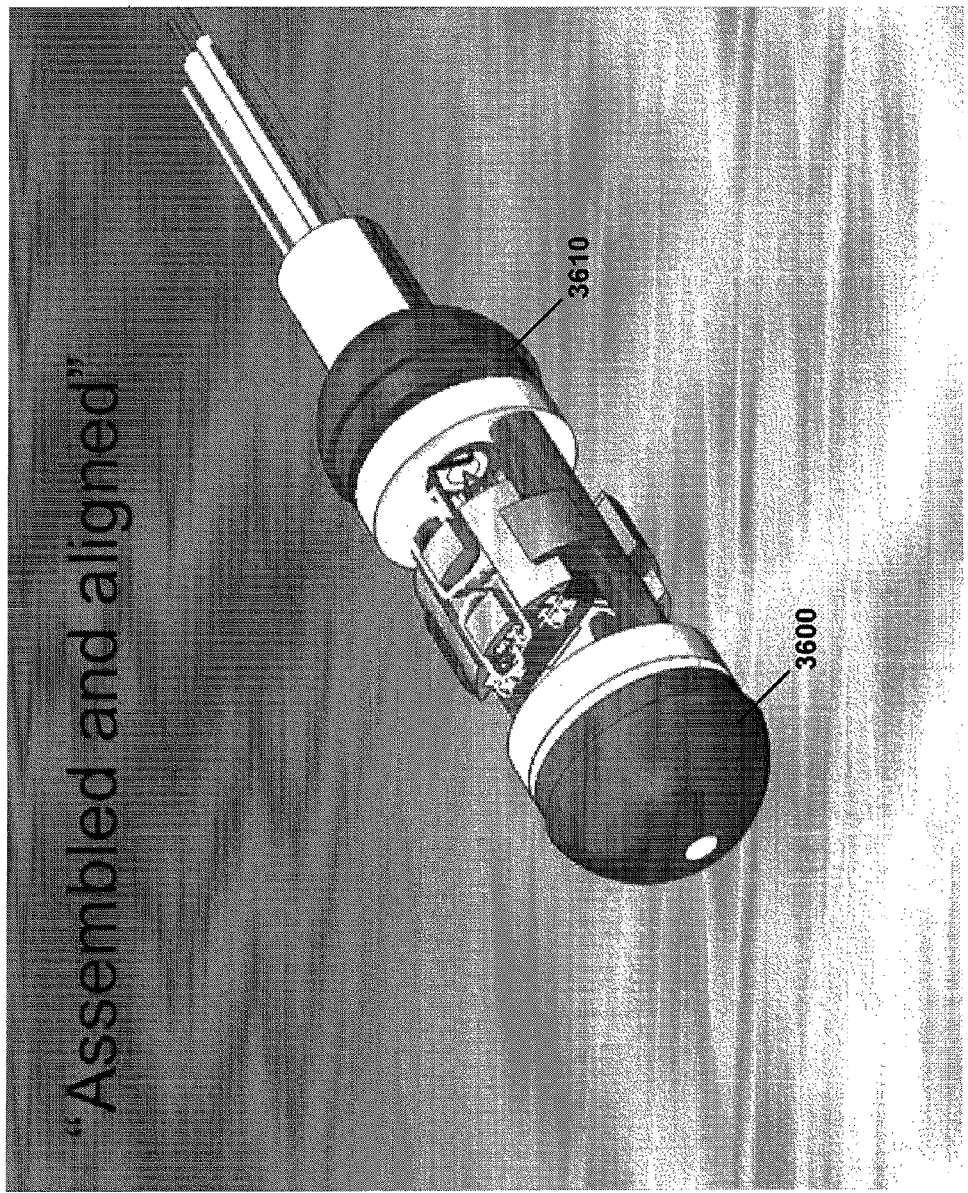
FIG. 36 shows an example embodiment of an end-piece-module sub-assembly and a universal scan-engine-module sub-assembly, consistent with aspects of the instant disclosure.
Figure 37:
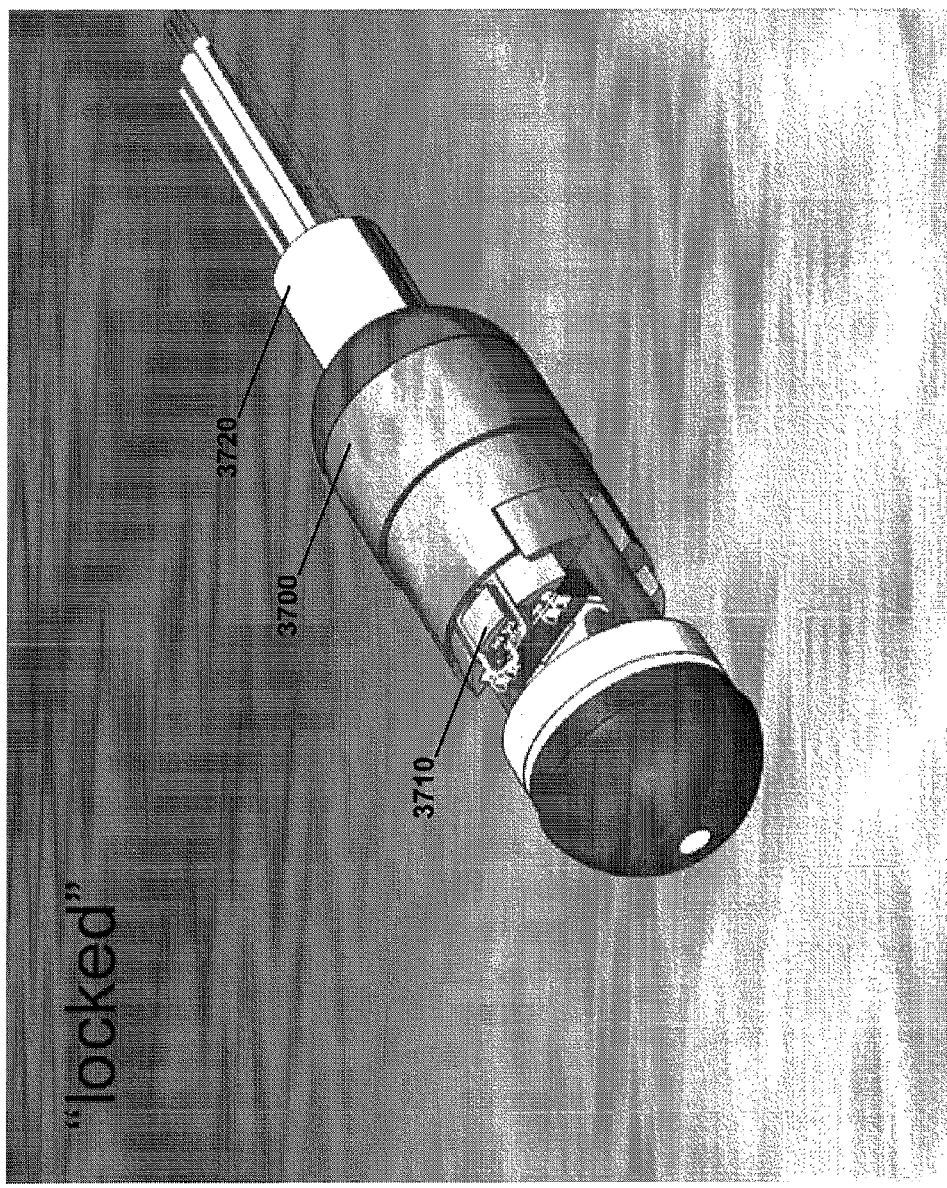
FIG. 37 shows a first section of the outer tubular housing which provides a means for aligning and locking a MEMS scanner sub-assembly into place.
Figure 38:
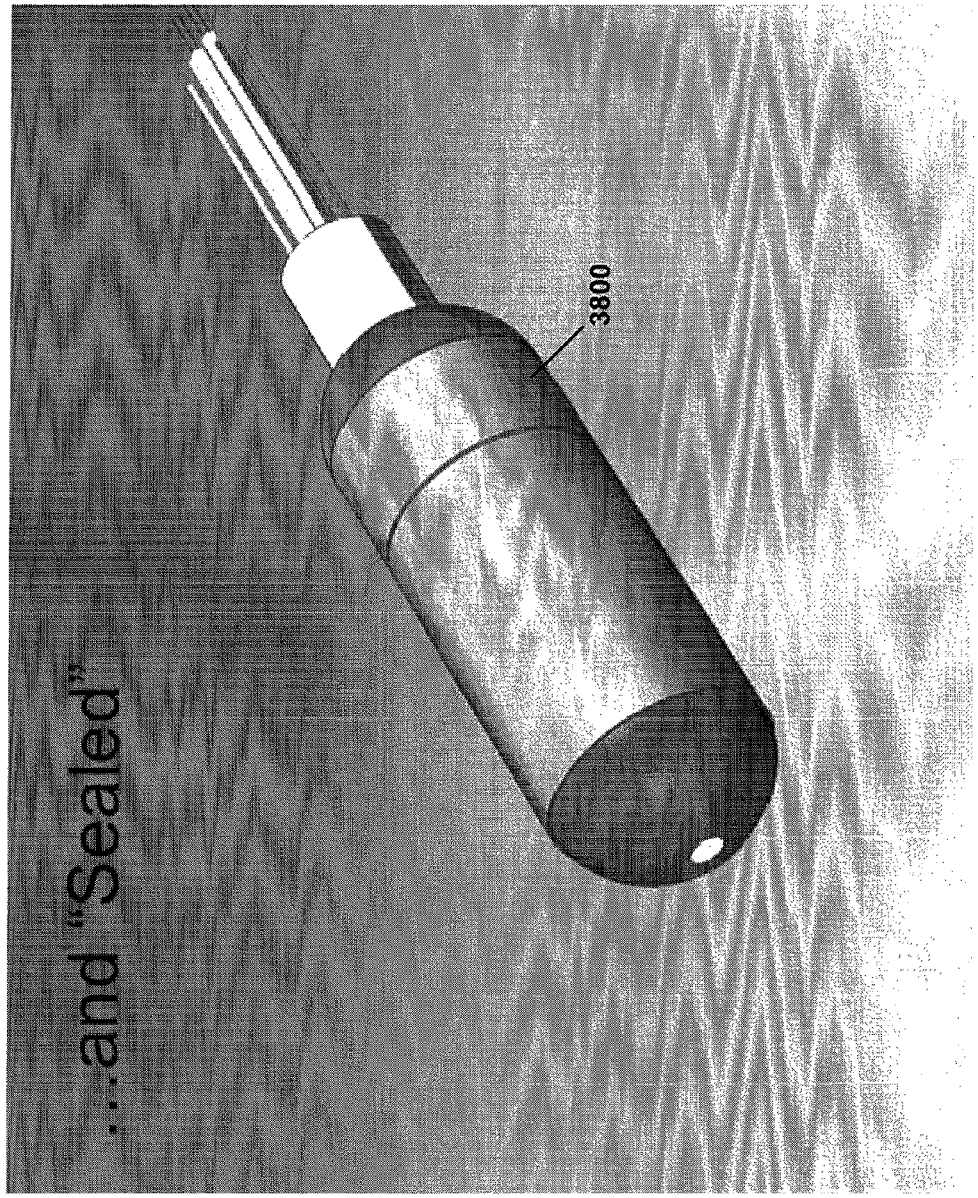
FIG. 38 shows a second section of an outer tubular housing, which provides the final seal for the complete multimodal microendoscope, in accordance with the instant disclosure.
Figure 39:
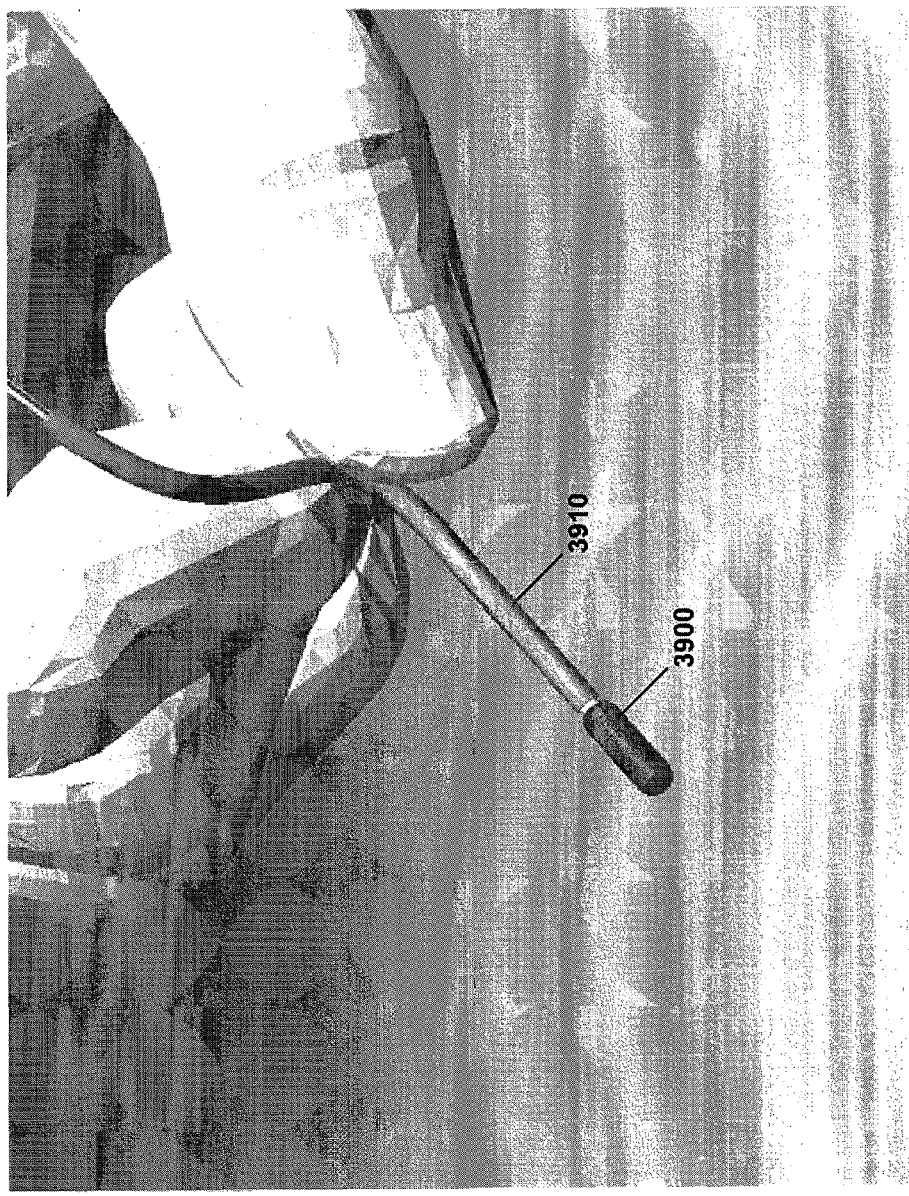
FIG. 39 shows a complete microendoscope, in accordance with the instant disclosure, with the flexible umbilical.

FIGS. 35-39 show components of an endoscope type device, which may be implemented together. In this context, the respective embodiments shown in these figures are described together, with the understanding that they may be separately implemented. Beginning with FIG. 35, a scan-engine-module 3500 has an end-piece-modules 3510 including a GRIN relay lens 3520 and outer tubular housing sections 3530. FIG. 36 shows an end-piece-module sub-assembly 3600 and a universal scan-engine-module sub-assembly 3610 configured for flexible modular assembly and self-alignment of parts, which can be implemented with the module 3500. FIG. 37 shows the first section of outer tubular housing 3700, which provides a means for aligning and locking a MEMS scanner sub-assembly 3710 into place to keep it constrained from rotating relative to the dual-fiber ferrule 3720. This facilitates proper alignment of the dual-fiber ferrule 3720 with the scanning axes of the MEMS scanners, and also mitigates/prevents twisting of the fibers and signal wires after assembly. FIG. 38 shows a second section of an outer tubular housing 3800, which provides the final seal for the complete multimodal microendoscope. FIG. 39 shows the complete microendoscope 3900 with the flexible umbilical 3910 that contains and protects the optical fibers and signal wires (hand shown in figure for scale).

For general information regarding scanning, and for specific information regarding scanning approaches and ray-trace diagrams that may be used in connection with one or more example embodiments such as shown in FIG. 35 (e.g., using a DAC-scan-engine-module), reference may be made to FIGS. 59-81 in Appendix B of the above-referenced provisional patent document (Ser. No. 61/446,423). For example, with specific regard to FIG. 78, some embodiments involve using a GRIN image relay lens with the scan-engine-module to produce a long working distance and large field-of-view to facilitate non-contact imaging modes. The scan mirrors in this configuration can still operate in the same way as without a GRIN lens, but the proximal scanner may be used in a fixed position to achieve a particular working distance from the tissue instead of producing an image at a particular depth in the tissue.

As discussed above, the various microendoscope arrangements characterized herein may be implemented with a variety of different types of optics. In various embodiments, catadioptric mirrors are used to facilitate the passing of source and target light in connection with MEMS-type scanning mirrors. These catadioptric mirrors are implemented as p-type (with two parabolic reflective surfaces) and s-type (spherical reflective surfaces) that face each other, in accordance with various embodiments. One of the parabolic mirrors collimates beams originating at the ends of two single-mode optical fibers, and then the second mirror focuses both collimated beams such that the focal points overlap inside the tissue. Components of a microendoscope used in these embodiments may include the catadioptric mirrors as described, as well as two MEMS scanners (e.g., as in FIG. 3), and optical fibers for respectively carrying source and image light, such as a dual fiber ferrule containing two single-mode fibers.

Referring again to FIG. 3, an illumination beam 335 and a collection beam 340 are passed as shown. The illumination beam 335 follows a path originating from the end of a single-mode fiber 300 (illumination fiber) and ending at a focused point within the tissue 345, and the collection beam 340 originates from within the tissue and then ends where it is focused into the end of the collection fiber. In this arrangement the catadioptric mirrors 305/320 are facing each other and the two MEMS scanners 310/315 are facing away from each other. The 2-D MEMS lateral scanner rasters the beams for constructing a 2-D cross-sectional image within the tissue, where the image plane is substantially parallel to the tissue surface. In addition, the 1-D MEMS depth scanner allows adjustment of depth of this image plane below the tissue surface. The beams diverging from the two fibers are first folded back towards the fibers by one of the MEMS scanners, and then the beams are collimated by the other catadioptric mirror. The beams from two angularly-mounted, single-mode fibers 300 are intentionally angled towards each other at a predetermined angle in order to provide that each of the diverging beams will reflect off of a respective flat mirrored surface of the alignment prism 330 (having two parallel mirrored surfaces). When the thickness and position of the alignment prism 330 is adjusted properly, then the two diverging beams will have a common virtual confocal source point 345, which is where the two virtual images of the fiber ends are superimposed at a single point. Also, a dual-fiber ferrule 325 can be used position the fibers 300 at the proper spacing and angle for proper alignment of the fiber ends. This virtual confocal source point 345 is then imaged into the tissue by the image relaying properties of the optical system, which is provided by the two facing parabolic mirrors 305/320. The two beams thus collimated by the source-side catadioptric mirror 305 are then accepted by the target-side catadioptric mirror 320, which then causes the beams to be focused at an overlapping focus point 345 within target tissue. The symmetrically placed mirrors 305/320 provide optical surfaces needed for collimation, alignment, and focusing of light along all the beam paths inside the microscope, and also within the tissue.

A hemispherical solid immersion lens (Index-matching SIL) 350 having a refractive index that approximately matches the index of tissue can also be used in connection with the mirrors for imaging, with flat side placed against the tissue to be examined and providing an index-matched optical interface for transmission of the focused beams into the tissue. The hemispherical SIL element 350 improves the imaging resolution by minimizing optical aberrations that can occur at the tissue interface.

In general, the light in the DAC microscope follows a one-way "around-the-loop" path beginning from the illumination fiber and ending at the collection fiber. Referring again to FIG. 3, the illumination beam 335 emanating from the end of an illumination fiber diverges towards the first scan mirror 355, and then it is directed to the first parabolic mirror 320 to be collimated. Next, the collimated illumination beam is directed to the second parabolic mirror 305 where it is focused, directed towards the MEMS scanner 310, and then steered by the angular movement of the scan mirror. During scanning, the converging illumination beam is steered over a predetermined range of angles into the tissue where it comes to a focus. This is also the point where the collection beam 340 originates as reflected or fluorescence light emanating from this focal point region of tissue. The path of the collection beam 340 in the microscope is a mirror image of the illumination beam path 335, but traveling in reverse order and impinging on the same optical components lying between the tissue and the collection fiber. The light in the collection beam 335 is focused and enters the end of the collection fiber, which acts as a confocal microscope pinhole. This light is then carried to the detector (e.g., a PMT) and processed into an image. One of the MEMS scanners is configured for Z-shifting towards the target for fast vertical scanning of the variable working distance (WD), and the other mirror is configured for transverse scanning of the image-point via three-degree rotation such that the X-Y image plane is also scanned along the Z-direction (deeper into the tissue), thereby providing an "all-MEMS" 3-D scanning capability.

Figure 40:
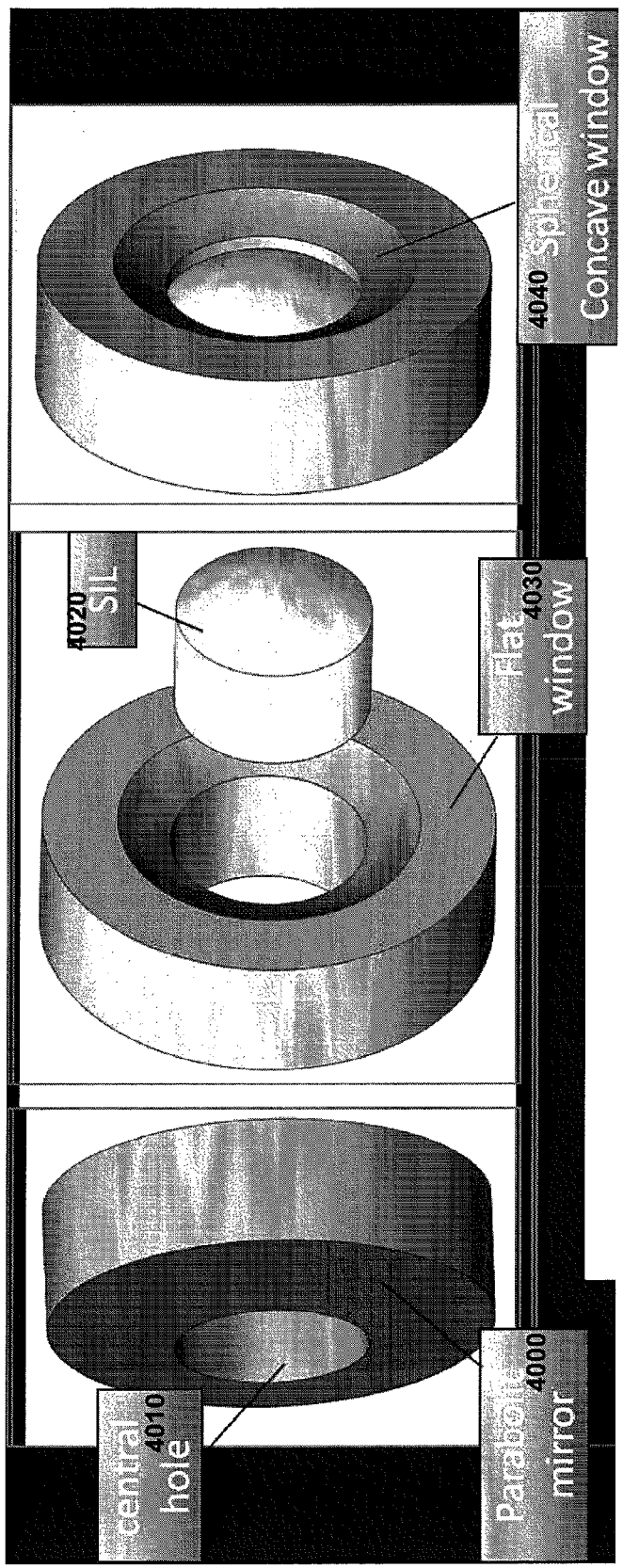
FIG. 40 shows a P-type (two parabolic reflective surfaces) catadioptric mirror in accordance with the instant disclosure.
Figure 41:
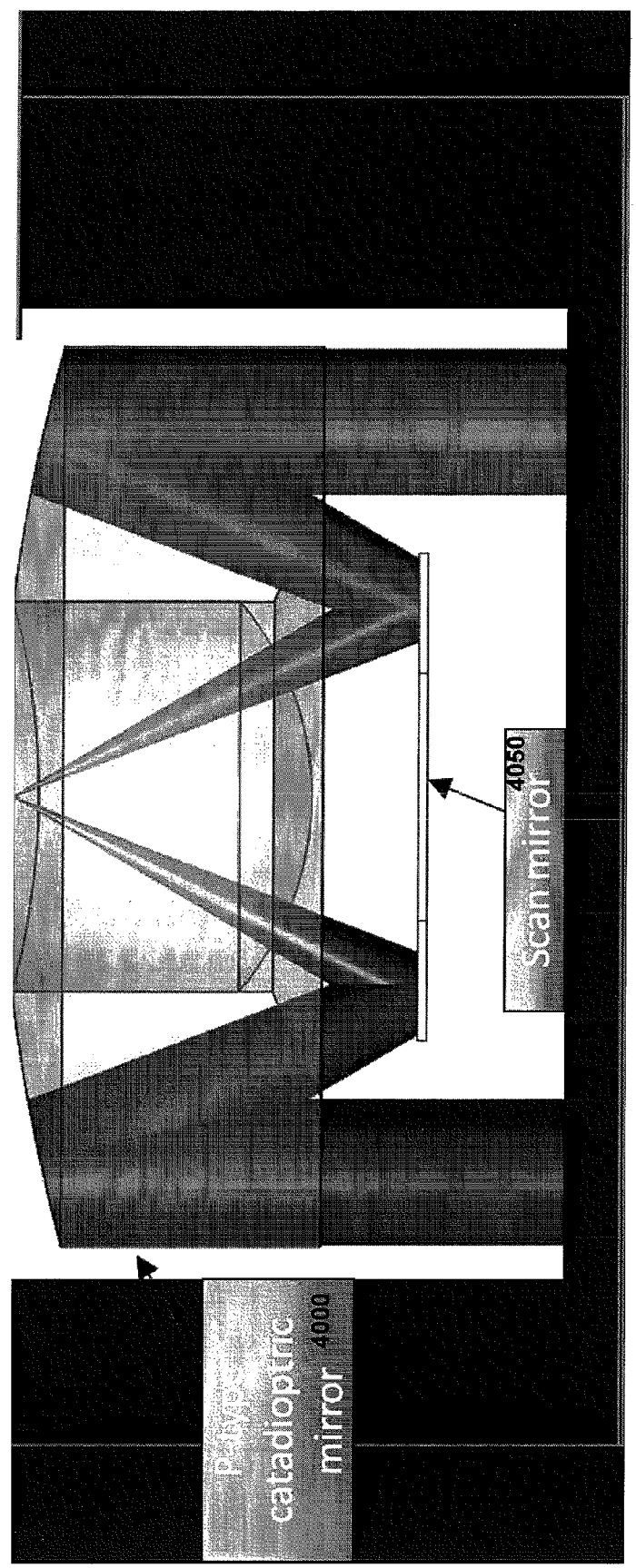
FIG. 41 shows a P-type catadioptric mirror in accordance with a particular embodiment of the instant disclosure.

FIGS. 40 and 41 show a P-type catadioptric mirror 4000 in accordance with a particular embodiment. The P-type catadioptric mirror 4000 is an integrated optical element that provides multiple optical surfaces: including a flat annular entrance/exit window 4030 for both collimated beams, an annular parabolic mirror surface for focusing both beams, and an annular spherical concave window 4040 for the beams to exit towards scan mirror. A hole 4010 in the middle facilities insertion of an index-matching hemispherical SIL 4020 as discussed above, which provides a spherical convex window for re-entry of the beams from the scan mirror 4050 to the tissue interface.

Optionally, a slight concave surface (e.g., with a depth of about 150 microns) may be included, as shown in FIGS. 40 and 41, which may increase the maximum total depth of imaging to more than 300 microns. The windows integrated into this component provide input and output of the beams before and after being reflected from the inside surface of the parabolic mirror (from within the transparent body of the component). These windows are designed to have curvatures that closely match that of the beams that are entering and exiting the integrated optical component. For example, since the exit windows are flat and the collimated beams are perpendicular to the windows, then no chromatic aberration is produced at this interface. With this approach, minimal focusing of the beams is produced by these refractive surfaces (windows) and the internal parabolic mirror provides most of the focusing power of the component. This results in achromatic optical components that can provide the needed beam collimating and focusing in a DAC optical system. In some applications where it is desired to perform multispectral fluorescence microscopy over a large spectral range (i.e., extending from 488 nm-800 nm), fibers that are single-mode at the longer (NIR) wavelengths of this spectrum are used, and may operate as multimode fibers at the shorter wavelengths. The described P-type catadioptric mirror optical elements may be fabricated using glass or optical plastics such as acrylic.

Figure 42:
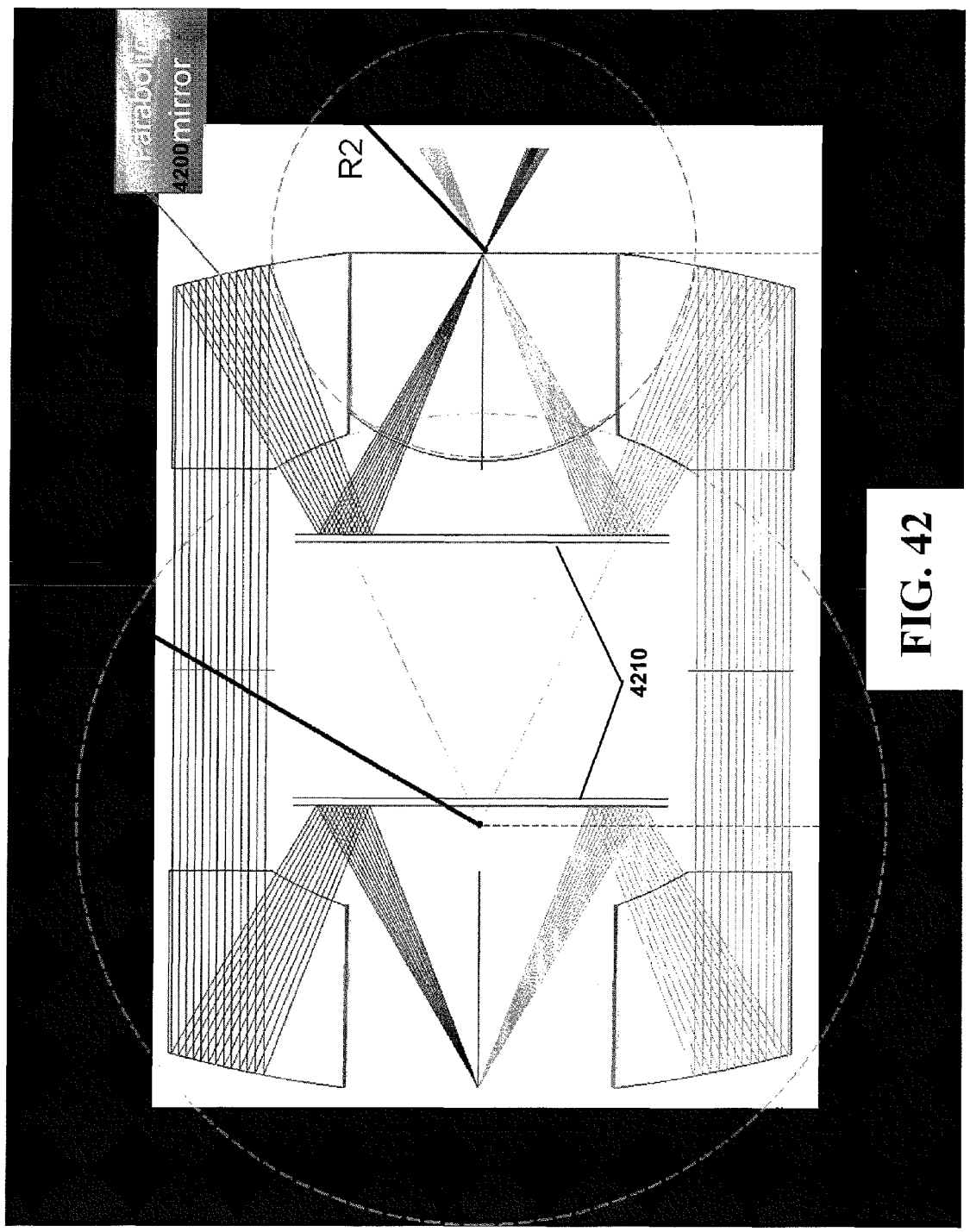
FIG. 42 shows a Zemax raytrace model in accordance with example embodiment of the instant disclosure.

FIG. 42 shows a Zemax raytrace model of a 3.2 mm form factor DAC microscope having an optical design based on two P-type catadioptric mirrors 4200 facing each other and two scan mirrors 4210 facing away from each other (e.g., as shown in FIG. 3), in accordance with another example embodiment. The P-type catadioptric mirrors 4200 include annular parabolic mirrors having a focal length given by f, and an annular spherical concave window having a radius of curvature=R1. A central hole locates the hemispherical SIL, which has a radius of curvature=R2.

Figure 43:
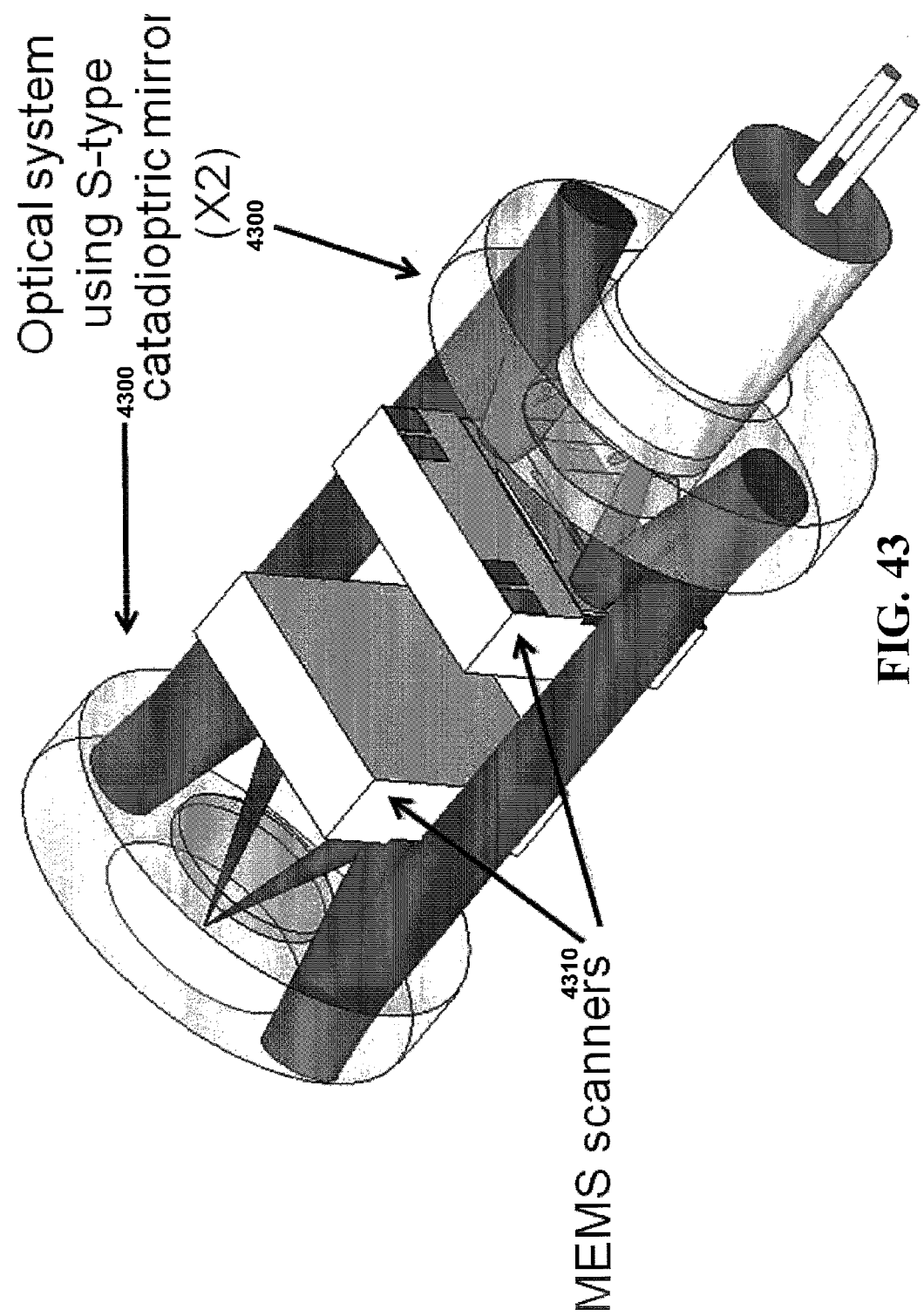
FIG. 43 shows a multispectral DAC microscope having two S-type (spherical reflective surfaces) catadioptric mirrors facing each other and two MEMS scanners facing away from each other, in accordance with an example embodiment of the instant disclosure.
Figure 44:
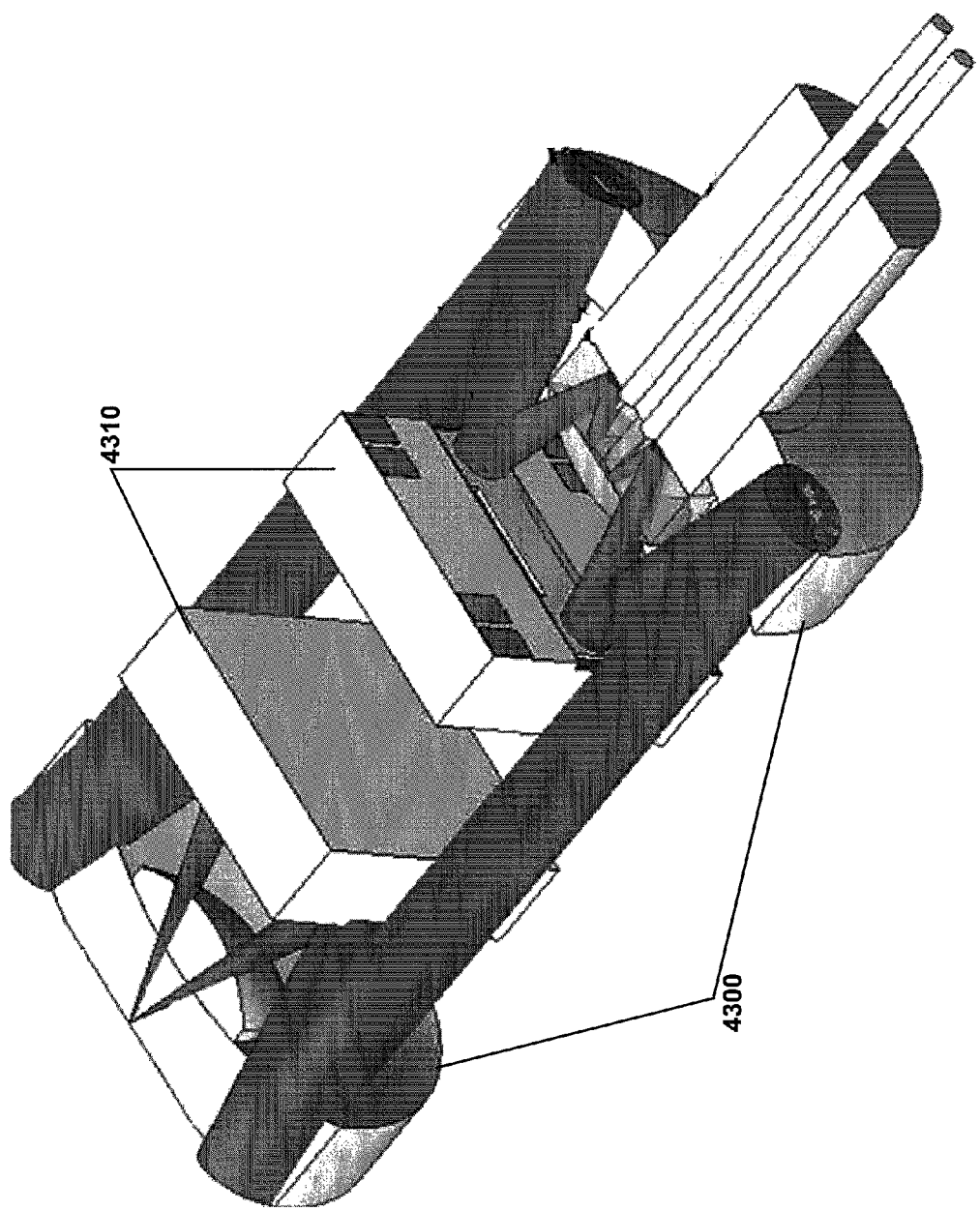
FIG. 44 shows a multispectral DAC microscope having two S-type catadioptric mirrors facing each other and two MEMS scanners facing away from each other, in accordance with an example embodiment of the instant disclosure.
Figure 45:
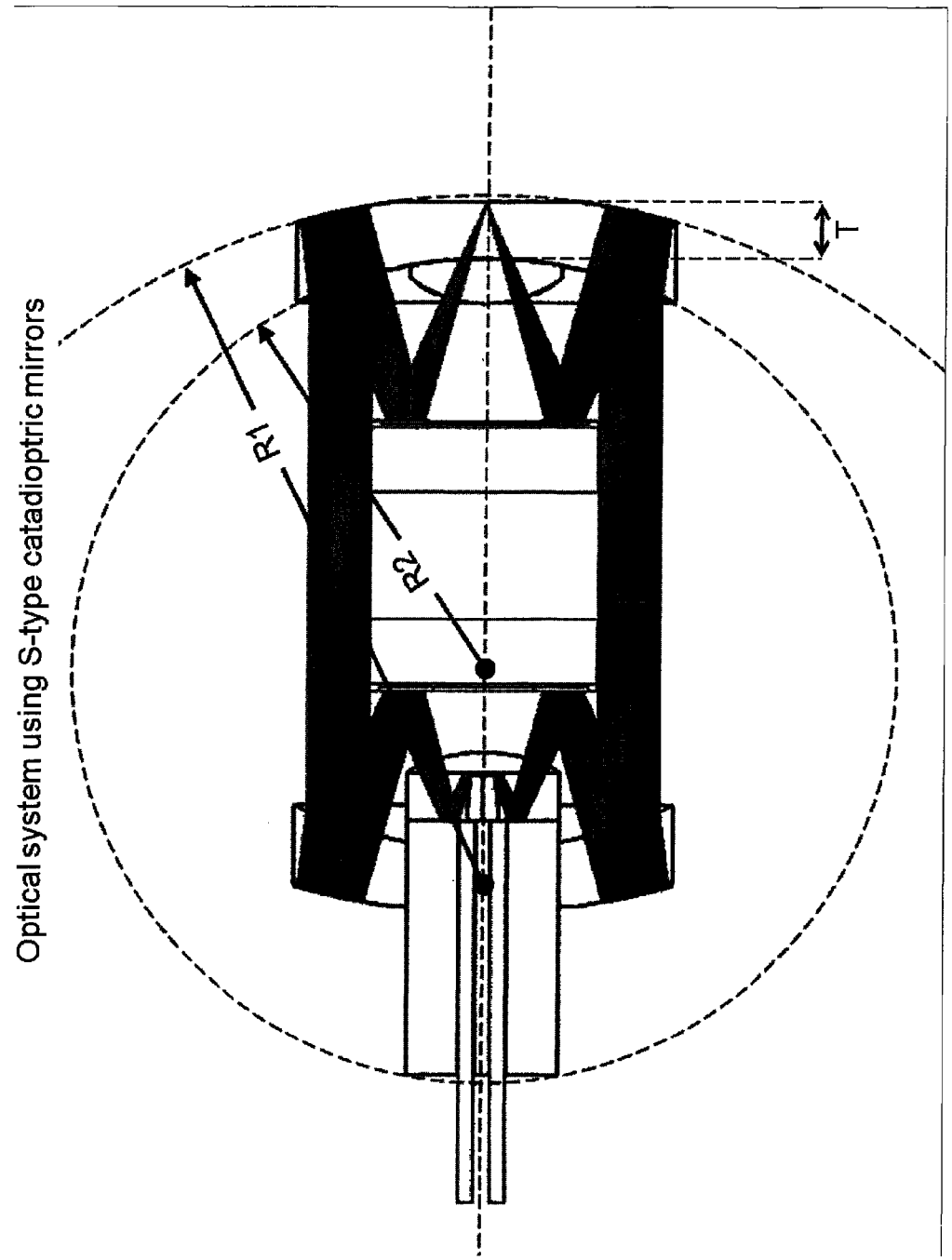
FIG. 45 shows example design parameters R1, R2, and T of the S-type catadioptric mirror in accordance with an example embodiment of the instant disclosure.

FIGS. 43-45 show a multispectral DAC microscope having two S-type catadioptric mirrors 4300 facing each other and two MEMS scanners 4310 facing away from each other, in accordance with another example embodiment. The principle beam paths are similar to the beams paths shown in FIG. 3 and described above, where the illumination beam is indicated in lower beam and the collection beam is indicated as the upper beam. FIG. 45 shows example design parameters R1, R2, and T of the S-type catadioptric mirror, which has one reflective surface and one refractive surface, which does not necessarily employ an aspherical surface (parabola). The spherical reflective surface has a radius of curvature given by R1, and a spherical optical window having a radius of curvature given by R2. The values for R1 and R2 can be set, together with the center thickness given by T, to a desired focal length f. Also, most of the aberrations that normally occur when using spherical mirrors to focus collimated beams can be reduced significantly by proper choice of these parameters.

Figure 46:
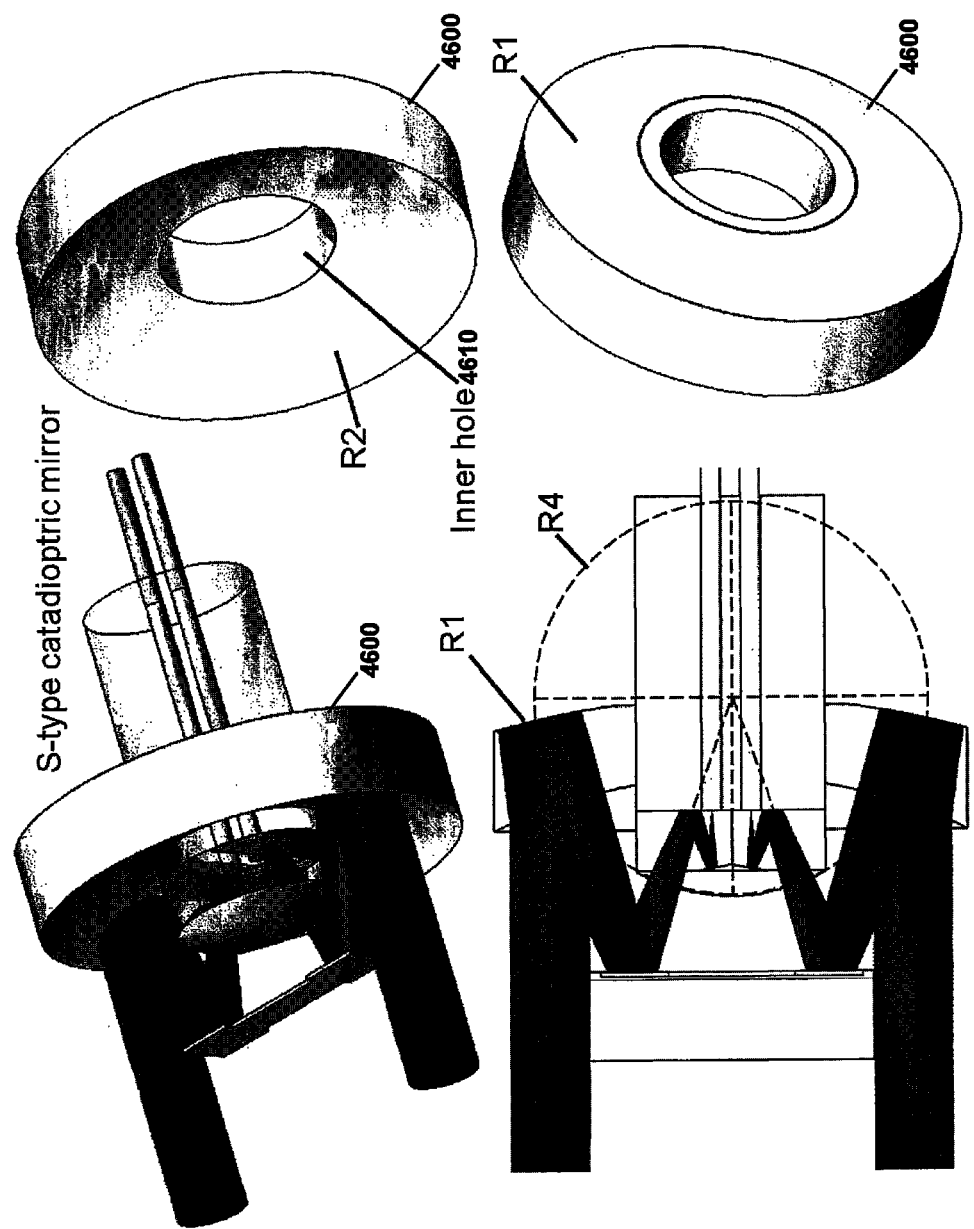
FIG. 46 shows a variation of an S-type catadioptric mirror specifically designed for positioning at the "fiber end" of the DAC microscope, in accordance with another embodiment of the instant disclosure.

FIG. 46 shows a variation of an S-type catadioptric mirror 4600 designed for positioning at the "fiber end" of the DAC microscope, in accordance with another example embodiment. A thru-hole 4610 is provided for mounting of a Dual-fiber ferrule, or for mounting a hemispherical SIL element as discussed above. As shown in the figures, the element comprises a spherical reflective surface having a radius of curvature R1 and a spherical concave window having a radius of curvature R2. The window provides input and output of the beams before and after being reflected from the inside surface of the spherical mirror (from within the transparent body of the component). The window's radius of curvature R2, and center thickness T are chosen to produce aberration-free focusing of the beams similar to that produced by P-type catadioptric mirrors having a similar focal length f. Overlapping virtual confocal images are produced of the two fiber core ends at a virtual source point, which is then image-relayed into the tissue by the optical system. Either method of producing this virtual source point may be used as well as other methods.

Figure 47:
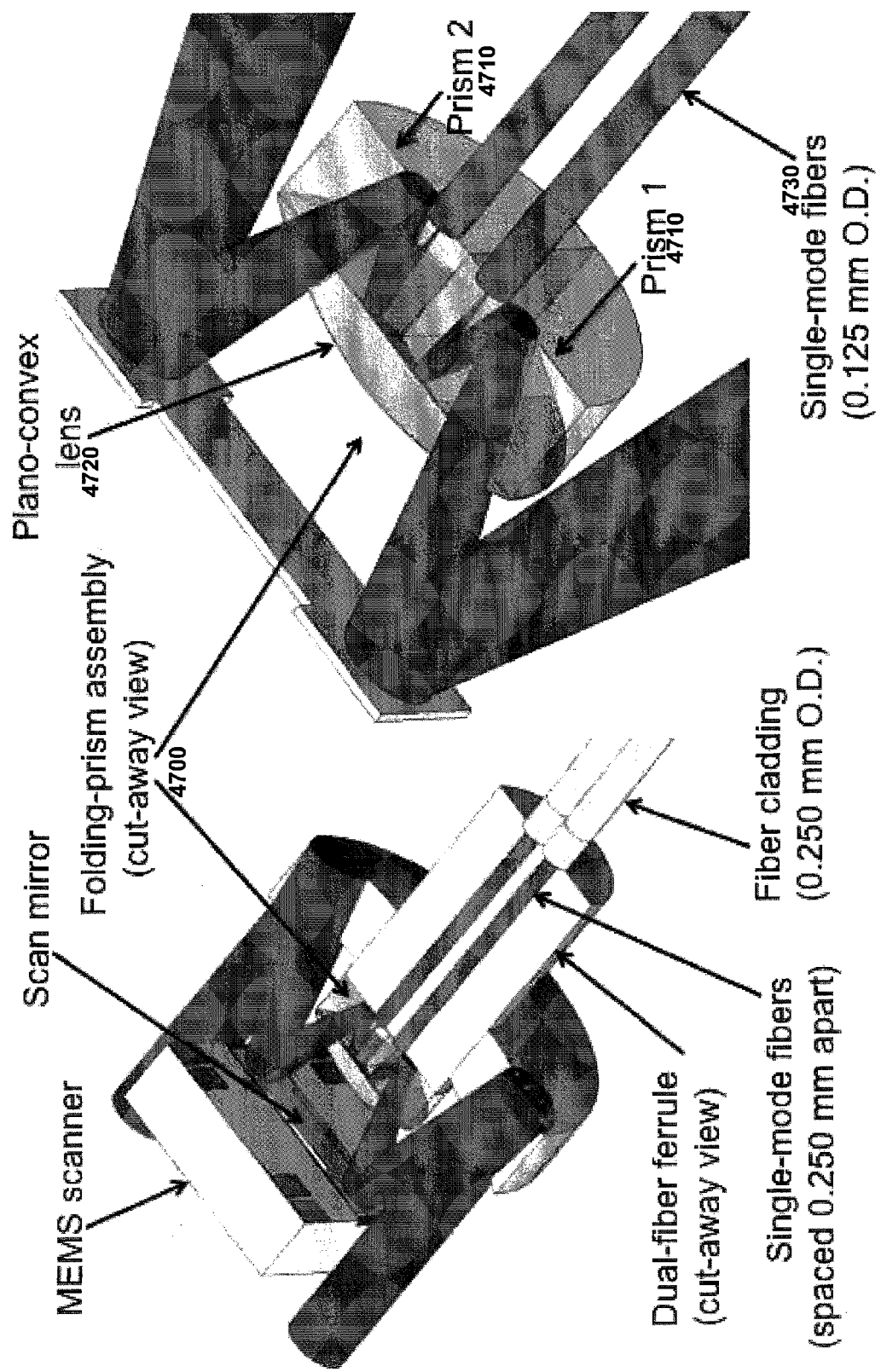
FIG. 47 shows a folding-prism assembly, in accordance with the instant disclosure.

FIG. 47 shows a folding-prism assembly 4700, in accordance with another embodiment, for producing both the proper angle between the beams and for superimposing the virtual images of the fiber cores at a single point. The folding-prism assembly includes two prisms 4710 and a plano-convex lens 4720, assembled and aligned in relation to the two single-mode fibers 4730. The radius of curvature of the lens is given by R4, and is chosen match the wavefront curvature of the beams as they enter and exit the assembly as shown in FIG. 46. This element reduces the aberrations that may otherwise occur at the air-glass interfaces of this particular optical assembly.

Figure 48:
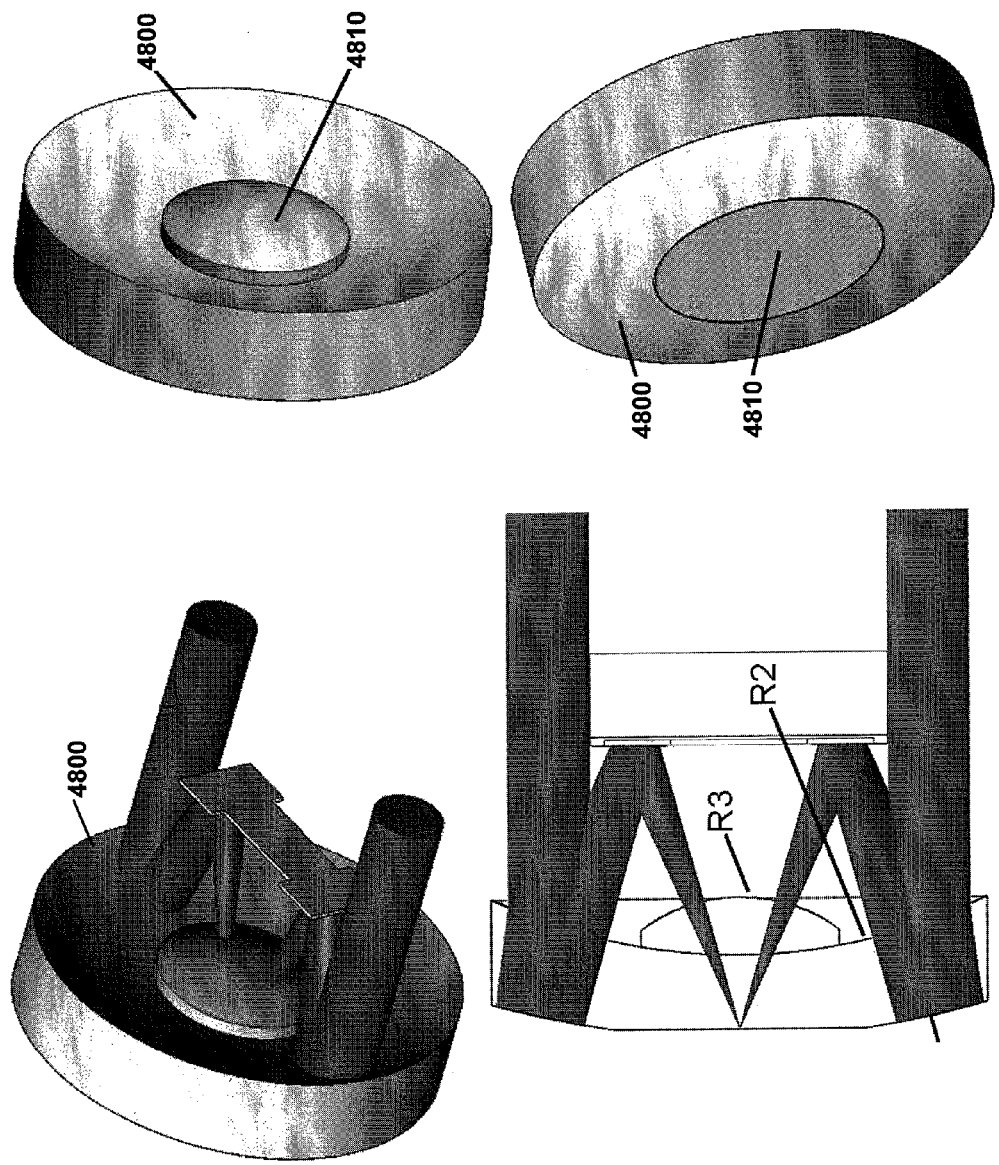
FIG. 48 shows a variation of an S-type catadioptric mirror specifically designed for positioning at the "tissue-imaging-end" of the DAC microscope, in accordance with another example embodiment.

FIG. 48 shows a variation of an S-type catadioptric mirror 4800 specifically designed for positioning at the "tissue-imaging-end" of the DAC microscope, in accordance with another example embodiment. The S-type catadioptric mirror shown in FIG. 48 is configured to permit a second lens element 4810 to be glued into the central area. In one implementation, this second element is a biconvex lens having two convex surfaces with radii of curvature R2 and R3. The convex curvature (R2) of this element is matched to the concave curvature (R2) of the window surface of the S-type catadioptric mirror. All the surfaces defined by R1 thru R4 are spherical surfaces. The value of R3 is chosen to match the wavefront curvature of the beams entering and exiting the tissue can provide a function similar to that of a SIL. The S-type catadioptric mirror includes a spherical reflective surface (for internal reflection) having a radius of curvature R1 and a spherical concave window having a radius of curvature R2. The window provides input and output of the beams before and after being reflected from the inside surface of the spherical mirror (from within the transparent body of the component).

The window's radius of curvature R2, and center thickness T can be chosen to produce aberration-free focusing of the beams similar to that produced by P-type catadioptric mirrors having a similar focal length f. The value of R1 is first chosen to produce a desired focal length f of the component and then R1 is held fairly constant while searching for values of R2 and T to produce aberration-free focusing. This type of optimization can be accomplished using a ray tracing program such as Zemax.

In some implementations, the materials for each of the two elements in the two-element assembly are both chosen to be fused silica in order to be closely matched to the refractive index of most tissues. Then the radius of curvature parameter R1 of the spherical mirror surface is chosen to achieve a focal length that is close to the desired value. The next two parameters for selection are the window radius of curvature R2, and the central thickness T. These parameters are adjusted in order to minimize the aberrations (e.g., spherical, astigmatism, coma, chromatic, etc.) of the focused beams in the tissue. Since changing the curvature of the window also affects the focal length, this procedure can be iterated until a final design having the desired focal length results.

Figure 49:
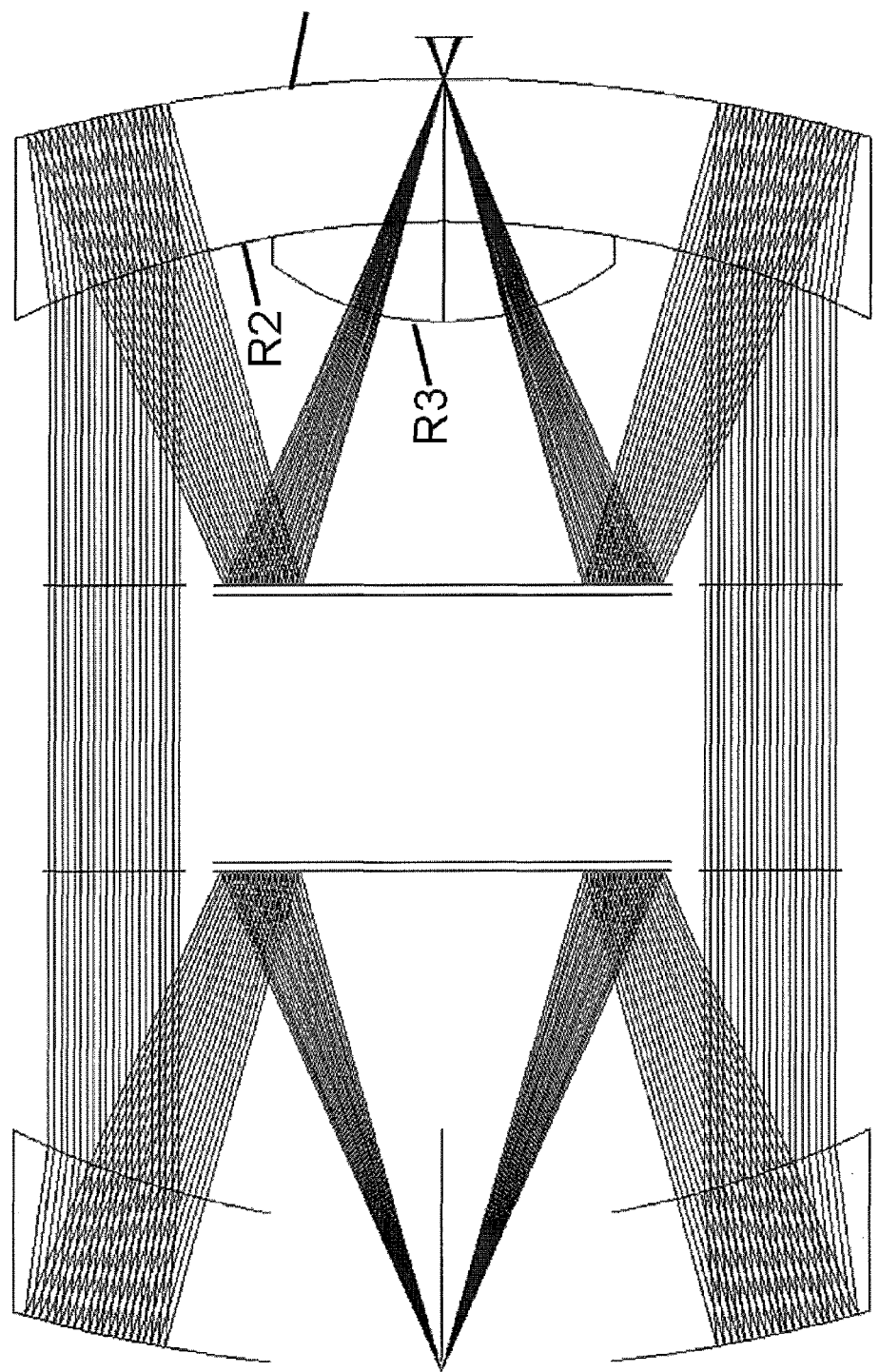
FIGS. 49-51 show various raytrace-type diagrams for directing light in accordance with various embodiments of this disclosure.
Figure 50:
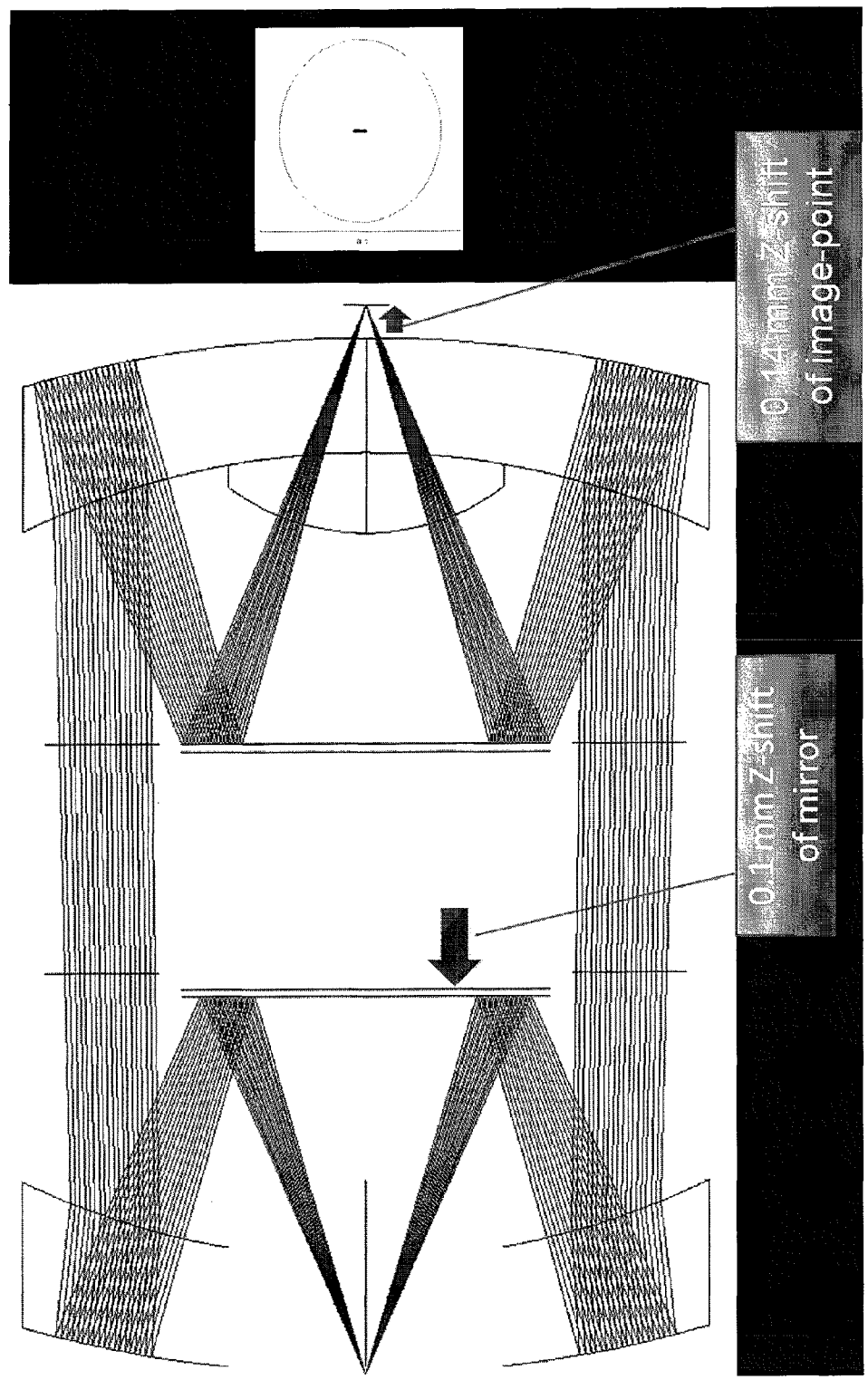
Figure 51:
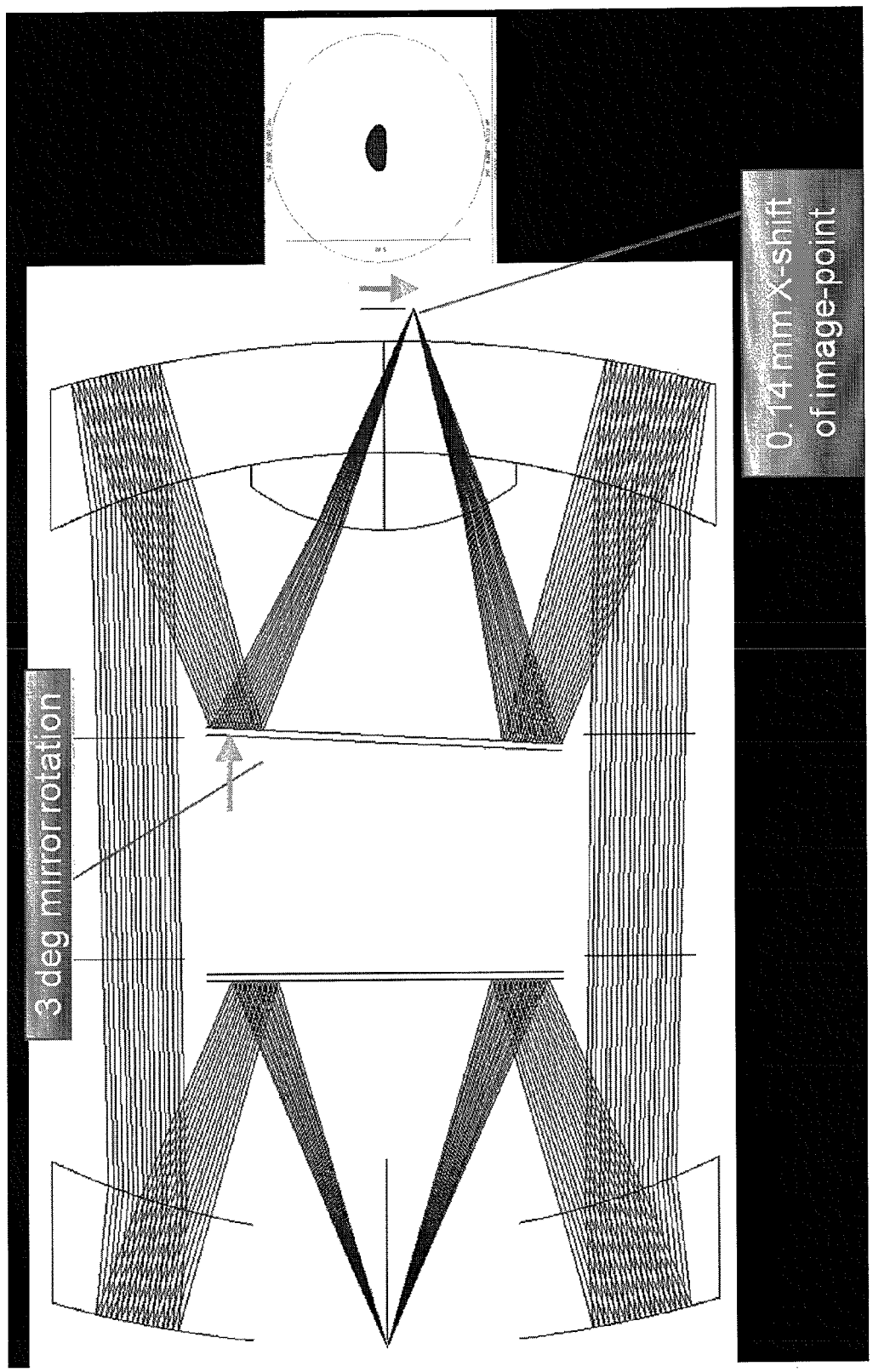

FIGS. 49-51 exemplify various raytrace-type diagrams for directing light in accordance with various embodiments as discussed herein.

Figure 52:
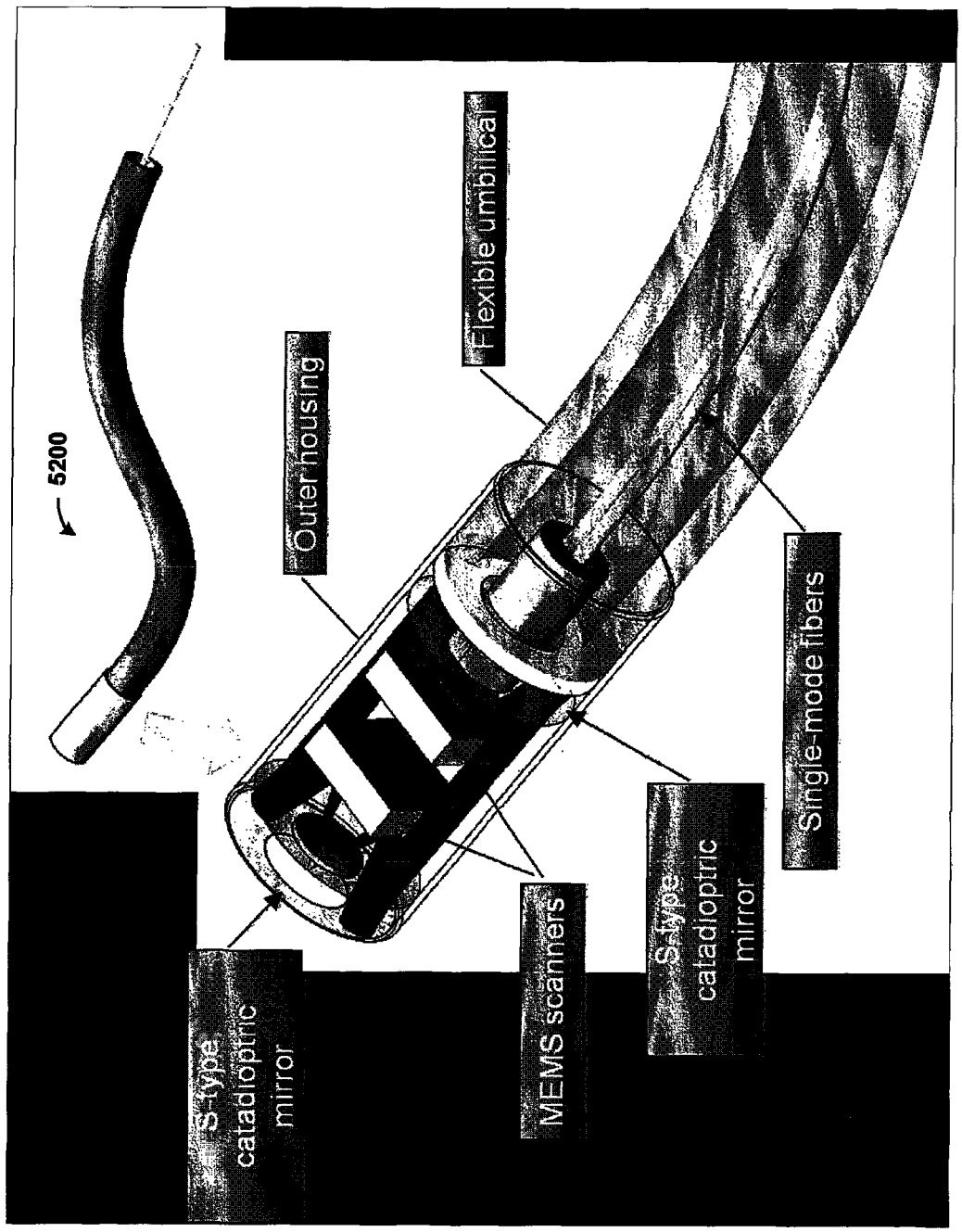
FIG. 52 depicts a microendoscope with S-type catadioptric mirrors in accordance with various embodiments of this disclosure.

FIG. 52 depicts a microendoscope 5200 with S-type catadioptric mirrors, in accordance with another example embodiment. The microendoscope 5200 may be implemented with components as discussed with endoscopes herein above and shown in the figures, with an S-type catadioptric mirror 5210 at an end thereof.

Other example embodiments are directed to a method for navigation of DAC microendoscopes to fluorescent targets in tissue, using a dual-modality instrument having a wide-field fluorescence mode for providing images that allow navigation of the instrument within a hollow organ, for accurate placement of the microscope and performing microscopic examinations of the tissue. The DAC microendoscopes are miniaturized microscopes that take advantage of the properties offered by the DAC microscope architecture, which facilitates integration of fiber optics, micro-optics, and microelectromechanical systems (MEMS) components into small form factors, and in addition, provides high-resolution optical sectioning properties required for imaging in biological tissues. Such miniaturized microscopes can thus be used by insertion into the instrument channels of standard medical endoscopes to enable fluorescence imaging of tissues in living subjects (in vivo) at the cellular scale. This approach can be used for a variety of purposes, such as cancer imaging in a clinical setting.

Turning again to FIG. 11, the figure shows an example targeted fluorescent contrast agent used for fluorescence imaging of tissues with a multifunctional DAC microendoscope platform, in connection with various example embodiments. For example, a Cox-2 enzyme can be used as a specific target for developing a multimodal (fluorescent/photoacoustic) contrast agent for use in imaging tissues with a multimodal DAC microendoscope. A targeting ligand (indomethacin) and an imaging tag (5-ROX) can be used to construct the multimodal (fluorescent/photoacoustic) contrast agent for use in imaging tissues.

Figure 53:
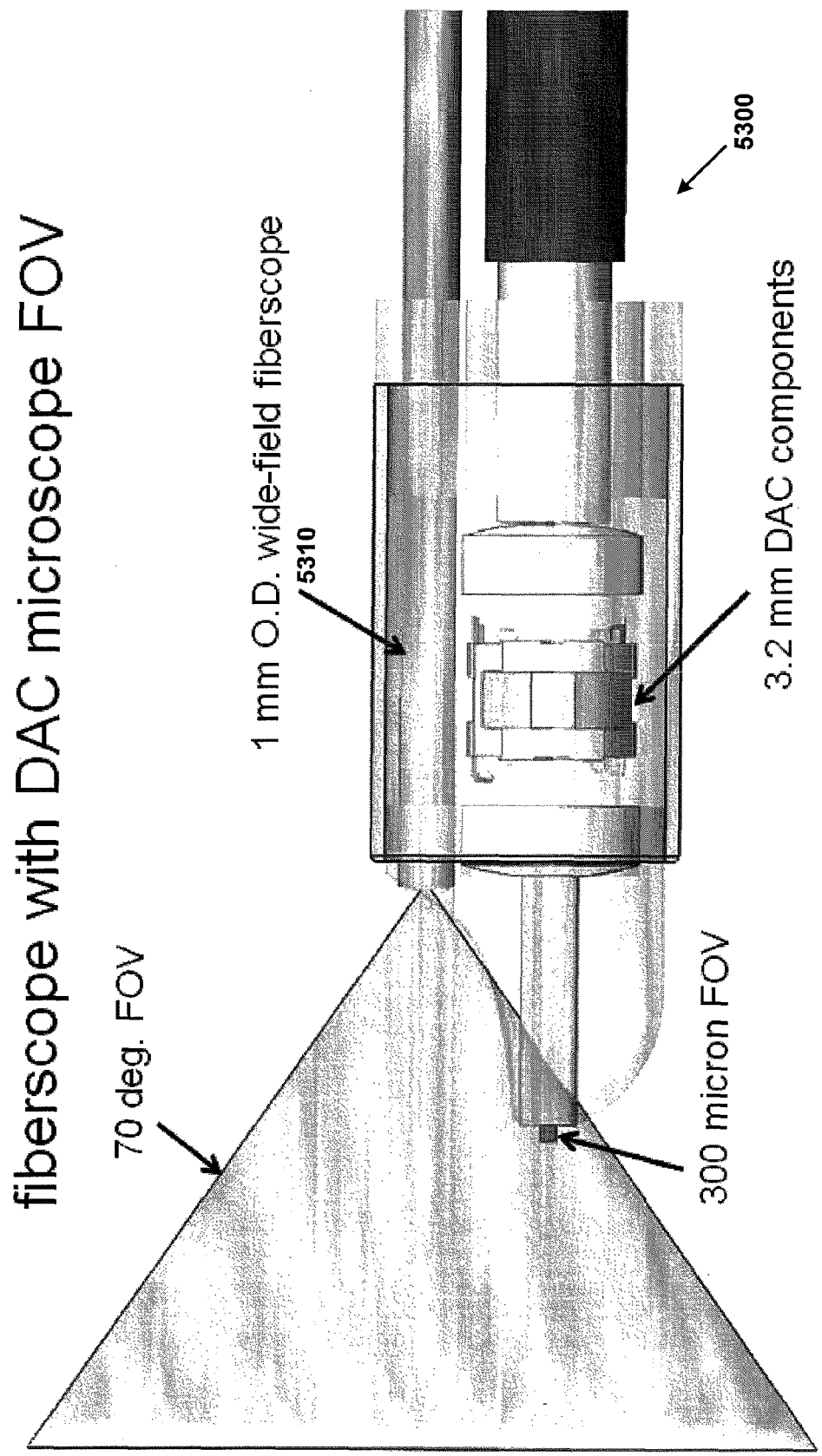
FIG. 53 shows one example microendoscope, based on aspects of the instant disclosure, with a wide-field fiberscope and a scanning microscope using dual scanning mirrors and collimating optics.
Figure 54:
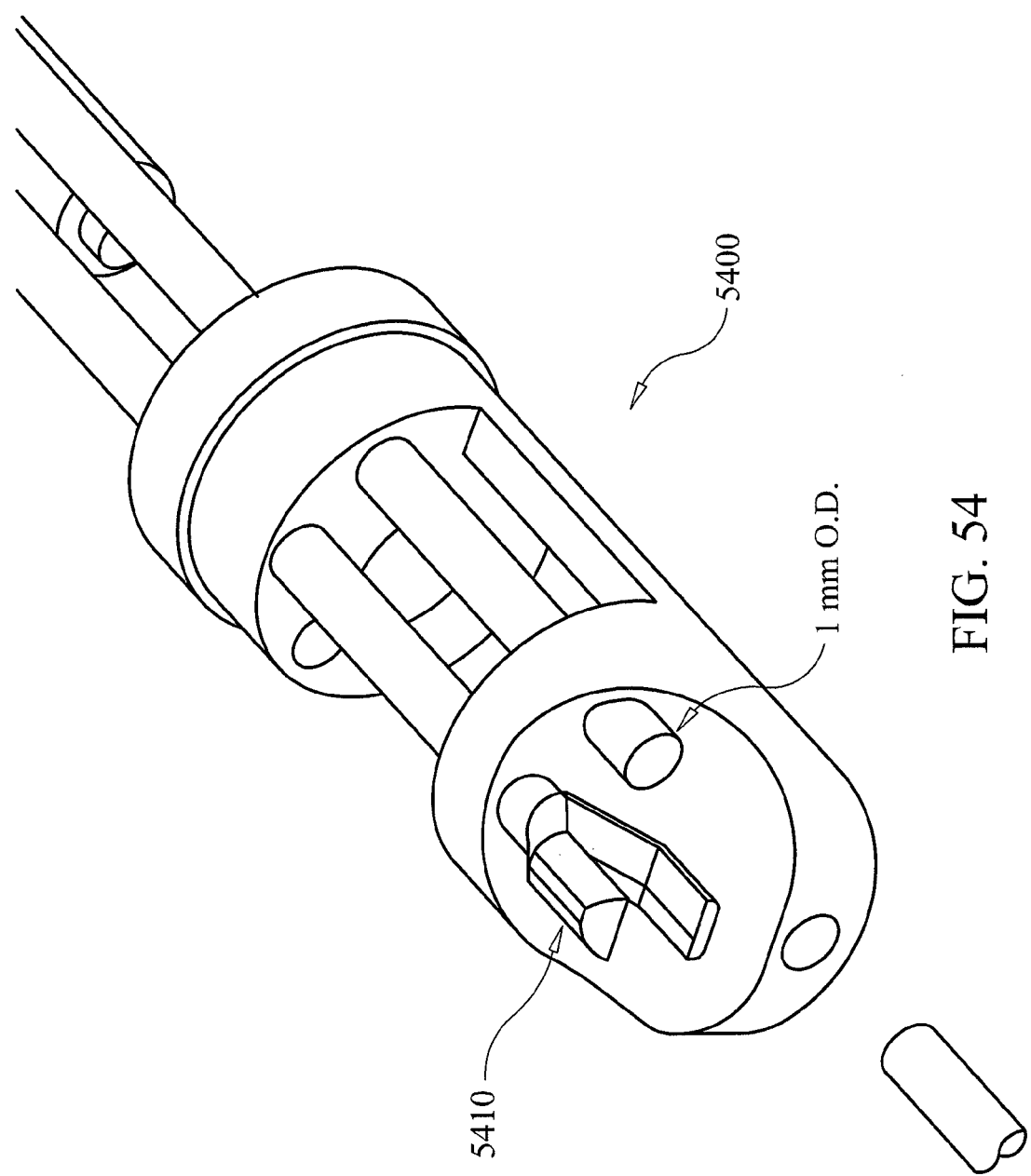
FIG. 54 shows a microendoscope, based on aspects of the instant disclosure, including a tool for use in removing tissue for a contact-based investigation of tissue.

The wide field/DAC microendoscope combination may include one or more of a variety of components. FIG. 53 shows one example microendoscope 5300 with a wide-field fiberscope 5310 and a scanning microscope using dual scanning mirrors and collimating optics as discussed herein, such as for non-contact investigation. FIG. 54 shows a similar microendoscope 5400, also including a tool 5410 for use in removing tissue for a contact-based investigation of tissue.

The embodiments and specific applications discussed herein, and in the underlying provisional application (and the Appendices included therein as part of the provisional application) may be implemented in connection with one or more of the above-described aspects, embodiments and implementations, as well as with those shown in the figures. Various embodiments described above, and discussed in the provisional application may be implemented together and/or in other manners. One or more of the items depicted in the present disclosure and in the Appendices can also be implemented in a more separated or integrated manner, or removed and/or rendered as inoperable in certain cases, as is useful in accordance with particular applications. In view of the description herein, those skilled in the art will recognize that many changes may be made thereto without departing from the spirit and scope of the present invention.

What is claimed is:

1. An apparatus comprising:
a first scanning mirror arrangement facing a first direction and configured and arranged to direct source light and image light in two paths, the first scanning mirror arrangement having a first axis of movement and a second axis of movement; and
a second scanning mirror arrangement facing a second direction that is different than the first direction and having a third axis of movement that is different than the first and second axes of movement and orthogonal to a target, the second scanning mirror arrangement configured and arranged to translate along the third axis and direct the image light from the target to the first scanning mirror arrangement, the first and second scanning mirror arrangements having different scanning axes and being cooperatively arranged to
  scan the source light directed from the first scanning mirror arrangement and via the second scanning mirror arrangement to target locations with at least two degrees of freedom, and
  direct image light from the target locations via the second scanning mirror arrangement to the first scanning mirror arrangement, the source light and image light being passed between the first and second scanning mirror arrangements in collimated beams, whereby the target location is moved via the cooperative movement of the first and second scanning mirror arrangements.

2. The apparatus of claim 1, wherein the first and second scanning mirror arrangements respectively include first and second parabolic mirrors that are fixed relative to and facing one another, and respectively include first and second scanning mirrors facing away from one another, the second scanning mirror having an axis of movement that is orthogonal to the target, in which the mirrors collectively provide three degrees of freedom for adjusting the target location to which the source light is directed along the three axes by
  scanning source light from the first scanning mirror to the first parabolic mirror, from the first parabolic mirror to the second parabolic mirror, from the second parabolic minor to the second scanning mirror, and from the second scanning mirror to the target,
  while scanning the source light, directing image light from the target to the second parabolic mirror, from the second parabolic mirror to the first parabolic mirror, from the first parabolic mirror to the first scanning mirror, and from the first scanning mirror to a detector, and
  wherein the source light and image light are passed between the first and second parabolic mirrors along parallel paths, and the first and second scanning mirrors are configured and arranged with one another to cooperatively rotate along parallel axes for concurrently scanning the source light and detecting the image light.

3. The apparatus of claim 1, wherein the first axis of movement and the second axis of movement are torsional axes, and the third axis of movement is a piston motion axis, the apparatus further including beam-shaping optics configured to direct light between the first and second scanning mirror arrangements, and the second scanning mirror arrangement configured and arranged to vary a working distance to the target by moving along the third axis of movement.

4. The apparatus of claim 3, wherein the beam-shaping optics are configured and arranged to collimate light for passing between the first and second scanning mirror arrangements.

5. The apparatus of claim 1, further including a multimodal end-piece interface configured and arranged to
  direct and receive the source and image light between the target locations and the second scanning mirror arrangement to provide image information in a first modality, and
  acquire information from the target location in a second modality.

6. The apparatus of claim 5, wherein the multimodal end-piece interface is configured and arranged to direct and receive the source and image light while acquiring the information in a second modality, to concurrently provide information for two modalities.

7. The apparatus of claim 5, wherein the first and second scanning mirror arrangements are configured and arranged to actuate in different manners based upon a type of end-piece connected to the multimodal end-piece interface.

8. The apparatus of claim 1, wherein at least one of the scanning mirror arrangements includes a mirror having two reflective sections that are respectively configured and arranged to simultaneously deflect two beams of the light to focus the two beams to the target.

9. A multimodal endoscopic apparatus comprising:
  a scan-engine module including
    a first scanning mirror arrangement facing a first direction and configured and arranged to direct source light and image light in two paths, and including a first scanning mirror having two axes of movement,
    a second scanning mirror arrangement facing a second direction that is different than the first direction and cooperatively arranged with the first scanning mirror arrangement to direct light received from the first scanning mirror arrangement to a target, and direct image light from the target to the first scanning mirror arrangement, the second scanning mirror arrangement including a second scanning mirror having a third axis of movement that is orthogonal to the target axis and being configured to translate along the third axis, the first and second scanning mirror arrangements being configured and arranged to collectively provide three degrees of freedom for scanning the target, and
    mirrors configured and arranged to direct light along parallel and separate paths between the first and second scanning mirror arrangements; and
  a multimodal end-piece interface configured and arranged to interface with a plurality of different end pieces to facilitate acquisition of information for multiple modalities.

10. The apparatus of claim 9, wherein the scan-engine module and multimodal end-piece interface are configured and arranged to concurrently acquire light-based information and at least one additional type of information to facilitate multiple modalities.

11. The apparatus of claim 9, wherein the first and second directions are opposite one another, and the scan-engine module and multimodal end-piece interface are configured and arranged to concurrently acquire at least two sets of information including light-based information, to provide information for one of the multiple modalities.

12. The apparatus of claim 9, wherein the scan-engine module is configured and arranged to actuate the scanning mirror arrangements in different manners respectively based upon a type of end-piece connected to the multimodal end-piece interface.

13. The apparatus of claim 9, further including a GRIN relay lens in the optical path of the light and configured and arranged to couple with different types of end-pieces connected to the multimodal end-piece interface.

14. The apparatus of claim 9, further including a micromachined ultrasonic transducer configured and arranged to apply and detect ultrasonic waves to characterize the target.

15. The apparatus of claim 9, wherein the first and second scanning mirror arrangements are configured and arranged to scan light about different scanning axes to collectively provide three degrees of freedom for scanning the target by scanning light to target locations within tissue along three different axes.

16. The apparatus of claim 9, wherein at least one of the scanning mirror arrangements includes a mirror having two reflective sections that are respectively configured and arranged to simultaneously deflect two beams of the light to focus the two beams to the target.

17. An endoscopic apparatus comprising:
  a dual-axis scanning mirror arrangement facing a first direction and having a first and a second axis of movement and configured and arranged to re-direct light in two paths respectively for source light and image light;
  a first beam-shaping mirror configured and arranged to redirect source light from the dual-axis scanning mirror in a first collimated beam, and to redirect collimated light to the dual-axis scanning mirror arrangement received from a second collimated beam;
  a second beam-shaping mirror configured and arranged to redirect the collimated source light received from the first beam-shaping mirror via the first collimated beam, and to redirect image light to the first beam-shaping mirror via the second collimated beam; and
  a single-axis scanning mirror arrangement facing a second direction that is different than the first direction configured and arranged to direct the collimated source light received from the second beam-shaping mirror to a target, to direct image light from the target to the second beam-shaping mirror via the second collimated beam, and to translate along a third axis that is orthogonal to the target to vary a working distance to the target.

18. The apparatus of claim 17, wherein the dual-axis scanning mirror arrangement includes a silicon-based circuit including an actuator and dual mirrors, the actuator being configured and arranged to actuate the dual mirrors to scan light across the target.

19. The apparatus of claim 17, wherein the single-axis scanning mirror arrangement includes a silicon-based circuit including an actuator and dual mirrors, the actuator being configured and arranged to actuate the dual mirrors along the axis to set the working distance between the single-axis scanning mirror arrangement and the target.

20. The apparatus of claim 17, wherein
the dual-axis scanning mirror arrangement includes a silicon-based circuit including an actuator and dual mirrors, the actuator being configured and arranged to actuate the dual mirrors to scan light across the target; and
the single-axis scanning mirror arrangement includes a silicon-based circuit including an actuator and dual mirrors, the actuator being configured and arranged to actuate the dual mirrors along the axis to set the working distance between the single-axis scanning mirror arrangement and the target.

21. The apparatus of claim 17, wherein
the collimated beams are parallel to one another, and
the single-axis scanning mirror arrangement is configured and arranged to move along the third axis to vary a depth of scanning of the target, wherein the third axis is also parallel to the collimated beams.

22. The apparatus of claim 17, wherein the single-axis scanning mirror arrangement is configured and arranged to move along the third axis to vary the working distance to the target according to a wavelength of the collimated light.

23. The apparatus of claim 17, wherein the dual-axis scanning mirror includes a mirror having two reflective sections that are respectively configured and arranged to simultaneously deflect two beams of the light to focus the two beams to the target.

* * * * *